United States Patent
German

(10) Patent No.: US 7,966,134 B2
(45) Date of Patent: *Jun. 21, 2011

(54) SYSTEMS AND METHODS TO DETERMINE ELASTIC PROPERTIES OF MATERIALS

(76) Inventor: Peter Thomas German, Altadena, CA (US)

( * ) Notice: Subject to any disclaimer, the term of this patent is extended or adjusted under 35 U.S.C. 154(b) by 94 days.

This patent is subject to a terminal disclaimer.

(21) Appl. No.: 12/383,390

(22) Filed: Mar. 23, 2009

(65) Prior Publication Data

US 2009/0210158 A1    Aug. 20, 2009

Related U.S. Application Data

(62) Division of application No. 11/093,482, filed on Mar. 29, 2005, now Pat. No. 7,107,159.

(60) Provisional application No. 60/557,365, filed on Mar. 29, 2004.

(51) Int. Cl.
*G01L 1/00* (2006.01)
*G01L 3/00* (2006.01)
*G01L 5/00* (2006.01)
*G06F 19/00* (2011.01)

(52) U.S. Cl. ........... 702/41; 702/33; 73/379.01; 73/573; 73/574; 73/575; 73/576; 73/577; 73/578; 73/579

(58) Field of Classification Search ................ 702/2, 33, 702/41; 73/379.01, 573–579, 805, 806, 808, 73/812, 815, 818, 826, 841, 844
See application file for complete search history.

(56) References Cited

U.S. PATENT DOCUMENTS

| 3,836,757 | A | 9/1974 | Nachtigal et al. |
| 5,495,763 | A | 3/1996 | Rhodes |
| 6,289,734 | B1 | 9/2001 | Daugela |
| 6,324,915 | B1 * | 12/2001 | Potts .............................. 73/808 |
| 6,522,974 | B2 | 2/2003 | Sitton |

FOREIGN PATENT DOCUMENTS

FR    2616908 A1    12/1988

OTHER PUBLICATIONS

Kerschen, et al., 2001 Journal of Sound and Vibration 244(4):597-613 "Theoretical and Experimental Identification of a Non-Linear Beam".
Doughty, et al., 2002 Journal of Sound and Vibration 249(4):785-813 "A Comparison of Three Techniques Using Steady State Data to Identify Non-Linear Modal Behavior of an . . . ".

(Continued)

*Primary Examiner* — Sujoy K Kundu

(57) ABSTRACT

The present invention provides systems and methods to use a measured driving-point response of a nonlinear material to determine one or more elastic properties of the material. The present invention takes advantage of the full information represented by the transient component, the steady-state component, the anharmonic components, and the nonlinear response components of a measured driving-point response of a real nonlinear material, without limitation in the use of large-amplitude forces. The elastic properties are determined by forming and solving a time-domain system of linear equations representing a differential equation model of the driving-point motions of the material. Based on a single, short duration, large-amplitude driving point measurement, both linear and nonlinear properties can be determined; both large-amplitude and near-zero amplitude properties can be determined; and elastic-wave speed and elastic moduli and their variation with depth can be determined.

44 Claims, 14 Drawing Sheets

OTHER PUBLICATIONS

Communication from the European Patent Office of Applicant's corresponding application EP 05734861.7, dated Nov. 23, 2009, 6 pages.

Wulich et al, 1990a, "PLL based discrete time varying filter for estimation of parameters . . . ", Proc. Int'l Symp. Circuits & Syst. IEEE, May 1990, v1:771-774.

Wulich et al, 1990b, "Constrained notch filtering of nonuniformly spaced samples . . . ", IEEE Trans. Acoust. Speech & Sig. Proc, 39(10):2359-2363. [US].

Wulich et al, 1991, "Synthesis of discrete time-varying null filters for frequency-varying signals . . . ", IEEE Trans. Circuits & Syst, 37(8):977-990. [US].

* cited by examiner

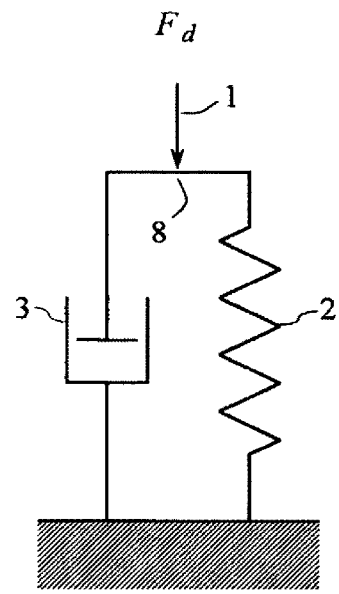
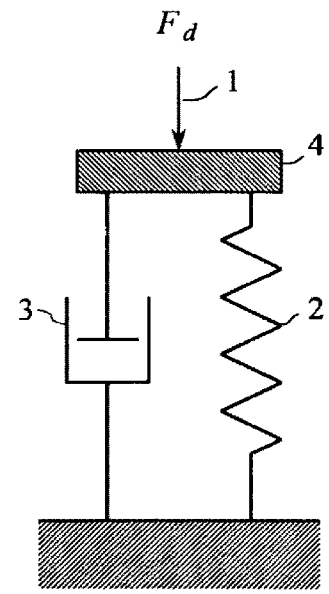
FIG. 1A  FIG. 1B
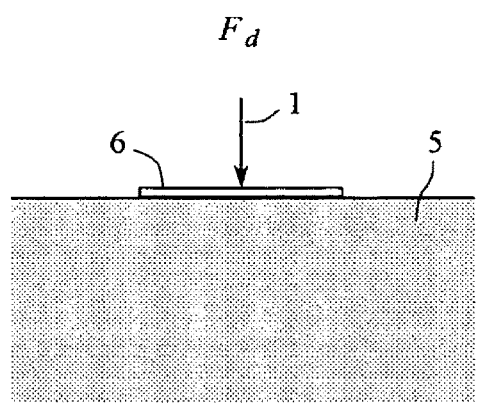
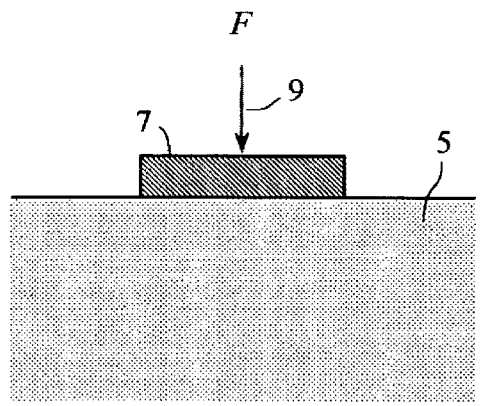
FIG. 1C  FIG. 1D

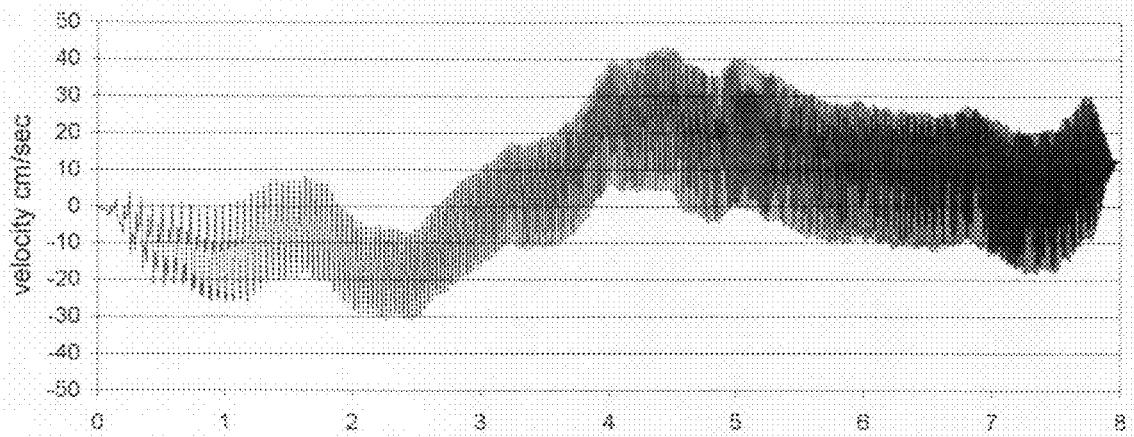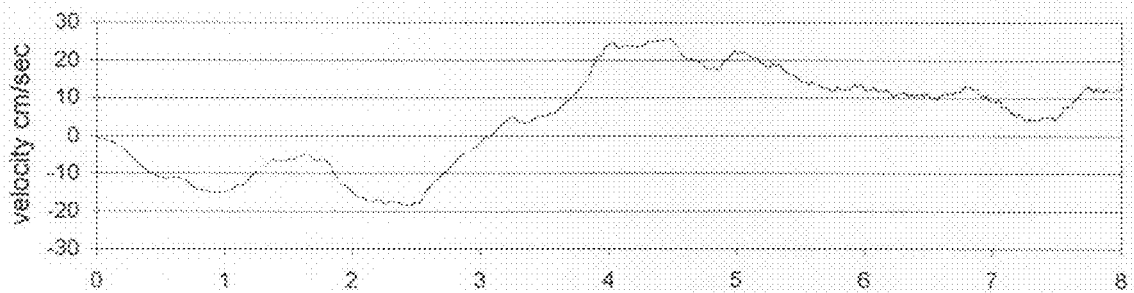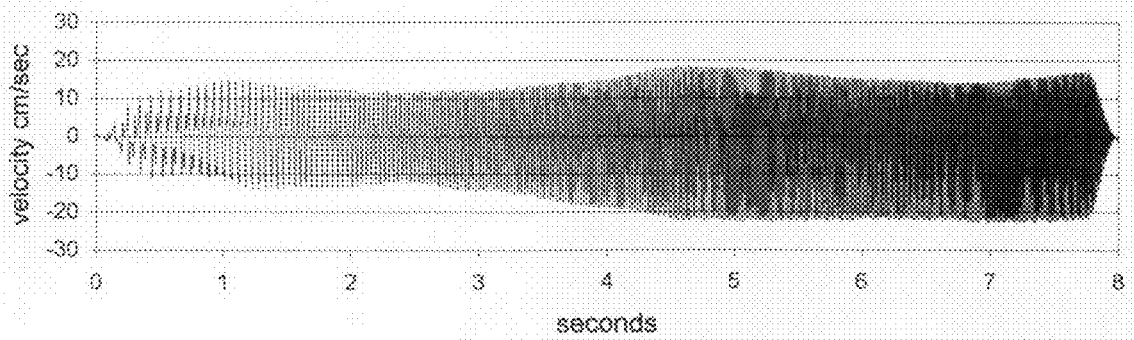

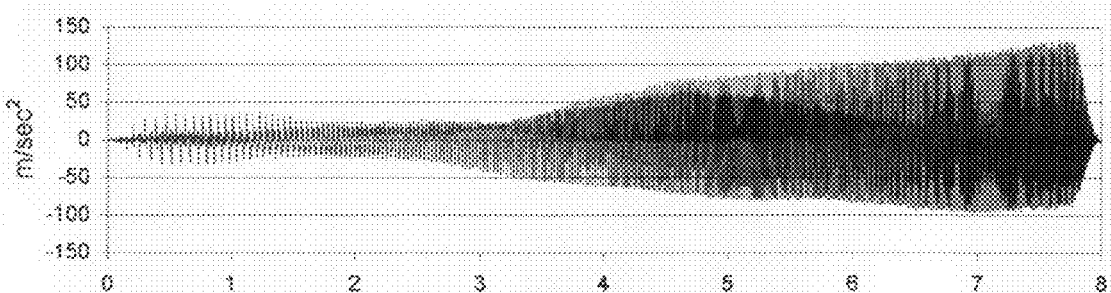
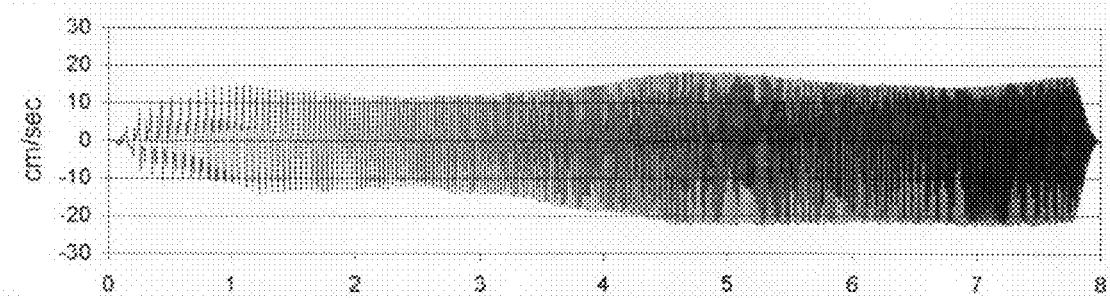
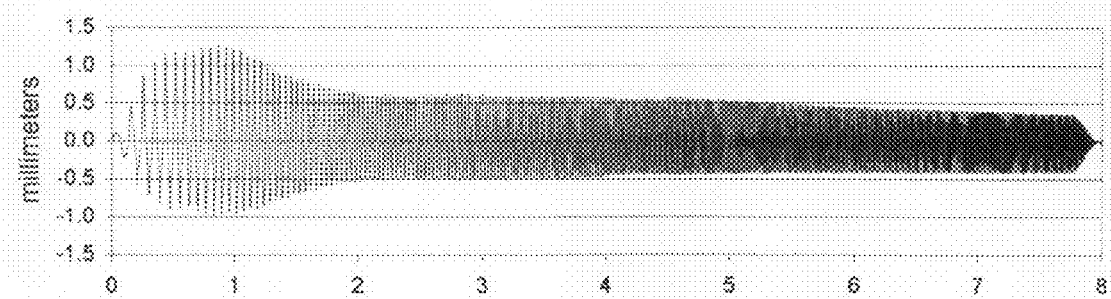
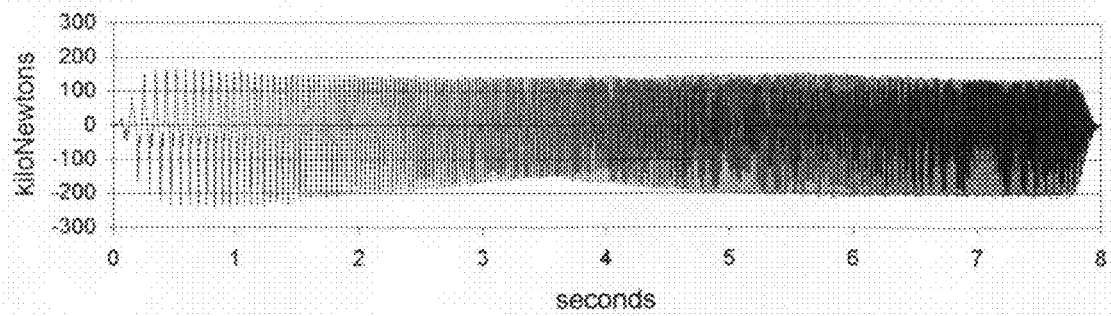

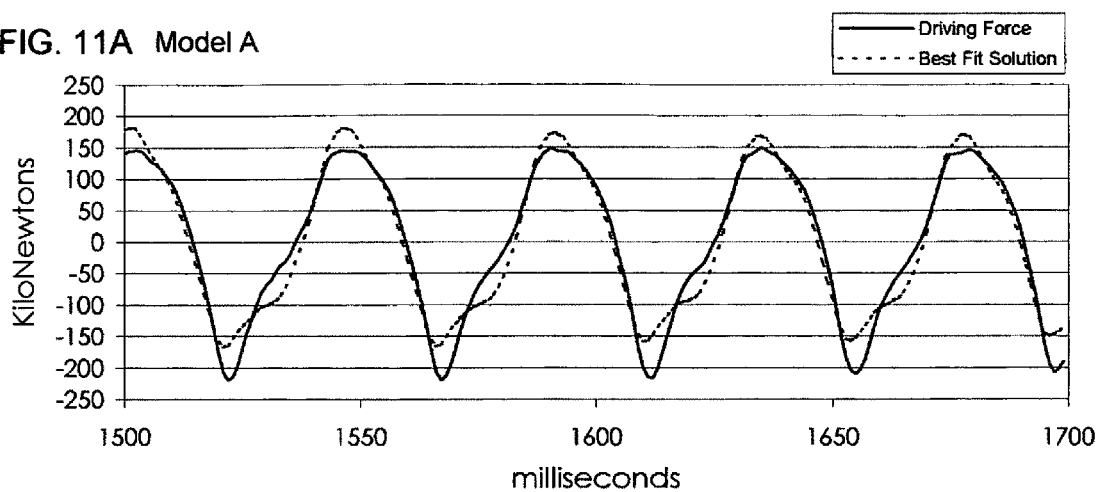
FIG. 11A  Model A
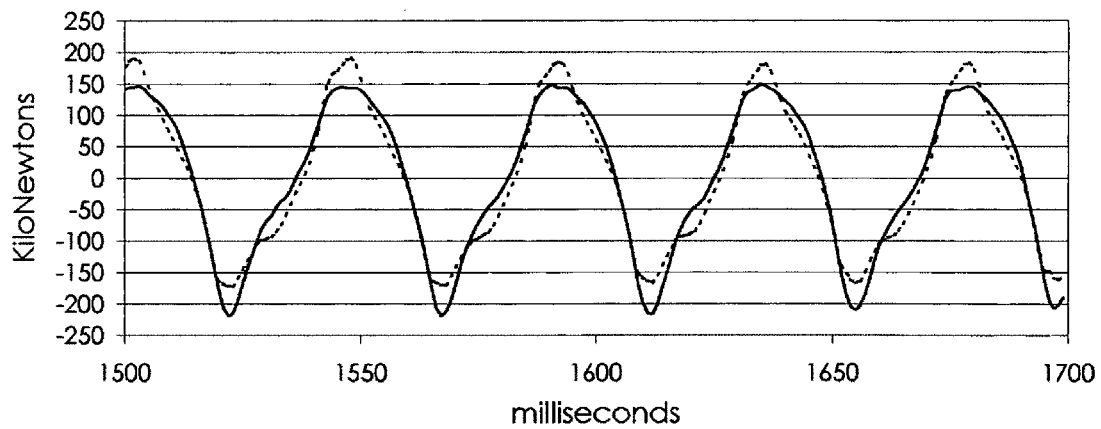
FIG. 11B  Model B
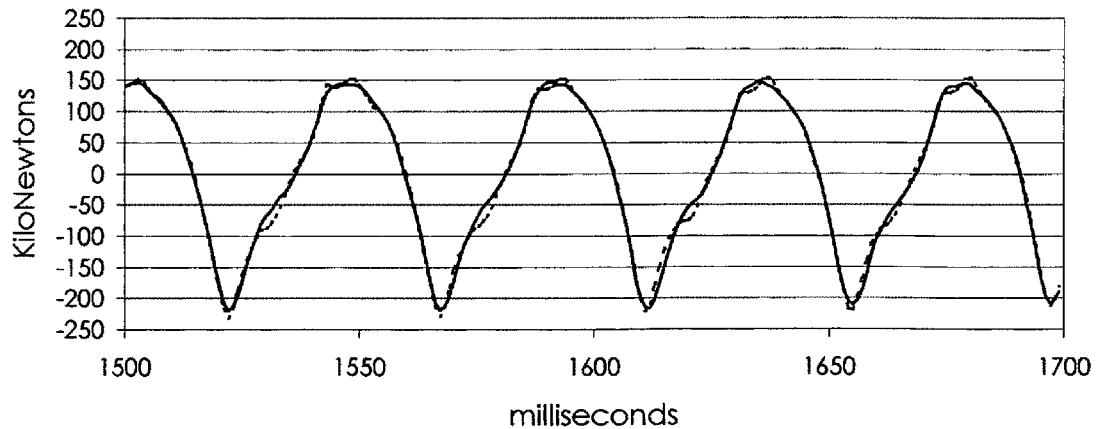
FIG. 11C  Model C

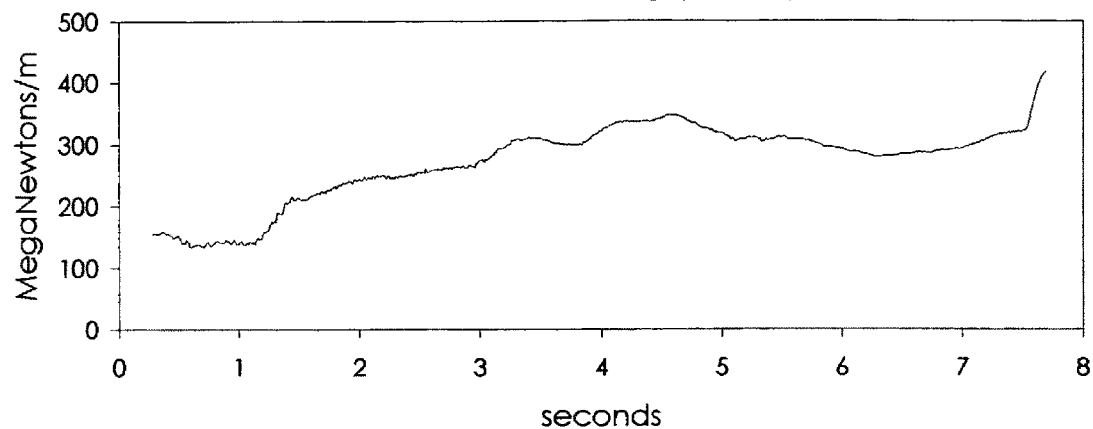
FIG. 14A First-order Stiffness: $k_1$ (Model C)
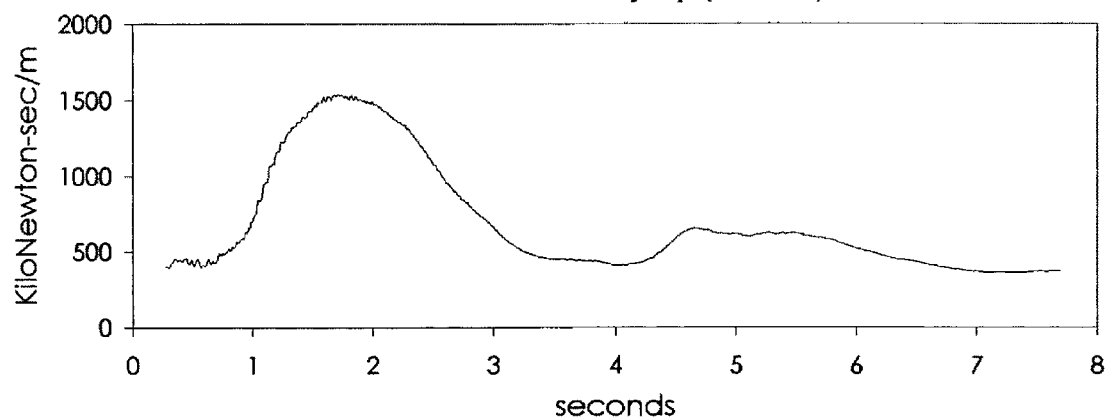
FIG. 14B First-order Viscosity: $b_1$ (Model C)
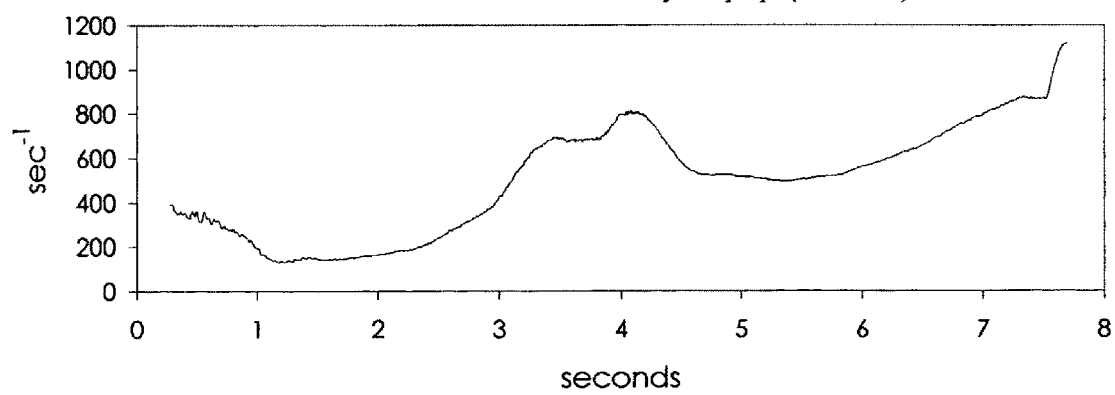
FIG. 14C Ratio of Stiffness to Viscosity: $k_1/b_1$ (Model C)

SYSTEMS AND METHODS TO DETERMINE ELASTIC PROPERTIES OF MATERIALS

This patent application is a divisional application claiming the priority of U.S. Ser. No. 11/093,482, filed Mar. 29, 2005, which claims priority of U.S. provisional application Ser. No. 60/557,365, filed Mar. 29, 2004, now U.S. Pat. No. 7,107,159. The contents of all the foregoing patent applications are hereby incorporated by reference in their entirety into the present application.

Throughout this application various publications are referenced. The disclosures of these publications in their entireties are hereby incorporated by reference into this application in order to more fully describe the state of the art to which this invention pertains.

FIELD OF THE INVENTION

The present invention relates to the measurement of properties of nonlinear elastic materials, and more particularly to systems and methods for measurement of elastic properties based on a driving-point response of a nonlinear elastic material; to systems of linear equations; and to signal filtering. In one embodiment the present invention relates to measurement of in situ elastic properties of earth materials, such as foundation soils or geologic formations. In another embodiment the present invention relates to using a seismic vibrator for measurement of a driving-point response.

BACKGROUND

The elastic properties of the materials used in many fields are often critical to the design, operation, utility, or safety of the uses of these materials. In the field of manufacturing, the elastic properties of manufactured materials and their components often must meet defined specifications which are essential to the utility and safety of the manufactured products. In the medical field, elastic properties of biological tissues is important for ultrasound imaging. In the field of construction, the elastic properties of construction materials and of foundation soils are important design criteria and critical safety considerations for engineered structures, roads, dams, excavations, and earthworks. In the field seismic surveying, the measurement of spatial variation and depth variation of near-surface elastic wave speed in the earth is important for seismic imaging methods used for hydrocarbon exploration. In the field of seismic hazard mitigation, the elastic properties of soil and geologic formations at the surface of the earth are a critical element in assessing and mitigating hazards in areas prone to strong earthquake shaking. In all these fields, it is useful and often essential to have an efficient, reliable means to test elastic properties of the materials in question.

It is well known that the elastic properties of a material can be tested by measuring the elastic response of a material to an applied dynamic driving force. In laboratory tests, a testing apparatus typically constrains a sample of the material to restrict the elastic response to certain defined modes or directions of motion, applies known confining pressures, and provides a means to measure the dynamic dimensions and shape of the body of material as needed. However, for many important types of materials it is time consuming, costly, or impractical to constrain the material in a test apparatus. Also, for some materials the process of isolating a sample of the material changes the elastic properties, a particular example being soils. There is therefore a need to efficiently and reliably measure the elastic properties of an unconstrained, unaltered material. Methods have previously been proposed for testing an unconstrained material by measuring the motion of the material at the same point where a measured dynamic driving force is concurrently applied. Because the motion measurement and force application are at the same place and time, the driving-point measurement process is very time efficient and access to only one measurement point is needed. However, it is a difficult problem to reliably determine elastic properties from the unconstrained driving-point motions of a real material.

For an ideal half-space of isotropic linear elastic material, it has previously been shown that the driving-point motion of the material comprises both transient and steady-state motions that are a complicated function of a combination of three independent elastic properties as well as being a function of frequency. Also, real materials are typically nonlinear and respond with anharmonic motions comprising a set of harmonic frequency components, and for highly nonlinear materials the anharmonic frequency components can dominate the response. Current practices for determining elastic properties from a measured driving-point response are typically variations of a LaPlace transform type analysis, wherein the complex ratio of the driving force to the measured motion is analyzed to determine a stiffness and/or viscosity of the material. The LaPlace type methods are based on a mathematical assumption of a sinusoidal driving force, assumption of a small-amplitude approximation for the motion of a linear material, and an assumption of a steady-state response. These assumptions limit the usefulness of these methods to low-amplitude driving forces applied for sufficiently long duration to approximate a steady-state response. Most of these assumptions are violated to some degree in real measurements. Because the low-amplitude measurements are more sensitive to measurement error and noise contamination, another current practice is determine the elastic properties based on an average value over a wide range of frequencies. Another practice known in the art is to attenuate both noise and anharmonic frequency components using a tracking filter. The low-amplitude limitation also restricts the usefulness in fields where larger driving-forces might otherwise be advantageous. For example, seismic vibrators used in seismic surveying produce very large driving forces far in excess of the low-amplitude limitations of the existing analysis methods. Hamblen et al. (U.S. Pat. No. 6,604,432) provide a method using a LaPlace-type analysis for estimating soil stiffness from a measured driving-point response, wherein the driving force must be limited to a low level, and the stiffness is averaged over a wide range of frequencies. The problem is that the stiffness and viscosity of a real, unconstrained material are a complicated function of frequency, and may not be well represented by an average value over a wide range of frequencies. Furthermore, the transient and anharmonic response components represent useful information about the elastic properties of real, nonlinear elastic material, so attenuating these components causes a loss of useful information. The transient components and anharmonic frequency components can represent a substantial portion of the total elastic energy in the measured motion of the driving point motion, and attenuating these components results in a misrepresentation of the relationship of the driving-force to the motion. Therefore, existing practices for analyzing a measured driving-point response to determine elastic properties of a material are of questionable reliability and subject to a number of substantial limitations.

The present invention provides systems and methods to use a measured driving-point response of a nonlinear material to determine one or more elastic properties of the material. The present invention takes advantage of the full information represented by the transient component, the steady-state component, the anharmonic components, and the nonlinear response components of a measured driving-point response of a real nonlinear material, without limitation in the use of large-amplitude forces. The elastic properties are determined by forming and solving a time-domain system of linear equations representing a differential equation model of the driving-point motions of the material. The time-domain differential equation model is free of the mathematical assumptions and limitations of existing methods. Based on a single, short duration, large-amplitude driving point measurement, both linear and nonlinear properties can be determined; both large-amplitude and near-zero amplitude properties can be determined; and elastic-wave speed and elastic moduli and their variation with depth can be determined.

SUMMARY OF THE INVENTION

The present invention provides a system for determining one or more elastic properties of a material, the system comprising: a first input means for receiving a first input signal representative of a driving force exerted on the material by an actuator at a driving-point; a second input means for receiving a second input signal representative of a driving-point velocity corresponding to the driving force; a third input means for receiving a third input signal representative of a driving-point displacement corresponding to the driving force; a signal generator means for generating a basis function signal for each one of a set of basis functions, the set of basis functions corresponding to the terms of a differential equation model of the motion of the driving-point, and each basis function comprising a function of any one or more of the input signals; and a processor means for analyzing the set of basis function signals in relation to the first input signal to determine coefficients of a linear combination of the basis function signals which best fits the first input signal, one or more of the coefficients then being representative of a value of one or more elastic properties of the material.

In one embodiment, the present invention provides a system for determining one or more elastic properties of an in situ material, the system comprising: a first input means for receiving a first input signal representative of a driving force exerted on the material by a dynamic actuator at a driving-point; a second input means for receiving a second input signal representative of a driving-point velocity corresponding to the driving force; a third input means for receiving a third input signal representative of a driving-point displacement corresponding to the driving force; a signal generator means for generating a basis function signal for each one of a set of basis functions, the set of basis functions corresponding to the terms of a force balance differential equation model of the motion of the driving-point, the differential equation model comprising a nonlinear spring-damper system represented by polynomial function of the driving-point displacement and a polynomial function of the driving-point velocity, and each other basis function comprising a function of any one or more of the input signals; and a processor means for analyzing the set of basis function signals in relation to the first input signal to determine coefficients of a linear combination of the function signals which best fits the first input signal, wherein each coefficient corresponding to a displacement term is then representative of a stiffness property of the material, and each coefficient corresponding to a velocity term is then representative of a viscosity property of the material.

The present invention also provides a system for filtering an input signal, the system comprising: a phase detector for generating a phase-sample timing signal representative of a sequence of times corresponding to substantially equal intervals of phase of a phase reference signal, wherein the equal intervals of phase comprise an integer number N of phase intervals per cycle of the phase reference signal; a sampler for sampling the input signal at the sequence of times corresponding to the phase-sample timing signal, thereby generating a phase-sampled signal; and a filter adapted for filtering the phase-sampled signal to generate a filtered signal, wherein the filter is adapted to either attenuate or preserve each of one or more selected components.

BRIEF DESCRIPTION OF THE DRAWINGS

FIGS. 1A-D depict several conceptual mechanical models of an elastic material which provide the conceptual basis for several differential equation models;

FIG. 1A depicts a spring-damper model;

FIG. 1B depicts a mass-spring-damper model;

FIG. 1C depicts an elastic half-space model driven by a massless driving element;

FIG. 1D depicts an elastic half-space model with a massive driving element.

FIG. 9A is a plot of a velocity signal produced by integration of a driving-point acceleration signal without the benefit of error attenuation, showing the severity of integration errors.

FIG. 9B is a plot of an estimated error signal output by a fractional-cycle-interval filter 10 using the velocity signal of FIG. 9A as input, illustrating the random character of the error signal.

FIG. 9C is a plot of an error-corrected driving-point velocity signal output by an error-attenuator 20 using the velocity signal of FIG. 9A as input, showing the benefit of the error-attenuator 20 for attenuating integration error and measurement error.

FIG. 10A is a plot of an error-corrected driving-point acceleration signal output by an anharmonic motion signal integrator 30, using a seismic vibrator baseplate acceleration signal as input, illustrating the test data described in Example 1.

FIG. 10B is a plot of an error-corrected driving-point velocity signal corresponding to the acceleration signal of 10A, produced by an anharmonic motion signal integrator 30.

FIG. 10C is a plot of an error-corrected driving-point displacement signal corresponding to the acceleration signal of 10A, produced by an anharmonic motion signal integrator 30.

FIG. 10D is a plot of an error corrected driving force signal corresponding to the driving-point motion signals of FIGS. 10A-C, showing the swept-frequency force applied to the soil by the seismic vibrator in the test described in Example 1.

FIG. 11A shows a segment of the driving force signal of FIG. 10D compared to a best-fit force synthesized from the parameter coefficients of a linear-system solution based on Model A, illustrating goodness-of fit for a linear model.

FIG. 11B shows the same driving force as FIG. 11A, compared to a best-fit force synthesized from a linear-system solution based on Model B, illustrating goodness-of-fit for a symmetric, nonlinear model.

FIG. 11C shows the same driving force as FIG. 11A, compared to a best-fit force synthesized from a linear-system solution based on Model C, illustrating goodness-of-fit for an asymmetric, nonlinear model with displacement-dependent damping.

FIG. 14A is a plot of first-order stiffness determined by the systems and methods of the present invention for a nonlinear elastic model, showing variation of stiffness of soil with time during the application of the force of FIG. 10D.

FIG. 14B is a plot of first-order viscosity, corresponding to the same driving force and same model as FIG. 14A, determined by the systems and methods of the present invention, showing large variation with time.

FIG. 14C is a plot of the ratio of stiffness to viscosity, based on data in FIGS. 14A-B, showing complicated variation with time.

DETAILED DESCRIPTION OF THE INVENTION

1. Terms Describing the Invention

Figure 2:
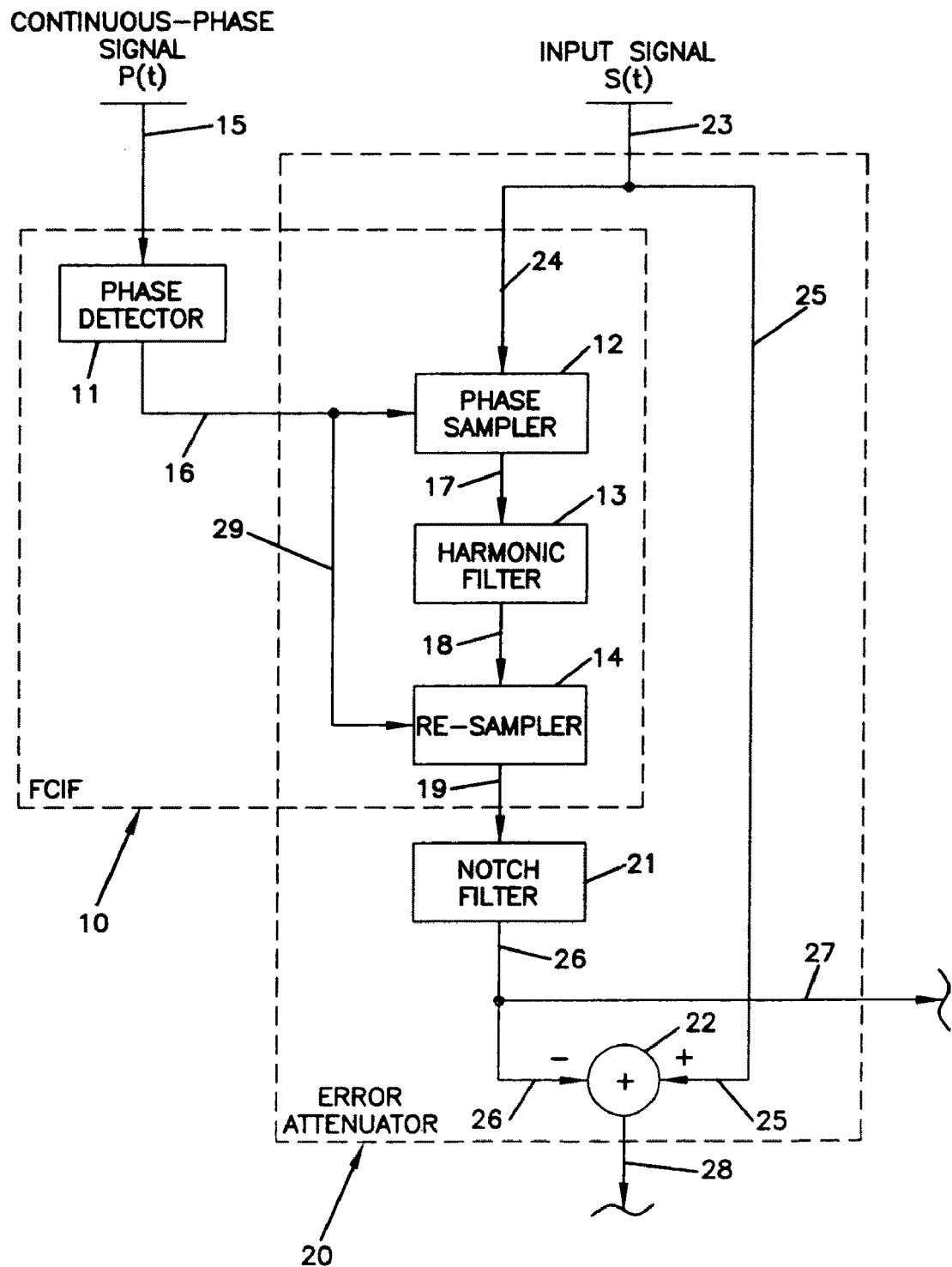
FIG. 2 is a schematic, diagrammatic view of a fractional-cycle-interval filter 10 and an error attenuator 20, both constructed in accordance with the present invention.

The terms used in the description of the present invention are understood to have the meanings described as follows:

actuator
  An actuator is an apparatus for generating a mechanical force, or for generating both a mechanical force and a mechanical motion. When the actuator is in contact with a substrate material, the force generated by the actuator acts upon the substrate material at a contact surface area. An actuator has a driving element which is an actuator element having a surface that engages the contact surface area of a substrate material upon which the actuator exerts a driving force. An actuator may be a static actuator or a dynamic actuator.

substrate material
  A substrate material is an elastic material upon which an actuator exerts a force. The actuator exerts the force on the substrate material at a contact surface area. The substrate material is not considered part of the actuator.

contact surface area
  A contact surface area is a surface area of the substrate material where the material is engaged by the actuator driving element. The actuator output force acts upon the substrate material at the contact surface area. The contact surface area has a defined surface area size. The defined surface area size of the contact surface area is the same as the defined surface area size of the driving element of the actuator. The points of the contact surface area are assumed to share substantially the same motion as the corresponding points on the driving element. All points of the contact surface area not necessarily in contact with the actuator driving element, but some portion of the contact surface area of the substrate material is sufficiently engaged by the actuator to exert a driving force on the substrate material. The contact surface area of the substrate material may be an exterior surface area of a body of the material, or it may be a surface area of a borehole or other excavation or cavity within the interior of the body of the substrate material.

dynamic force
  A dynamic force is a mechanical force that changes with time. For the purposes of the present invention, a dynamic force means a deforming force that varies with time such that the net force cancels out over the time period of the application of the force, such that when the dynamic force is removed, there remains no substantial net velocity or net acceleration of the body of material upon which the force acts. The dynamic force comprises one or more of the following component frequencies: a single frequency component, a continuous range of frequencies, a set of distinct frequencies, a set of distinct frequency ranges, a superposition of a plurality of frequency components, or combinations thereof. A swept-frequency force, an impulse force, a pseudo-random frequency force, and a noise burst force are kinds of dynamic forces.

driving force
  A driving force comprises a dynamic force exerted by an actuator on a substrate material at a contact surface area. The driving force is a vector force having a magnitude, a direction, and a point of application. The direction of the driving force comprises six degrees of freedom: a normal force component, two orthogonal shear force components, a torsional force component, and two orthogonal rocking force components. A normal force is a force acting in the direction perpendicular to the contact surface area. A shear force is a force acting in the direction parallel to the contact surface area. A torsional force is a rotational force acting around an axis perpendicular to the contact surface area. A rocking force is a rotational force acting around an axis parallel to the contact surface area. The driving force comprises a combination of one or more of the six component forces. A combination driving force can be separated into individual component forces representative of the separate components of normal, shear, torsion, and rocking. The driving force may also be expressed as a driving pressure or driving stress by dividing the magnitude of the driving force by the defined surface area size of the contact surface area to produce a value representative of pressure or stress in terms of force per unit area.

The driving force of the driving element acting on the substrate material is equal and opposite to the force of the substrate material acting on the driving element. Therefore the force of the substrate material acting on the driving element is classified herein as a particular embodiment of a driving force, wherein the driving force is scaled by a negative scale factor.

The point of application of a driving force is a driving point.

A driving force signal is a signal representative of the driving force.

driving point

The terms "driving point" and "driving-point" describe the location of the point of application where a driving force acts on a substrate material. The driving point is the contact surface area where an actuator exerts a driving force on a substrate material. The driving point is not a single point per se; the driving point has a defined surface area size corresponding to the defined surface area size of the driving element of the actuator. The driving point is also called a driving-point location. The driving-point location is the location of the driving point on or within a body of the substrate material.

source location

In one embodiment, a driving-point location is also known in the art as a source location.

driving-point motion

A driving-point motion is a motion of a driving point where a corresponding driving force is exerted by an actuator, wherein the motion is generated by the action of the corresponding driving force. The driving point motion and the corresponding driving force are determined at substantially the same location and time, the location being the contact surface area of the substrate material, and the time being the time the driving force is exerted. The driving-point motion is a deformation motion, representing the deformation of the substrate material in response to the driving force. A driving-point motion is a vector function of time, having a magnitude and a direction, comprising the vector sum of any one or more of six components of motion: three orthogonal displacement components and three orthogonal rotational components.

A driving-point motion comprises any of the following kinds of driving-point motion: a driving-point acceleration, a driving-point velocity, a driving-point displacement, or a driving-point rotation.

Any one of three distinct driving-point motions—acceleration, velocity, or displacement—may be used to determine the other two by appropriate integration or differentiation, as is well known in the art. Therefore in one embodiment a driving-point motion can be represented by an expression of any one of three distinct driving-point motions—a driving-point acceleration, a driving-point velocity, or a driving-point displacement.

The driving-point displacement is a deformation displacement, which is the distance the contact surface area is displaced from an initial position relative to the body of substrate material. The initial position is typically the position of the contact surface area when substantially at rest prior to the application of the driving force. The driving-point displacement is representative of the deformation of the substrate material caused by the corresponding driving force. The driving-point displacement comprises a vector sum of a normal displacement component, a shear displacement component in a first shear direction, a second shear displacement component in a second shear direction perpendicular to the first shear direction, or any combination thereof. A driving-point displacement that is a combination of more than one component of motion can be separated into the individual displacement components, and each separate displacement component can be analyzed independently as a single-component driving-point displacement.

The driving-point velocity is a kind of driving-point motion. The driving-point velocity is the time rate of change in the driving-point displacement.

The driving-point acceleration is a kind of driving-point motion. The driving-point acceleration is the time rate of change in the driving-point velocity.

If a deformation motion of the substrate material is determined at a location substantially different from the contact surface area where the driving force is exerted, or at a time substantially after the time the corresponding driving force is exerted, the motion is described by the terms "transfer-point motion" and "transfer-point response". The transfer-point motion and transfer-point response comprise an elastic disturbance motion which has traveled some distance from the driving-point through the elastic material before it is measured.

driving-point response

A driving-point response comprises a driving-point motion and the corresponding driving force. In one embodiment, the driving-point response is represented by a set of two distinct signals, the set comprising a driving force signal representative of the driving force, and a driving-point motion signal representative the driving-point motion corresponding to the driving force.

anharmonic

An anharmonic signal comprises a superposition of a plurality of harmonic frequency components at harmonics of a fundamental, periodic component of the signal. An anharmonic signal is periodic, but is not sinusoidal.

Any force, motion, or signal which comprises a superposition of a plurality of harmonic frequency components at harmonics of a fundamental, periodic component can be classified as anharmonic.

The driving-point response of a nonlinear elastic material in response to a periodic driving force comprises an anharmonic response, wherein the driving-point motion is an anharmonic motion comprising a superposition of a plurality of harmonic frequency components at harmonics of the frequency components of the corresponding driving force.

motion

A motion is a mechanical motion comprising an acceleration, a velocity, a displacement, or a rotation of a particle's location in space as a function of time. The displacement is the distance the particle is displaced from an initial position, the initial position typically being the particle's position at rest. The velocity is the time rate of change in the displacement. The acceleration is the time rate of change in the velocity. A motion is a vector function of time, having a magnitude and a direction.

driving element

A driving element is an element of an actuator. The driving element is the element having a surface that engages the contact surface area of a substrate material upon which the actuator exerts a driving force. The driving element exerts the driving force onto the substrate material at the contact surface area. The driving element has a defined surface area size which is the surface area size of the contact surface area engaged by the driving element. The defined surface area size of the driving element is equivalent to the defined surface area size of the contact surface area of the substrate material. The contact surface of the driving element is typically assumed to move as a substantially rigid body, although some flexing of the driving element can occur.

When the driving element exerts a driving force onto the contact surface area of an elastic material, the driving-point motion of the elastic material is coupled to the motion of the driving element. The driving-point motion of the contact surface area of the substrate material is assumed to be substantially the same motion as the motion of the driving element, unless otherwise noted herein. The degree of similarity between the motion of the driving element and the driving-point motion of the elastic material depends on the degree of the coupling. The coupling of the driving element to the contact surface area may be complete or partial.

In one embodiment the driving element can be rigidly attached to the substrate material by an attachment means.

In another embodiment the driving element can be held in contact with a surface of the substrate material by application of a static compressive force acting substantially independently from the actuator driving force. In this embodiment, the total force the driving element exerts on the contact surface area is the sum of the static force plus the actuator driving force acting on the contact surface area. When the sum of the static compressive force and the actuator driving force is a sum of zero force, the actuator driving element may possibly loose contact with the substrate material, and the motion of the driving element may become decoupled from the motion of the substrate material. The static force is also known in the art as a "hold-down force" or a "hold-down weight". Depending on the degree of isolation of the baseplate from the hold-down mechanism, the motion of the driving element may be partially transferred to the hold-down mechanism, generating a dynamic component in the hold-down force. The dynamic force component produced by the hold-down mechanism comprises a component of the total driving force applied to the driving element. If the dynamic component of the hold-down force is substantial, it may be quantified and included as a component of the driving force. The static component of the hold-down force is not considered part of the driving force, and the driving force produces a driving-point response which is analyzed independently of the static hold-down force.

The driving element has a mechanical inertial mass. The driving element mass is the sum of the inertial mass of the driving element and the inertial mass of all other actuator elements rigidly attached to the driving element or contributing to the inertial resistance to acceleration of the driving element.

The driving element is also called a baseplate.

dynamic actuator

A dynamic actuator is an actuator that produces a dynamic driving force. A dynamic actuator exerts a dynamic driving force on a substrate material. A dynamic actuator may be controlled or uncontrolled. A controlled dynamic actuator has a control system for controlling the actuator output.

reciprocating actuator

A reciprocating actuator is a reaction-type dynamic actuator wherein the actuator output force is generated by reciprocating motion of a reaction-mass and a baseplate. The reaction-mass is an inertial mass driven by the actuator, the reciprocating motion of the reaction mass causing a reciprocating force to act upon the baseplate. The baseplate is the driving element of the reciprocating actuator. The relationship between the motion of the reaction mass and the motion of the baseplate is highly variable, and depends on various factors including but not limited to the response of the actuator drive means, the means used to couple the reaction mass to the baseplate, the frequency components of the motion, and the response of the substrate material.

The reaction-mass has an inertial mass. The inertial mass of the reaction-mass is the sum of the inertial mass of the reaction-mass element and the inertial mass of all other actuator elements rigidly attached to the reaction-mass element or contributing to the inertial resistance to acceleration of the reaction-mass.

relative displacement

Relative displacement is a representation of the displacement of the position of the reaction-mass relative to the position of the baseplate in a reciprocating actuator. In a reciprocating actuator, as the reaction-mass and the baseplate undergo reciprocating motions, the relative displacement is a measure of the separation distance between the reaction-mass and the baseplate while they are in motion referenced to the initial separation while at rest. The relative displacement is a kind of motion. A relative displacement signal is a signal representative of the relative displacement motions of a reciprocating actuator. A relative displacement signal is a kind of motion signal, and is a kind of actuator output.

servo-hydraulic actuator

A servo-hydraulic actuator is a reciprocating actuator wherein the motive force which drives the reciprocating motion of the reaction-mass and the baseplate is hydraulic pressure of a fluid controlled by a servo-valve.

electro-dynamic actuator

An electro-dynamic actuator is a reciprocating actuator wherein the motive force which drives the reciprocating motion of the reaction-mass and the baseplate is an electromagnetic force.

seismic vibrator

A seismic vibrator is a controlled reciprocating actuator as commonly used in the geophysical industry. In one embodiment, a seismic vibrator is a servo-hydraulic actuator. A "shear-wave vibrator" comprises an embodiment of a seismic vibrator with the actuator oriented to generate a shear force. A "P-wave vibrator" comprises an embodiment of a seismic vibrator with the actuator oriented to generate a normal force. A seismic vibrator is also known in the art as simply a vibrator. The terms "seismic vibrator" and "vibrator" are also used in the art to refer to the actuator together with a vehicle on which the actuator is mounted. For the purposes of the present invention, the term "seismic vibrator" and "vibrator" refer to the actuator.

marine vibrator

A marine vibrator is a dynamic actuator as commonly used in the geophysical industry for generating a dynamic driving force in a body of water.

rotating mass actuator

An rotating mass actuator is a dynamic actuator wherein the actuator output is generated by rotational motion of one or more eccentric masses. The centripetal acceleration of the rotating eccentric mass generates an oscillatory output force, oscillating with the period of rotation of the eccentric mass. One or more rotating masses can be used, and the actuator output force is the vector sum of the output force of each rotating mass. When more than one rotating mass is used, the axis of rotation of each mass can be different in orientation, location, or combinations thereof. In one embodiment of a rotating mass actuator, two eccentric masses with parallel axes of rotation are rotated at equal rates in opposite directions, thereby generating a net output force oscillation that is polarized, the polarization depending on the relative phase of rotation of the two masses. An orbital vibrator is an embodiment of a rotating mass actuator.

piezoelectric actuator

A piezoelectric actuator is a dynamic actuator for generating a driving force at sonic and ultrasonic frequencies. The piezoelectric actuator comprises a piezoelectric material which is dynamically deformed by an electric signal to produce an output force. One embodiment of a piezoelectric actuator is an ultrasound transducer.

impulse actuator

An impulse actuator is a dynamic actuator which generates an impulsive driving force. In one embodiment the impulsive force is generated by an impulse element acting upon a separate baseplate element, and the driving force is exerted on the substrate material by the baseplate. In another embodiment the impulse element exerts the driving force directly onto the substrate material. A weight drop actuator, an accelerated weight drop actuator, and an electromagnetic impulse actuator are embodiments of impulse actuators. An impulse actuator can be provided with sensing means to measure the driving force generated by the impulse.

actuator output

Actuator output is a representation of a motion or a force generated by an actuator. An actuator output comprises any of various measures representative of the motion, force, pressure, or stress generated by the actuator or elements thereof, including but not limited to the following:
  the driving force exerted on the substrate material by the actuator driving element;
  the force exerted by the substrate material acting on the actuator driving element;
  the reaction-mass acceleration, velocity, or displacement for a reciprocating actuator;
  the driving element acceleration, velocity, or displacement;
  the driving-point acceleration, velocity, or displacement;
  weighted-sum force, which is sum of the baseplate acceleration multiplied by its mass and the reaction-mass acceleration multiplied by its mass;
  the pressure exerted by the actuator driving element acting on the substrate material;
  the stress exerted by the actuator driving element acting on the substrate material;
  the relative displacement, relative velocity, or relative acceleration of the reaction-mass relative to the baseplate for a reciprocating actuator.

control system

An actuator control system is a means to control the actuator output. A control system comprises a means to drive the actuator in a controlled manner such that the actuator output is substantially similar to a reference signal, wherein substantially similar means as similar as possible within the capability of the control system. The actuator control system may include phase control, amplitude control, or both phase and amplitude control. If phase control is used, the actuator is controlled such that the phase of the chosen actuator output is similar to the phase of the reference signal, where phase similarity means a substantially constant phase difference between the chosen actuator output and the reference signal at a chosen value of the phase difference. If amplitude control is used, the actuator is controlled such that the amplitude of the actuator output is proportional to the amplitude of the reference signal.

The degree of similarity between the reference signal and the actuator output depends on the capability of the actuator and the capability of the actuator control system. The degree of similarity between the reference signal and the actuator output may be expressed in various ways, including but not limited to a phase difference, a time delay, an amplitude ratio, or a spectral density difference.

Any one of several different measures of the actuator output may be chosen for controlling the actuator.

reference signal:

A reference signal is a signal used in an actuator control system for controlling a dynamic actuator such that the actuator output is controlled to be similar to the reference signal. The reference signal is representative of the phase and/or relative amplitude which are desired to be produced by the actuator in the actuator output.

A driving force reference signal is a reference signal used for controlling the driving-force output of an actuator.

In one embodiment, the reference signal is a drive signal that controls the actuator directly. In another embodiment, the actuator has a control system that generates a drive signal that is distinct from the reference signal, adjusting the drive signal to achieve improved similarity of the actuator output relative to the reference signal. The actuator control system may include a feedback loop that compares the reference signal to a feedback signal representative of the actual measured output of the actuator, and adjusts the actuator drive to optimize the similarity of the output compared to the reference signal. The feedback loop may comprise a phase-lock loop, an amplitude control loop, or both a phase-lock loop and an amplitude control loop.

Continuous-phase signals are commonly used as reference signals to control dynamic actuators.

One embodiment of a reference signal is a continuous-phase reference signal, which is a continuous-phase signal used as a reference signal. Another embodiment of a reference signal is a continuous-phase reference signal comprising a range of frequencies. The range of frequencies is chosen to produce an actuator output that meets the needs of the particular use.

Embodiments of some commonly used reference signals are as follows:
  a swept-frequency signal;
  a continuous-phase signal defined by a linear function of frequency;
  a continuous-phase signal defined by an exponential function of frequency;
  a continuous-phase signal defined by a logarithmic function of frequency;
  a continuous-phase signal defined by a polynomial function of frequency; and continuous-phase signals defined by a pseudo-random function.

The reference signal is also known in the art as a pilot signal.

It is well known to those skilled in the art that there are other embodiments of a reference signal that may be used for controlling an actuator.

continuous-phase signal:

A continuous-phase signal is a signal that may be represented as a sinusoidal function of phase, wherein the phase is a continuous function of time. The continuous-phase signal is scaled by an amplitude envelope function that may vary with time. A continuous-phase signal can be expressed mathematically as follows:

$$P(t) = A(t)e^{i(\phi(t))} \quad (1)$$

where
P(t) represents a continuous-phase signal;
A(t) represents the amplitude envelope as a function of time;
φ(t) represents the phase function of the continuous-phase signal, represented as angular phase (in radians) as a continuous function of time;
t time;
$i = \sqrt{-1}$;
$e^{i\theta} = \cos\theta + i\sin\theta$.

The angular frequency of the continuous-phase signal is the first derivative of the angular phase function:

$$\omega(t) = d\phi(t)/dt \quad (2)$$

$$f(t) = \omega(t)/2\pi \quad (3)$$

where
ω(t)=angular frequency as a function of time (radians per second)
f(t)=frequency as a function of time (cycles per second)

Because frequency is the time derivative of phase, the phase function φ(t) may be determined from the integral of a frequency function:

$$\phi(t) = 2\pi \int f(t)dt \quad (4)$$

Given any integrable, continuous function of frequency f(t), a continuous-phase signal may be produced from the angular phase function φ(t) so determined. Thus one embodiment of a continuous-phase signal P(t) may be described by a continuous phase function φ(t) and a continuous frequency function f(t).

In another embodiment of a continuous-phase signal, the continuous function of phase φ(t) may have a discontinuous first derivative, so that the frequency function f(t) is discontinuous. As long as the phase function φ(t) is continuous, it need not necessarily have continuous derivatives to be encompassed by my definition of a continuous-phase signal. A continuous-phase signal based on an angular phase function φ(t) that has a discontinuous first derivative will have a discontinuous frequency function. A pseudo-random frequency signal is a particular embodiment of a continuous-phase signal that can be described by an angular phase function φ(t) that in some particular cases may have a discontinuous first derivative.

If the continuous function of phase φ(t) is increasing monotonically, the first derivative will be greater than zero for all values of time t, and therefore the frequency function of the continuous-phase signal P(t) will be a positive frequency for all values of time t. If the continuous function of phase φ(t) is decreasing monotonically, the first derivative will be less than zero for all values of time t, and therefore the frequency function of the continuous-phase signal P(t) will be a negative frequency for all values of t.

A continuous-phase signal has various useful properties. Because the phase function φ(t) has a single value at any point in time, the continuous-phase signal has a single "instantaneous phase" value at each point in time. If the phase function φ(t) has a continuous derivative, the derivative of the phase function φ(t) is also single valued at any point in time, and the continuous-phase signal has a single "instantaneous frequency" value dφ(t)/dt at each point in time. If the amplitude envelope function A(t) varies with time, the variable amplitude results in amplitude modulation of the continuous-phase signal. It is known in the art that amplitude modulation introduces side-band frequencies above and below the instantaneous frequency dφ(t)/dt. Thus in one embodiment of a continuous-phase signal with a variable amplitude envelope function A(t), the instantaneous frequency may be considered to be effectively a "carrier" frequency of an amplitude modulated signal comprising one or more sideband frequencies.

Another useful property is that a continuous-phase signal is useful for representing the motion of real objects. Real motions are continuous in phase. For example, a motion of an actuator can be represented accurately by a continuous-phase signal. Thus a continuous-phase signal is useful as a reference signal for controlling an actuator.

From this definition, it will be apparent to one skilled in the art that a continuous-phase signal may comprise a single frequency, a range of frequencies, a set of distinct frequencies, a set of distinct frequency ranges, or a combination thereof.

One embodiment of a continuous-phase signal comprises an analog signal representative of the real part of the complex-valued continuous-phase signal P(t) of equation (1). Another embodiment is the digital sample values of a digital signal representative of the real part of P(t). Another embodiment of a continuous-phase signal is a parametric representation, as parameter values defining an amplitude function and a phase function or a frequency function that define the signal. Yet another embodiment of a continuous-phase signal is an analytic signal consisting of two distinct signals: one signal being a representation of the real part of the continuous-phase signal, the other signal being a representation of the imaginary part of the continuous-phase signal. The imaginary part of the continuous-phase signal comprises the Hilbert transform of the real part of the continuous phase signal. The two signals of an analytic signal comprise a Hilbert transform pair.

It will be apparent to one skilled in the art that there are other equivalent representations and embodiments of a continuous-phase signal, and other useful properties of a continuous-phase signal.

A phase reference signal is a continuous-phase signal provided to a fractional-cycle-interval filter as a phase reference.

sweep, swept-frequency, up-sweep, down-sweep, chirp:

A commonly used embodiment of a reference signal is a continuous-phase signal defined by a monotonic function of frequency comprising a range of frequencies. A reference signal based on this type of frequency function is called a "sweep", a "chirp", or a "swept-frequency" function or signal. If the function of frequency is monotonically increasing, the sweep is known as an up-sweep. If the function of frequency is monotonically decreasing, the sweep is known as a down-sweep. The terms "sweep" and "swept-frequency" are also used to refer to any signal or function representative of a continuous-phase function having a monotonic function of frequency. The actuator output is also sometimes referred to in the art as a sweep.

fractional-cycle interval:

A cycle can be divided evenly into equal intervals of phase called fractional-cycle intervals, such that there are an integer number of fractional-cycle-intervals per cycle. A fractional-cycle interval is a phase interval that is an integer-reciprocal fraction of one cycle. Dividing a cycle into N equal fractional-cycle intervals may be described by the following mathematical expressions:

$$\Delta\varphi = \frac{2\pi}{N} \quad (5)$$

$$\varphi_k = k\Delta\varphi \quad (6)$$
$$= k\frac{2\pi}{N},$$
$$k = 0, 1, 2, 3, \ldots$$

where
$\Delta\phi$ is the size of the fractional-cycle interval equal to one-$N^{th}$ of one cycle, expressed as a phase-interval in radians;
$\phi_k$ is the phase value of the ending point of the $k^{th}$ interval;
N is the number of intervals per cycle.

harmonic

A harmonic is a positive integer multiple of a fundamental frequency, the fundamental frequency being the first harmonic. The term "harmonics" refers to a set of harmonic frequencies all based on the same fundamental frequency; "harmonics" may include the fundamental frequency in the set as the first harmonic.

integration signal

An integration signal is a signal produced by integration of another signal over an integration interval.

2. Elastic Materials and Properties

A physical body of material can be deformed by applying external forces to a surface area of the body of material. The external deforming forces are opposed by internal forces of the material that resist the deformation. When the external forces are removed, the material tends to recover and return to its original size and shape. The deformation is a change in size, shape, or both size and shape. A solid material resists deformation in size and shape; a fluid material resists changes in size (volume) but not changes in shape. This property of resisting deformation and recovering after being deformed is called elasticity. For a fluid, it is also known as incompressibility. An elastic material returns to its original size and shape after the external deforming forces are removed.

If the deforming forces are sufficiently large, the material may not completely recover and may remain deformed after the external forces are removed. The greatest applied stress which does not cause permanent deformation is known as the elastic limit of the material. Many materials including rocks and soil can be considered elastic for stresses that are within the elastic limit of the material (W. M. Telford et al., 1990, *Applied Geophysics Second Edition*, Cambridge University Press, p. 140).

Most real materials are not perfectly elastic. When external deforming forces are removed, the material may return to its original size and shape over some period of time, but not instantaneously. The delay in the elastic response is due to a property of the material which is referred to as viscosity. The delay in the elastic response is also characterized by dissipation of the energy of the dynamic deforming forces, and it produces a damping effect on free vibrations of the material by dissipating the elastic energy.

It should be noted that the delay in elastic response and dissipation in many materials is not considered to be physically caused by a true viscous behavior of the material. The terms "viscosity" and "viscous" are used herein for convenience to refer generally to dissipation or damping effects of vibrations in elastic material.

One form of elastic energy dissipation comprises radiation of elastic waves. For a large body of elastic material a dynamic deforming force produces elastic waves which propagate through the material and along the surface of the material, radiated from the area where the deforming force is exerted. The propagating elastic waves transfer energy from the deforming force into the body of the material away from the area where the deforming force is exerted. This dissipation of energy by radiation of elastic waves produces a damping effect on the elastic response at the area where the deforming force is exerted. For a semi-infinite body of material, the radiation of elastic-waves represents a significant loss of energy and a significant damping effect on the elastic response. This damping effect produced by radiation of elastic waves is called geometrical damping or radiation damping.

Another form of elastic energy dissipation is due to internal properties of the material which absorb the elastic energy. Absorption of elastic energy by a material is sometimes called internal friction. The internal absorption of elastic energy results in a damping effect on the elastic response to a deforming force, and it is called internal damping or material damping.

Therefore, the property called viscosity as used herein comprises a combination of two general forms of dissipation: radiation damping and material damping.

Elasticity may be described as resistance to a deformation. An elastic force is an internal force exerted by a body of elastic material which opposes a deformation. A linear elastic force is a linear function of the deformation; a nonlinear elastic force is a nonlinear function of the deformation. One measure of the degree of resistance to deformation comprises an elastic property of the material called stiffness. Another measure is called compliance, which comprises the reciprocal of stiffness. For a linear elastic force in one dimension, stiffness comprises the proportionality of a deforming force to the corresponding deformation displacement.

The coefficient of proportionality of a linear elastic force to the corresponding deformation is referred to herein a first-order stiffness coefficient or a first-order coefficient of stiffness. For a nonlinear elastic force, stiffness comprises more than one coefficient. The coefficients of nonlinear stiffness are referred to herein by the degree of nonlinearity, for example second-order stiffness coefficient, third-order stiffness coefficient, etc.

It is well known that stiffness can be expressed in terms of the proportionality of force to displacement, or in terms of the proportionality of stress to strain. The two forms of expressing stiffness are related by the area over which the force acts, and stiffness can be converted from one form of expression to the other. It is also well known that stiffness can be represented in a generalized form by a 6×6 tensor relating the six components of stress to the six components of strain.

Viscosity may be described as resistance to a change in deformation. A viscous force is an internal force exerted by a body of material which opposes a change in deformation. A linear viscous force is a linear function of the rate of change of the deformation; a nonlinear viscous force is a nonlinear function of the rate of change of the deformation. A viscous force produces a delayed response in an elastic force. Because of the delay, the deformation is not in phase with the applied deforming force, and the viscosity may be characterized by a phase lag and/or time delay between the deforming force and the deformation.

Viscosity is quantified herein by coefficients of viscosity, comprising the relationship of the deforming force to the time rate of change in the corresponding deformation. For a linear viscous force, the coefficient of viscosity comprises the proportionality of the deforming force to the time-rate of change in deformation. The linear coefficient of viscosity called herein a first-order viscosity coefficient. For a nonlinear viscous force, there are corresponding nonlinear coefficients called second-order viscosity coefficient, third-order viscosity coefficient, etc. The viscosity coefficients are also sometimes called damping coefficients.

An elastic material may be a linear elastic material or a nonlinear elastic material. A linear elastic material responds to a deforming force with an linear elastic force and a linear viscous force. A nonlinear elastic material responds to a deforming force with a nonlinear elastic force, a nonlinear viscous force, or a combination thereof. Most real elastic materials are nonlinear. However, for a sufficiently small deforming force producing a small deformation, many real materials approximate a linear elastic material. The linear approximation is termed a small-amplitude approximation. A larger deforming force may exceed the small-amplitude approximation limit without exceeding the elastic limit of the elastic material.

The deforming force acting on a body of elastic material may be a static force or a dynamic force. A dynamic force, called herein a driving force, produces motion of the elastic material where the force is exerted. Because the driving-point is in motion, the motion is resisted by the inertia of the mass density of the elastic material. The inertial resistance may be expressed as an inertial force component of the response of an elastic material to a dynamic driving force.

A driving force acting on a contact surface area of an elastic material deforms the elastic material, and the elastic material responds with internal elastic forces that resist the deformation and internal viscous forces that resist the change in deformation. Because the driving force is dynamic, the deformation changes with time, which means that the contact surface area is in motion in response to the driving force. The changing motion comprises accelerations of the contact surface area, and the accelerations of the contact surface area indicate that there is a net unbalanced force acting on the contact surface area. The contact surface area undergoes acceleration motions because the internal viscous force and elastic force do not exactly balance the driving force being exerted. Therefore, the inertial mass density is a property of an elastic material which influences the response of the elastic material to a dynamic driving force.

An inertial force component of a driving-point response represents the net unbalanced force which produces an acceleration motion of the deformation of the material in response to the dynamic force.

It is also noted that the driving-point response of an elastic material to a dynamic driving force at low-frequencies substantially below the natural frequency is known in the art as a stiffness-dominated response; at frequencies near the natural frequency is known as a viscosity-dominated response; and at frequencies substantially higher than the natural frequency is known as a mass-dominated response. This classification applies to both linear and nonlinear materials and models, and to both small-amplitude and large-amplitude driving forces.

An elastic material initially at rest responds to the initiation of a dynamic deforming force with an initial response comprising component frequencies at one or more natural modal frequencies, along with component frequencies matching the component frequencies of the driving force. The component of the initial response at the natural modal frequencies is known as a transient response. As the dynamic deforming force continues to be exerted after initiation, the amplitude of the transient response dissipates over time, and the remaining response comprises component frequencies corresponding to the component frequencies of the driving force. After sufficient time when the transient response has decreased to substantially negligible amplitude, the remaining response is known as a steady-state response. The initial response comprises a superposition of a transient response and a steady-state response.

The response of a nonlinear elastic material to a driving force which exceeds the small-amplitude approximation limit is a nonlinear, anharmonic response (A. P. French, 1971, *Vibrations and Waves*, W.W. Norton & Co., p. 110-112). The nonlinear, anharmonic response comprises anharmonic driving-point motions of the contact surface area where the driving force is exerted, and also comprises either a nonlinear elastic force component, a nonlinear viscous force component, or a combination thereof. The anharmonic driving-point motions comprise a superposition of a set of component frequencies at harmonics of the component frequencies of the driving force. The fundamental frequency component of the anharmonic response is the same as the fundamental frequency component of the driving force, so the anharmonic response has a fundamental period which is the same as the fundamental period of the driving force. The occurrence of anharmonic frequency components is characteristic of the driving-point response of a nonlinear elastic material, and the amplitude and phase relationships of the harmonic frequency components of the anharmonic driving-point response represent information about the nonlinear elastic properties of the material.

For example, Bratu has shown that an elastic material having linear elasticity and nonlinear viscosity has an anharmonic response comprising odd-numbered harmonic multiples of the driving force, but a material having nonlinear elasticity and linear viscosity has an anharmonic response comprising both odd and even-numbered harmonics. He concludes that analyzing the information represented by the harmonic components is important for evaluating the behavior of nonlinear materials (P. Bratu, 2003, "Dynamic Response of Nonlinear Systems Under Stationary Harmonic Excitation", Facta Universitatis: Mechanics, Automatic Control and Robotics, vol. 3, no. 15, pp. 1073-1076).

In summary, the response of an elastic material to a dynamic driving force comprises: a transient response, a steady-state response, a linear or nonlinear elastic force component, a linear or nonlinear viscous force component, an inertial force component, an anharmonic response, or combinations thereof. The response may be described as being one or more of the following: either linear or nonlinear; anharmonic; either stiffness-dominated, viscosity-dominated, or mass-dominated; either within or exceeding the small-amplitude approximation limit; and either within or exceeding the elastic limit. The response of a body of elastic material to a deforming force may be described by properties of the material called elastic properties which are representative of the material's elasticity, viscosity, inertial mass density, or combinations thereof. The elastic properties may be expressed in various ways well known in the art, including but not limited to stiffness, viscosity, inertial mass density, elastic moduli, elastic wave speed, Young's modulus, bulk modulus, shear modulus, Lame constant lambda, Poisson's ratio, P-wave speed, S-wave speed, ratio of P-wave speed to S-wave speed, and absorption factors.

The dynamic elastic properties of an isotropic, linear, perfectly elastic material may be fully described by any three independent properties. There are more than three forms of expression for representing elastic properties; these various representations are interrelated and can be converted from one form to another by well known relationships (R. E. Sheriff, 2002, *Encyclopedic Dictionary of Applied Geophysics, Fourth Edition*, Society of Exploration Geophysicists, p. 115-116). Three independent properties which are often used in the art are shear modulus, Poisson's ratio, and density; but these three properties can be converted to an equivalent representation by a different combination of three independent elastic properties.

Several methods are known in the art for determining elastic properties by exerting a deforming force on a body of elastic material, measuring the response of the material, and analyzing the response to determine the elastic properties. The methods may be classified as static, dynamic, driving-point, or transfer-point.

In a static method, the deforming force is a static force which is substantially constant, and the response may be characterized by analyzing a creep function or by analyzing deformation or strain. In a dynamic method, the deforming force is a dynamic force which changes substantially in magnitude over a period substantially shorter than the duration of the measurements. The response to a dynamic force comprises dynamic motions of the material where the force is exerted, and the dynamic motions are analyzed in relation to the exerted force to characterize the elastic properties.

In a driving-point method, the response to a dynamic force is measured at substantially the same point where the force is exerted, and is measured substantially synchronously with the exerted force. In a transfer-point method, the response to a dynamic force is measured on the body of elastic material at a substantially different location from the point where the force is exerted, or at a time substantially after the force is exerted, or a combination thereof. In other words, a transfer-point method measures an elastic deformation disturbance which has traveled some distance through the elastic material. A driving-point method measures the deformation motions at the location where they are generated.

A typical method known in the art for analyzing a dynamic driving-point response is by analyzing a frequency response in the complex frequency domain using methods generally known as Laplace transform methods. Implicit assumptions in Laplace transform methods are that the response being analyzed represents a steady-state response, and that the response includes only the same frequency components that are present in the driving force (i.e. the response is assumed to not be anharmonic). Therefore, it is common practice to use a driving force within the small-amplitude approximation limit, and to use a tracking filter to attenuate the transient response and/or the anharmonic frequency components having frequencies higher than the fundamental frequency.

However, the transient response and the anharmonic response represent useful information about the elastic properties of real, nonlinear elastic material, so attenuating these components causes a loss of useful information. The transient components and anharmonic frequency components can represent a substantial portion of the total elastic energy in the driving-point response, and attenuating these components results in a misrepresentation of the relationship of the driving-force to the response. Attenuating the anharmonic frequency components higher than the fundamental frequency results in an estimate of elastic properties that tends to substantially underestimate stiffness.

Relying on the small-amplitude approximation restricts the driving force amplitudes and actuator types which may be used. In order to be able use large driving forces and large actuators, the present invention provides methods that do not rely on the small-amplitude approximation. For example, in the geophysical industry powerful actuators producing large amplitude driving forces are used for seismic imaging of the earth, using driving force amplitudes substantially exceeding the small-amplitude approximation limit. One objective of the present invention is to analyze large amplitude driving-point motions produced by seismic vibrators to determine elastic properties of the earth at the location of the applied force, without relying on the small-amplitude approximation, so that the elastic properties so determined are more meaningfully representative of the actual elastic properties.

The present invention provides systems and methods for using the full information represented by the transient component, the steady-state component, the nonlinear response, and the anharmonic response of a real, nonlinear elastic material, to produce an improved estimate of elastic properties of the elastic material. The systems and methods of the present invention comprise analysis of a driving-point response of an elastic material in response to a dynamic driving force exerted by a dynamic actuator on a contact surface area of the elastic material.

Objects of the Invention

It is an object of the present invention to determine one or more elastic properties of an elastic material by analyzing a driving-point response of the elastic material, wherein the driving-point response comprises a driving-point motion produced in response to a driving force exerted by a dynamic actuator on a contact surface area of the elastic material.

It is an object of the present invention to determine the elastic properties by analyzing the driving-point response wherein the driving-point response comprises any one or more of the following:

a linear driving-point response within the small-amplitude approximation;

a nonlinear driving-point response produced by a driving force which substantially exceeds the small-amplitude approximation limit of the elastic material, to determine linear and/or nonlinear elastic properties;

an anharmonic driving-point response comprising a superposition of a plurality of harmonic frequency components at harmonics of the frequency components of the driving force;

a stiffness-dominated, viscosity-dominated, or mass-dominated response, and combinations thereof, produced by a driving force comprising a range of frequencies substantially lower-than, substantially near, and/or substantially higher than the natural frequency of the elastic material;

a superposition of a transient response and a steady-state response;

a driving-point response of an in-situ material or of an isolated sample of material.

It is an object of the present invention to determine one or more linear elastic properties representative of a linear, small-amplitude approximation response by analyzing a nonlinear, anharmonic driving-point response produced by a driving force which substantially exceeds the small-amplitude approximation limit of a nonlinear elastic material.

It is an object of the present invention to determine the variation of elastic properties as a function of time during the application of the driving force, to detect changes in the properties of the material caused by the driving force, and to determine variation in the properties as a function of frequency.

It is an object of the present invention to determine the elastic properties by forming a system of linear equations representative of the driving-point response, and to solve the system of linear equations to determine a best-fit solution representative of the elastic properties.

It is an object of the present invention to solve the system of linear equations for overdetermined systems, underdetermined systems, and/or ill-conditioned systems, by a method which provides control of nullspace components of the solution.

It is an object of the present invention to take advantage of anharmonic characteristics of the driving-point motions of a nonlinear elastic material to estimate and attenuate broadband errors in driving-point motion signals and in driving force signals—including measurement errors and/or broadband integration errors—while substantially preserving the phase relationships and the amplitude relationships of the plurality of harmonic components that are representative of the anharmonic response of the elastic material.

It is an objective of the present invention to estimate a spectral amplitude and a spectral phase function of an anharmonic signal comprising driving-point motion signals and actuator output signals at frequencies that are harmonics of a known continuous-phase reference signal.

3. Determining Elastic Properties by Analyzing a Driving-Point Response

In the present invention, I disclose systems and methods for determining one or more elastic properties of an elastic material by analyzing a driving-point response of the elastic material.

Analyzing the driving-point response comprises analyzing the relationships between two or more distinct driving-point response signals that are representative of the driving-point response of the elastic material—the distinct driving-point response signals being a driving force signal, a driving-point acceleration signal, a driving-point velocity signal, or a driving-point displacement signal.

Analyzing the driving-point response comprises determining a set of coefficients that best fit a system of linear equations, the terms of the linear equations corresponding to the terms of a differential equation, the differential equation being representative of a model of the motion of an elastic material, and the coefficients so determined being elastic coefficients representative of one or more elastic properties of the elastic material. The set of best-fit coefficients are determined by solving the system of linear equations.

In one embodiment, solving the system of linear equations comprises determining a singular value decomposition of a design matrix representing the system of linear equations, the elements of the design matrix representing the terms of the linear equations. The value of each of the elements of the design matrix is determined from the value of one or more of the distinct driving-point response signals, according to the terms of the differential equation. The singular value decomposition is adjusted to eliminate nearly singular values which are substantially representative of a nullspace of the system of linear equations. The adjusted singular value decomposition is used to determine the solution set of best-fit parameter coefficients that are representative of one or more of the elastic properties of the elastic material.

The present invention provides a method for determining one or more elastic properties of an elastic material by analyzing a driving-point response of the elastic material, the method comprising:
  (aa) forming a system of linear equations representative of the driving-point response of the elastic material, the terms of the linear equations corresponding to the terms of a differential equation, the differential equation being representative of a model of the driving-point response of the elastic material, and each equation in the system of linear equations representing the differential equation evaluated at a distinct point in time, the system of equations so formed being thereby representative of the differential equation evaluated at a set of distinct points in time; and
  (bb) solving the system of linear equations so formed, to determine a set of parameter coefficients which represent a best-fit solution of the system of linear equations.

The best-fit solution in step (bb) is a set of parameter coefficients which are representative of one or more elastic properties of the elastic material.

In another embodiment of the present invention comprising a combination of solutions, the analysis of the driving-point response is augmented by repeating steps (aa) and (bb) using a collection of distinct differential equation models, to determine one or more elastic properties by a combination of the best-fit set of coefficients determined by each distinct differential equation model. Steps (aa) and (bb) are repeated once for each distinct differential equation model to produce a distinct best-fit solution for each distinct differential equation model. The collection of distinct best-fit solutions are combined to determine a combined solution representative of one or more elastic properties of the elastic material.

In another embodiment, the analysis of the driving-point response is repeated for a sequence of distinct time windows of the driving-point response, to produce a series of solutions representative of a series of values for one or more elastic properties wherein the series of values represents the value of the elastic property as a function of time. A time window is an embodiment of the set of distinct points in time in step (aa), wherein the set of distinct points in time occur during a defined time period of the driving-point response. Each distinct time window represents a distinct, defined time period selected from the driving-point response.

In one embodiment, the distinct time windows overlap one another in time. The series of distinct time windows represents a series of defined time periods of the driving-point response. The steps (aa) and (bb) are repeated once for each distinct time window in the series, to produce a distinct solution for each distinct time window. The series of distinct solutions represents the value of one or more elastic properties as a function of the time of the series of defined time periods.

The actuator which exerts the driving force comprises any of various kinds of dynamic actuators, including but not limited to a controlled actuator, an orbital actuator, a passive actuator, a piezoelectric actuator, a reciprocating actuator, an electro-dynamic actuator, a servo-hydraulic actuator, a seismic vibrator, a shear-wave vibrator, a P-wave vibrator, or combinations thereof.

The driving force may exceed the small-amplitude approximation limit of the elastic material, or may be within the small-amplitude approximation limit of the elastic material.

The driving force comprises a dynamic normal force, a dynamic shear force, a dynamic rotational force, or a combination thereof. A driving force which is a combination of normal, shear, and/or rotational forces can be separated into distinct component forces each representative of one component of normal, shear, or rotational force. Each distinct component force can be analyzed independently as an independent driving force. The driving force signal being analyzed comprises a signal representative of the signed magnitude of the corresponding force component.

The magnitude of the driving force varies as a function of time, and the function of time substantially representing the variation of driving-force magnitude comprises any of various functions of time, including but not limited to: a function comprising a single frequency, a range of frequencies, a superposition of a plurality of distinct harmonic frequencies, a superposition of a plurality of distinct harmonic frequency ranges, a periodic function which is an anharmonic function, a swept-frequency function, a pseudo-random function, a sinc function, an impulse function, a frequency-modulated function, an amplitude-modulated function, a function having an initial amplitude taper, a function having an ending amplitude taper, a function having a defined duration in time, a sequence of distinct functions each having a defined duration in time, or combinations thereof.

The driving-point response being analyzed comprises any one or more of the following:
- a linear driving-point response within the small-amplitude approximation;
- a nonlinear driving-point response produced by a driving force which substantially exceeds the small-amplitude approximation limit of the elastic material;
- an anharmonic driving-point response comprising a superposition of a plurality of harmonic frequency components at harmonics of the frequency components of the driving force;
- a stiffness-dominated, viscosity-dominated, or mass-dominated response, and combinations thereof, produced by a driving force comprising a range of frequencies substantially lower-than, substantially near, and/or substantially higher than the natural frequency of the elastic material; and
- a superposition of a transient response and a steady-state response.

Anharmonic frequency components present in the driving-point motion signals and driving force signals being analyzed are substantially preserved and included in the analysis.

The means to produce the driving force signal representative of the driving force exerted by the actuator on the contact surface area of the substrate material comprises any of various measurement means well known in the art, including but not limited to a force sensor, a load cell, a pressure sensor, or an accelerometer system used to determine a mass-weighted sum representative of the force output of a reciprocating actuator. The means to produce the driving-point motion signal representative of the motion of the contact surface area in response to the driving force may be any of various measurement means known in the art, including but not limited to an acceleration sensor, a velocity sensor, a displacement sensor, or a rotation sensor.

In one embodiment, the means to determine the driving force and the means to determine the driving-point motion may be sensor components of a system known in the art as an impedance head.

In another embodiment, the means to determine the driving-point motion is an acceleration sensor rigidly coupled to the driving element of the actuator, whereby the acceleration sensor produces a driving-point acceleration signal representative of the driving-point acceleration of the contact surface area.

Prior to the analysis, a measured driving-point motion signal or driving-force signal can be corrected for sensor calibration and compensated for phase and amplitude effects caused by filters, amplifiers, or other components of the measurement system which detects and produces the signal, using calibration correction and compensation methods well known by those skilled in the art.

Prior to the analysis, each of the driving-point motion signals may be filtered to attenuate an estimated measurement error and/or integration error component of the signal by using an error attenuator 20 and a fractional-cycle-interval filter 10 which are described herein. The driving force signal may be filtered to attenuate an estimated measurement error component of the driving force signal by using the error attenuator 20 and the fractional-cycle-interval filter 10 described herein.

The present invention encompasses use of a driving force or driving-point motions that may exceed the linear response range of the elastic material, and encompasses determining nonlinear elastic properties of a nonlinear elastic material. The present invention encompasses use of a dynamic force that includes anharmonic response components, and use of driving-point motions that include anharmonic motion components at harmonics of the driving force. The present invention encompasses use of a driving force and use of driving-point motions that include a transient component and a steady state component. The present invention encompasses use of a driving force comprising a range of frequencies lower than, near, and higher than the natural frequency of the elastic material.

The driving force may be exerted on an in-situ material or on an isolated sample of material.

The elastic material comprises a material for which the elastic properties are to be determined. The elastic material can be any of various types of materials, including but not limited to the following types of material: earth materials such as rock, soil, alluvium, geologic formations, unconsolidated sediments, porous material, earth materials containing pore fluids, in-situ earth materials at the surface of the earth or in a borehole or other excavation, or combinations thereof; construction materials such as foundation soils, compacted soils, soil fill, subsoil, embankments, road beds; manufactured materials; composite materials; granular materials; cohesive materials; cohesionless materials; porous materials; materials containing pore-fluids, heterogeneous materials; anisotropic materials; and combinations thereof. The elastic material can comprise biological materials such as tissue samples, bone, skin, muscle, and in-situ live organisms including humans.

3.1 The Differential Equation Model: Step (aa)

The system of linear equations formed in process (aa) represents a differential equation model of the driving-point response of the elastic material. The differential equation represents a model of the driving-point motions of the elastic material in response to the driving force. The system of linear equations comprises a set of linear equations wherein each linear equation comprises an embodiment of the differential equation evaluated at a distinct point in time. Each linear equation comprises known factors representative of the measured driving-point response, and comprises unknown parameter coefficients representative of one or more elastic properties which are to be determined. It is an object of the present invention to determine a value of one or more of the unknown parameter coefficients by determining a best-fit solution of the system of linear equations.

Any one of various models and various differential equations may be used to form the system of linear equations. Various models are known in the art which may be used to represent the driving-point response of an elastic material, including but not limited to a Maxwell model, a Kelvin model, a Voigt model, and an isotropic elastic half-space model. The model may be a linear model or a nonlinear model. The differential equation representing the model comprises a force-balance equation or an energy-balance equation.

It is understood in the description of the present invention, that the driving-point acceleration a, the driving-point velocity v, the driving-point displacement x, and the driving force $F_d$ all represent functions of time, and that they all share the same time abscissa. It is understood that the values of the driving-point acceleration a, the driving-point velocity v, the driving-point displacement x, and the driving force $F_d$ each represent the signed magnitude of a vector quantity. The driving force $F_d$ comprises a normal force, a shear force, a rotational force, or a combination thereof. If the driving force $F_d$ is a normal force, the driving force $F_d$ is in the direction normal to the contact surface area, and the driving-point motions represent motions in the same direction normal to the contact surface area. If the driving force $F_d$ is a shear force, the driving force $F_d$ is in a direction parallel to the contact surface area, and the driving-point motions represent shear motions parallel to the contact surface area in the same direction of shear as the driving force $F_d$. If the dynamic force exerted by the actuator on the contact surface area of the elastic material is a combination of normal, shear, and rotation forces, the force exerted may be expressed as the superposition of six distinct, orthogonal components—a normal force component, two orthogonal shear force components, a torsional force component, and two orthogonal rocking force components. The exerted force may be separated into the distinct, orthogonal component forces by methods well known in the art for separating components. Each one of the three distinct, orthogonal component forces may be analyzed independently as a driving force $F_d$ by the methods of the present invention. Similarly, a combination driving-point motion may be separated into distinct, orthogonal components of motion corresponding to the distinct, orthogonal components of the exerted driving force $F_d$.

In one embodiment of the present invention, the driving force $F_d$ is a normal force and the driving-point motions are normal motions. In another embodiment, the driving force $F_d$ is a shear force and the driving-point motions are motions in the same shear direction as the driving force.

3.1.1 Single Degree of Freedom Models

In one embodiment of the present invention, the differential equation model is based on a Voigt model of the elastic material. FIG. 1B depicts a Voigt-type model, which represents the elastic material as a mass-spring-damper system with a single degree of freedom.

As shown in FIG. 1B, a driving force $F_d$ acts on a mass element 4 coupled to a spring element 2 and a damper element 3 (the damper element sometimes known in the art as a dashpot). The spring element 2 and the damper element 3 are assumed to be massless. The spring element 2 and the damper element 3 are depicted spatially separated in the figure for clarity, but are considered to be acting along a single axis such that there is no rotation of the mass element 4.

The spring element 2 represents the elasticity of the elastic material, and the damper element 3 represents the viscosity of the elastic material. In a single-degree-of-freedom model the deformation of the elastic material is represented by the displacement of the mass element 4. The application of the driving force $F_d$ causes the mass 4 to move, and the motion of mass 4 represents the driving-point motion of the elastic material. The spring element 2 exerts an elastic force which opposes the driving force, and the force exerted by the spring element 2 is representative of the elastic force exerted by the elastic material in response to the deformation produced by the driving force. The elastic force is a function of the displacement of the mass element 4. A linear elastic force is linearly proportional to the displacement of the mass element 4. A nonlinear elastic force is a nonlinear function of the displacement. The damper element 3 exerts a force on the mass element 4, and the force exerted by the damper element 3 is representative of the viscous force exerted by the elastic material in response to the deformation produced by the driving force. The viscous force is a function of the velocity of the mass element 4. A linear viscous force is linearly proportional to the velocity of the mass element 4. A nonlinear viscous force is a nonlinear function of the velocity of the mass element 4.

In a linear model, the spring element 2 is a linear spring, and the damper element 3 is a linear damper. In a nonlinear model, either the spring element 2, the damper element 3, or both the spring element 2 and the damper element 4 are nonlinear.

The present invention encompasses a driving force that may exceed the linear response range of the elastic material, so in one embodiment of the present invention both the spring element 2 and the damper element 4 are modeled as having nonlinear force functions.

In one embodiment, the mass element 4 represents a "captured mass", which is the equivalent mass of a volume of the elastic material which is moving in phase with the driving element. In another embodiment, the mass element 4 represents the mass of the driving element, and the force 1 is considered to be acting on the driving element.

The elastic force exerted by a nonlinear elastic material can be represented by a polynomial function of the driving-point displacement. A general expression of a nonlinear elastic force is as follows:

$$F_s = -\sum_{i=1}^{n} k_i x^i \qquad (7)$$
$$= -(k_1 x + k_2 x^2 + k_3 x^3 + \ldots + k_n x^n)$$

where $F_s$ represents the elastic force;

$k_i$ are a set of constants representing coefficients of stiffness;

x represents the driving-point displacement;

n is the number of polynomial terms in the elastic force equation, with n sufficiently large that higher terms are negligible compared to lower terms, i.e. $\sum_{i=n+1}^{\infty} k_i x^i \approx 0$ for $i > n$.

The first coefficient $k_1$ represents the first-order stiffness of the elastic material. The second-order stiffness is represented by $k_2$, the third-order stiffness is represented by $k_3$, etc.

There are various sign conventions used in the art to represent the signed magnitude of the driving force and of each of the driving-point motions. In my description of the present invention, the sign convention is that the direction of a positive driving force is the same as the direction of a positive driving-point motion. The equations and embodiments described in the present invention may be described using other sign conventions without changing the spirit, scope, or meaning of the description.

It is apparent in equation (7) that the case where n=1 represents a linear elastic material, and the resulting expression for the elastic force is known in the art as Hooke's law:

$$F_s = -k_1 x. \tag{8}$$

Therefore it is apparent that a linear elastic material is a special case of a general representation of nonlinear elastic material.

A nonlinear viscous force can be approximated by a polynomial function of the driving-point velocity. A general expression of a nonlinear viscous force is as follows:

$$F_v = -\sum_{i=1}^{L} b_i v^i \tag{9}$$
$$= -(b_1 v + b_2 v^2 + b_3 v^3 + \ldots + b_L v^L)$$

where
 $F_v$ represents the viscous force;
 $b_i$ are a set of constants representing coefficients of viscosity;
 v represents the driving-point velocity;
 L is the number of terms in the viscous force equation, with L chosen such that the viscous force is substantially approximated by the polynomial function of degree L.

The first coefficient $b_1$ represents the first-order viscosity of the elastic material. The second coefficient $b_2$ represents the second-order viscosity, the third coefficient $b_3$ represents the third-order viscosity, etc.

Equation (7) represents an embodiment of the elastic force exerted by the spring element 2. Equation (9) represents an embodiment of the viscous force exerted by the damper element 3.

A force-balance equation is an equation representing the sum of all the various forces acting on an element of the model. For a static model the net force is zero. For a dynamic driving force, there is a net unbalanced force which produces the driving-point motion. Using Newton's second law of motion, the net unbalanced force equals the product of mass and acceleration. The net unbalanced force on the mass element 4 in the mass-spring-damper model comprises the sum of the viscous force, the elastic force, and the driving force.

The net unbalanced force (called an inertial force) causes an acceleration of the mass element 4 in response to the driving force.

A force balance differential equation model for a nonlinear mass-spring-damper system comprises equating the driving force to the sum of the inertial force, the nonlinear elastic force, and the nonlinear viscous force. The force balance differential equation model of a nonlinear mass-spring-damper system can be expressed mathematically as follows:

$$ma + \sum_{i=1}^{L} b_i v^i + \sum_{i=1}^{n} k_i x^i = F_d \tag{10}$$

where $F_d$ represents the driving force, a represents the driving-point acceleration, m represents the inertial mass of the mass element 4, the first summation represents the viscous force, and the second summation represents the elastic force. Equation (10) is a representation of a general differential equation model of a nonlinear mass-spring-damper system.

In one embodiment of the differential equation (10), the elastic material comprises a linear elastic material with the viscous force and the elastic force being approximated as linear functions. If the amplitudes of the driving force, the driving-point displacement, and the driving-point velocity are sufficiently small that the sum of the nonlinear terms of equation (10) is negligible, the driving-point response may be substantially approximated by a differential equation model called a small-amplitude approximation model.

A force balance differential equation model for a linear mass-spring-damper system comprises equating the driving force to the sum of the inertial force, the linear elastic force, and the linear viscous force. The force balance differential equation model of a linear mass-spring-damper system can be expressed as follows:

$$ma + b_1 v + k_1 x = F_d. \tag{11}$$

Therefore, the linear model is a particular embodiment of the general nonlinear model represented by equation (10) wherein only the linear terms are included.

The linear mass-spring-damper model has an inherent ambiguity in the mass m and stiffness $k_1$ if the driving force is a sinusoidal driving force and the driving-point motions are sinusoidal motions at a single frequency. If the driving-point displacement is a sinusoidal displacement $x = \sin(\omega t)$ then it follows that the driving-point acceleration is a scaled function of the displacement $a = -\omega^2 \sin(\omega t) = -\omega^2 x$, where $\omega$ represents the angular frequency and t represents time. Substituting this expression for the driving-point acceleration into equation (11) and rearranging gives $$b_1 v + cx = F_d \tag{12}$$

$$\text{where } c = (k_1 - \omega^2 m). \tag{13}$$

It is apparent from equations (12) and (13) that for a fixed value of angular frequency $\omega$ there are only two independent parameter coefficients in this embodiment of the small-amplitude approximation linear model for sinusoidal driving-point motions—the two independent parameter coefficients being the coefficient of viscosity represented by $b_1$ and a combination coefficient comprising a combination of stiffness and mass represented by c. Any combination of values of stiffness $k_1$ and mass m that results in the same value of c in equation (13) is an equivalent solution, illustrating the inherent ambiguity in determining values of stiffness and/or mass using the small-amplitude-approximation linear model.

If the angular frequency ω is zero or nearly zero, then the driving force is a static force, and the value of the parameter coefficient c in equations (12) and (13) is substantially equivalent to the first-order stiffness $k_1$. However, as the angular frequency ω increases, the value of the mass term ($ω^2m$) increases substantially, and the values of the first-order stiffness $k_1$ and mass m become substantially ambiguous. At the natural frequency of the elastic material, the combination coefficient c in equations (12) and (13) is substantially zero-valued, and the driving-point response is dominated by the viscous force component. For sufficiently large values of the angular frequency ω, the mass term ($ω^2m$) overwhelms the stiffness term $k_1$.

For these reasons, the driving-point response of an elastic material at low-frequencies substantially below the natural frequency is known in the art as a stiffness-dominated response, at frequencies near the natural frequency is known as a viscosity-dominated response, and at frequencies substantially higher than the natural frequency is known as a mass-dominated response. This classification applies to both linear and nonlinear materials and models, and to both small-amplitude and large-amplitude driving forces. Because it is an object of the present invention to encompass use of a driving force at frequencies substantially lower-than, near, and/or substantially higher than the natural frequency of the elastic material, the driving-point response encompasses stiffness-dominated, viscosity-dominated, or mass-dominated responses and combinations thereof.

For a dynamic driving force, the driving-point motions have a non-zero angular frequency ω, and the value of the combination coefficient c is a combination of the stiffness $k_1$ and the mass m. To substantially represent the net force of all force components, the force-balance equation for a mass-spring-damper system includes an inertial mass component. Therefore, if the inherent ambiguity in determining the value of stiffness or mass is not resolved, the value of stiffness determined using a static force may differ substantially from the value determined using a dynamic driving force, and the value determined using a dynamic driving force may differ substantially from the actual stiffness of the elastic material.

One method for resolving the mass-stiffness ambiguity is to determine a plurality of values of the combination coefficient c as a function of the angular frequency ω for a range of frequencies of the driving force, and the values of stiffness $k_1$ and mass m may be determined by fitting parameter coefficients $k_1$ and m using the function $c(ω)=(k_1−ω^2m)$. The method of fitting a frequency domain function for resolving this ambiguity comprises use of a range of frequencies of a sinusoidal driving force wherein the frequency of the driving force varies with time, and the parameters so determined are therefore representative of a range of frequencies that span a substantial range of times of the driving force. Therefore, this frequency domain method may resolve the inherent ambiguity of stiffness and mass, but this method is not well suited to determining a variation in elastic properties as a function of time or of frequency because the properties so determined are representative of a substantial span of times.

A driving force which exceeds the small-amplitude approximation produces an anharmonic driving-point response comprising a superposition of a plurality of harmonic frequency components at harmonics of the fundamental frequency component of the driving force. Because the driving-point motion comprises a superposition of a set of harmonic frequency components, the driving-point acceleration is not a scaled function of the driving-point displacement, so the stiffness and mass parameter coefficients are not inherently ambiguous for an anharmonic driving-point response of a nonlinear elastic material.

Therefore, another method for resolving the mass-stiffness ambiguity comprises analyzing the anharmonic driving-point motions typical of real nonlinear materials. If the amplitude and phase relationships of the harmonic components are substantially preserved, then the anharmonic driving-point motions may be analyzed to unambiguously determine the three independent parameter coefficients in equation (11). It is an advantage of the present invention that elastic properties can be determined by analyzing a driving-point response comprising an anharmonic response.

Another method for resolving the inherent ambiguity in the mass m and stiffness $k_1$ in the linear model is by a combination solution method using two or more distinct differential equation models, which I describe elsewhere in this application.

If the acceleration and mass of the mass element 4 are known quantities, then a massless model can be formed by moving the inertial force component to the right-hand side of the differential equations (10) and (11), thereby forming a driving force comprising the combination of the inertial force and the force 1 acting on the mass element 4. For example, if the acceleration and mass of the mass element 4 in FIG. 1B are known, then the inertial force component can be subtracted from the driving force 1 to produce a force representative of a driving force acting on a massless system.

FIG. 1A depicts a massless model comprising a spring-damper system, wherein the driving force $F_d$ acts on a spring element 2 and a damper element 3. The spring element 2 and the damper element 3 are assumed to be massless. In this model the driving force $F_d$ acts on the spring element 2 and damper element 3 at a point 8, and the motion of the point 8 represents the driving-point motion of the elastic material. The elastic force exerted by the spring element 2 and the viscous force exerted by the damper element 3 are equivalent to the corresponding forces and elements described for FIG. 1B.

A force balance differential equation model for a nonlinear spring-damper system comprises equating the driving force to the sum of a nonlinear elastic force and a nonlinear viscous force. The force balance differential equation model of a nonlinear spring-damper system can be expressed mathematically as follows:

$$\sum_{i=1}^{L} b_i v^i + \sum_{i=1}^{n} k_i x^i = F_d \tag{14}$$

where $F_d$ represents the driving force, the first summation represents the viscous force, and the second summation represents the elastic force. Equation (14) is a representation of a general differential equation model of a nonlinear spring-damper system.

Similarly, a force balance differential equation model for a linear spring-damper system comprises equating the driving force to the sum of a linear elastic force and a linear viscous force. The force balance differential equation model of a linear spring-damper system comprises the linear terms of equation (14):

$$b_1 v + k_1 x = F_d. \tag{15}$$

Therefore, the linear spring-damper model is a particular embodiment of the general nonlinear spring-damper model represented by equation (15) wherein only the linear terms are included.

3.1.2 Elastic Half-Space Models

A real body of elastic material comprises a volume of material which is not internally constrained to move in a single direction. When a deforming driving force is applied to a large body of elastic material, the body responds with deformations comprising components of shear strain, dimensional strains, and several forms of elastic waves which propagate into the body of the material and along the surface of the material. Determining the equations of motion for the driving-point response of an unconstrained body of elastic material is a difficult problem.

FIGS. 1C and D show diagrams of elastic half-space models comprising a semi-infinite body with a single planar surface. An elastic half-space model is commonly used to represent a large body of elastic material. In FIG. 1D, a dynamic force 9 acts on a rigid mass element 7 in contact with an elastic half-space 5. The dynamic force 9 produces motion of the mass element 7 coupled to motion of the elastic half-space 5, and the mass element 7 exerts a driving force on the elastic half-space 5. The force exerted by the mass element 7 causes deformation of the elastic half-space and radiation of elastic-wave energy from the driving point. The rigid mass element 7 is also called a footing. In FIG. 1D the force 9 is depicted as a normal force for purposes of illustration, but a shear force or rotational force can also be represented by similar models wherein the force is oriented in a shear direction, is oriented around an axis of torsion perpendicular to the half-space surface, or is oriented around an axis of rocking parallel to the surface of the half-space. It has been shown that the driving-point response of an elastic half-space can be represented by a simple mass-spring-damper system, for all modes of vibration of a rigid circular footing: a normal driving force mode, a shear driving force mode, a rocking driving force mode, and a pure torsional driving force mode. Richart, et al., have summarized several differential equation models of the driving-point response of an elastic half-space in response to a dynamic force produced by a rigid circular footing (F. E. Richart, Jr, et al., 1970, *Vibrations of Soils and Foundations*, Prentice-Hall, p. 191-230).

By combining the inertial force component of the mass element 7 with the dynamic force 9, the mass element 7 can be converted to a mathematically massless driving element 6 shown in FIG. 1C. FIG. 1C shows a driving force 1 exerted on an elastic half-space 5 by a massless, rigid driving element 6.

Richart, et al., show that the motion of a rigid, circular footing on an elastic half-space (FIG. 1D) can be represented by a differential equation model of an equivalent mass-spring-damper system (FIG. 1B). Richart, et al., also show that the motion of a rigid, massless, circular footing on an elastic half-space (FIG. 1C) can be represented by a differential equation model of an equivalent spring-damper system (FIG. 1A). For the particular case of a rectangular footing and a normal-oriented driving force, Richart, et al. show that the motion of the rectangular footing can also be represented by an equivalent spring-damper system or mass-spring-damper system (FIGS. 1A-B).

Therefore, the elastic half-space model with massive driving element (FIG. 1D) can be represented by either the nonlinear or linear mass-spring-damper differential equation models (equations (10) and (11)). The elastic half-space model with massless driving element (FIG. 1C) can be represented by either the nonlinear or linear spring-damper differential equation models (equations (14), and (15)).

For the elastic half-space differential equation models, the stiffness coefficients and viscosity coefficients are functions of frequency and the elastic properties of the half-space. Lysmer and Richart present a detailed description of differential equation models of an elastic half-space for the particular case of a normal-oriented driving force and a rigid circular footing (J. Lysmer and F. E. Richart, Jr., 1966, "Dynamic Response of Footings to Vertical Loading", J. Soil Mech. and Found. Div., Proc. ASCE, vol. 92, no. SM 1, Jan., p. 65-91). Lysmer and Richart describe differential equation models for both massless (FIGS. 1A and C) and massive (FIGS. 1B and D) elastic half-space models. For these differential equation models, they describe the functions representing the corresponding coefficients of stiffness and viscosity.

To determine elastic properties using the driving-point response of a large body of elastic material approximating an elastic half-space, it is advantageous to use a method which can measure the variation in the coefficients of stiffness and viscosity as a function of frequency, because the coefficients of stiffness and viscosity in an elastic half-space are complicated functions of frequency. By using a driving-force comprising a range of frequencies which vary as a function of time, and determining the stiffness and viscosity coefficients as a function of time, the present invention provides systems and methods which can determine values stiffness and viscosity coefficients as a function of frequency.

It is an advantage of the present invention that values of stiffness and viscosity of a nonlinear elastic material can be determined as a function of the fundamental frequency of the driving force using an anharmonic driving-point response comprising a transient component and a steady state component.

Methods for deriving elastic properties from the variation of stiffness and viscosity as a function of frequency are described in detail in Example 1.

3.1.3 Example Embodiments of the Differential Equation Model

For a large driving force that produces a driving-point response that exceeds the range of small-amplitude approximation of the linear model, such that the sum of the nonlinear terms in equation (10) is not negligible, a nonlinear model is needed to substantially represent the driving-point response of a real elastic material. Any embodiment of equation (10) comprising one or more nonlinear terms, such that L>1 or n>1, represents an embodiment of a nonlinear model. An advantage of a nonlinear model is that a large driving force and large amplitude driving-point motions may be used for determining the elastic properties. Another advantage of a nonlinear model is that the elastic properties may be determined using a driving-point response comprising an anharmonic response.

In a specific nonlinear embodiment of the force-balance differential equation model (10), the elastic material is represented by a nonlinear model with the viscous force and the elastic force being approximated as nonlinear functions to third-order terms, with L=3, n=3, and the differential equation representing the driving-point response of this nonlinear model is:

$$ma + b_1 v + b_2 v^2 + b_3 v^3 + k_1 x + k_2 x^2 + k_3 x^3 = F_d. \quad (16)$$

An advantage of the differential equation model represented by equation (16) is that it encompasses use of a driving force that exceeds the small-amplitude approximation range of the elastic material. Another advantage is that small-amplitude elastic properties may be determined by using large-amplitude driving-point motions, because the first-order coefficients $b_1$ and $k_1$ are representative of small-amplitude elastic properties but distinct values of these coefficients may be determined as distinct from the second and third order parameter coefficients in this model.

A symmetric model is another embodiment of the differential equation model, comprising only odd-order terms of the viscous force component and elastic force component. A viscous force comprising only odd-order viscosity terms result in a viscous force that is an odd, symmetric function of driving-point velocity. An elastic force comprising only odd-order elastic terms result in an elastic force that is an odd, symmetric function of driving-point displacement. An example of a force balance differential equation model of a symmetric mass-spring-damper system may be expressed by the following equation:

$$ma + b_1 v + b_3 v^3 + b_5 v^5 + \ldots + k_1 x + k_3 x^3 + k_5 x^5 + \ldots = F_d. \quad (17)$$

An advantage of the symmetric model represented by equation (17) is that it forces the even-order coefficients to be zero-valued so that the best-fit solution is a best-fit for odd-order terms only. This is useful because the response of some types of elastic material is symmetric.

A differential equation model comprising even-order terms of either the viscous force component or elastic force component is called an asymmetric model.

Another embodiment of the differential equation model comprises odd-order terms of the viscous force component and all terms of the elastic force component. The viscous odd-order differential equation model may be expressed by the following equation:

$$ma + b_1 v + b_3 v^3 + b_5 v^5 + \ldots + k_1 x + k_2 x^2 + k_3 x^3 + \ldots = F_d. \quad (18)$$

An advantage of the viscous odd-order model represented by equation (18) is that it represents the response of some kinds of elastic material wherein the viscous force is substantially dominated by odd-order terms but the elastic force comprises contributions from both even-order and odd-order terms.

In general distinct embodiments of the differential equation model can be formed by selecting only the desired terms of either the general nonlinear mass-spring-damper model represented by equation (10) or the general nonlinear spring-damper model represented by equation (14). Other distinct embodiments can be formed by assigning a constant, known value to certain selected parameter coefficients to constrain the model.

Another embodiment of the differential equation model applies to a driving force produced by a reciprocating actuator. The driving force output of a reciprocating actuator can be estimated as a weighted sum of the reaction mass acceleration and the baseplate acceleration $F_d = -(M_R a_R + M_B a_B)$ where $M_R$ and $M_B$ represent the inertial mass of the reaction-mass and of the baseplate, respectively; and $a_R$ and $a_B$ represent the acceleration of the reaction-mass and of the baseplate, respectively. Note that the baseplate acceleration $a_B$ is assumed to be equivalent to the driving-point acceleration a. Substituting the expression for the weighted sum driving force into equation (16) gives the following equation representing an embodiment of the differential equation model:

$$(m + M_b) a + b_1 v + b_2 v^2 + b_3 v^3 + k_1 x + k_2 x^2 + k_3 x^3 = -M_R a_R. \quad (19)$$

Substituting the expression for the weighted sum driving force of a reciprocating actuator into equation (12) gives the following expression representing another embodiment of the small-amplitude approximation model:

$$c_2 a + b_1 v = -M_R a_R \quad (20)$$

where (21)

$$c_2 = (m + M_B) - \frac{k_1}{\omega^2}.$$

An advantage of the models represented by equations (19) and (20) for a reciprocating actuator is that the baseplate acceleration enters into the model in only one term of the equation. In the models represented by equations (12) and (16) the baseplate acceleration of a reciprocating actuator appears twice—once as a driving-point acceleration on the left-hand side, and again as an implicit component of the weighted sum driving force $F_d$ comprising the right-hand side function.

Another embodiment of the differential equation model is an empirical differential equation model, which is a model not strictly derived from a mechanical model. An embodiment of an empirical differential equation model representative of an elastic material is expressed by the following equation:

$$ma + \sum_{i=1}^{L} b_i v^i + \sum_{i=1}^{n} k_i x^i + c_1 ax + c_2 av + c_3 vx + c_4 = F_d \quad (22)$$

where $c_1$, $c_2$, $c_3$ represent parameter coefficients of terms representing the basis functions ax, av, and vx, respectively; and $c_4$ represents the value of a constant-valued component (i.e. a DC, zero-frequency, or static component) in the driving force $F_d$. Equation (22) is derived from equation (10) by adding the three motion product terms and the constant-valued term. This model is useful because it provides an improved fit in the case of a driving-point response that contains residual constant-valued offset or other nonlinear effects in the driving-point response signals.

3.1.4 Energy Balance Differential Equation Models

Another class of differential equation models which can represent the driving-point response are energy balance equations. An energy balance equation is an equation representing a sum of various forms of energy content of the elements of the model. Forms of energy which can enter into an energy balance equation comprise mechanical energy, kinetic energy, potential energy, dissipated energy, or combinations thereof. An energy balance equation is based on the principles of conservation of energy.

In one embodiment comprising conservation of mechanical energy, the total mechanical energy content of the driving-point motions of the elastic material may be expressed as the sum of the potential energy and the kinetic energy. The potential energy is the energy stored in the elastic deformation of the elastic material, and the kinetic energy is the energy of the mechanical motion of the material. The potential energy may be determined from the integral of the work done by the elastic force, where work is the product of force and distance. Using equation (7) to represent the elastic force, the elastic potential energy may be represented by the following equation:

$$U = \int_x F_s \, dx \qquad (23)$$

$$= -\sum_{i=1}^{n} \int_x k_i x^i \, dx$$

$$U = -\left(\frac{1}{2}k_1 x^2 + \frac{1}{3}k_2 x^3 + \frac{1}{4}k_3 x^4 + \ldots + \frac{1}{n+1}k_n x^{n+1}\right)$$

where U represents the elastic potential energy as a function of time, and $F_s$ represents the elastic force, which may be represented by equation (7). An embodiment of an energy-balance differential equation based on a nonlinear mass-spring-damper model comprises:

$$\frac{1}{2}mv^2 + \frac{1}{2}k_1 x^2 + \frac{1}{3}k_2 x^3 + \frac{1}{4}k_3 x^4 + \ldots + \frac{1}{n+1}k_n x^{n+1} = E \qquad (24)$$

where E represents the total mechanical energy, the first term on the left-hand side ($mv^2/2$) represents the kinetic energy of the mass element, and the other terms on the left-hand side represent the potential energy. This differential equation (24) can be used to determine values for the mass coefficient m and the set of stiffness coefficients $k_i$ by making an assumption about the variation of the total energy E on the right-hand side of the equation.

Another embodiment of an energy-based differential equation model may be produced by algebraic rearrangement of equation (24):

$$\frac{1}{2}\left(\frac{k_1}{m}\right)x^2 + \frac{1}{3}\left(\frac{k_2}{m}\right)x^3 + \frac{1}{4}\left(\frac{k_3}{m}\right)x^4 + \ldots + \frac{1}{n+1}\left(\frac{k_n}{m}\right)x^{n+1} - \frac{E}{m} = -\frac{1}{2}v^2. \qquad (25)$$

In this embodiment, the right-hand side of the equation (25) is a known value determined from the driving-point velocity, and all the unknown coefficients are on the left-hand side. On the left-hand side, the unknown coefficient ($k_1/m$) is in units of angular frequency squared (radians-squared per second-squared), and represents the square of a characteristic frequency of the elastic material. The characteristic frequency is proportional to the natural frequency of free vibrations of the mass-spring-damper model.

Using a polynomial function to estimate the value of the energy term in equation (25) gives another embodiment of an energy-balance differential equation model:

$$\frac{1}{2}\left(\frac{k_1}{m}\right)x^2 + \frac{1}{3}\left(\frac{k_2}{m}\right)x^3 + \ldots + \frac{1}{n+1}\left(\frac{k_n}{m}\right)x^{n+1} - \frac{e_0}{m} - \frac{e_1 t}{m} - \frac{e_2 t^2}{m} = -\frac{1}{2}v^2 \qquad (26)$$

where the total mechanical energy E as a function of time t is represented by the terms of a polynomial of degree n:

$$E = e_0 + e_1 t + e_2 t^2 + \ldots + e_n t^n \qquad (27)$$

where $e_0, e_1, e_2, \ldots, e_n$ represent the coefficients of the polynomial. In other embodiments, any one of various other functions of time may be used to represent the value of the total energy terms of the differential equation (26).

An advantage of the embodiments of the differential equation model represented by equations (24), (25), and (26) is that they each provide a model that is independent of the viscosity. Another advantage of the differential equation models (24), (25), and (26) is that the value of the driving force does not enter the equation, so it is not necessary to have a value of the driving force to use these models for determining one or more elastic properties.

In the equations (24), (25), and (26) the energy terms are unknown parameter coefficients to be determined by solving the system of linear equations based on the model. However, in another embodiment of the present invention, a value representative of the energy term can be measured, to produce an energy-balance differential equation model wherein the energy terms are known quantities. The total energy transferred to the elastic material by the driving force is the work done by the driving force, where work is the product of force and differential displacement:

$$E_T = \int F_d \, dx \qquad (28)$$

where $E_T$ is the total energy transferred to the elastic material by the work done by the driving force $F_d$. The differential displacement dx can be expressed as the product of the velocity and the time difference: dx=v dt. Substituting for dx gives the equation $$E_T = \int F_d v \, dt \qquad (29)$$

so that the total energy input to the system as a function of time may be determined by the time integration of the product of the driving force signal and the driving-point velocity signal.

Part of the total energy transferred to the elastic material dissipates due to the viscosity of the material. The total energy is the sum of the mechanical energy and the dissipated energy. The dissipated energy is the work done by the viscous force. The dissipated energy can be determined by determining the coefficients of viscosity using a force balance differential equation model, and using the coefficients of viscosity to determine the viscous force. The viscous force so determined can be multiplied by the velocity and integrated over time to produce a signal representative of the power dissipated as a function of time. The dissipated power so determined can be subtracted from the total energy to produce an estimated value of the mechanical energy. The value of the mechanical energy so produced can be used as a known quantity in an embodiment of the energy-balance equation (24), wherein the right-side function is the known mechanical energy.

In a combined solution, the values of the unknown parameter coefficients can be determined by a combination of solutions of two or more distinct differential equation models to produce a combined estimate of the value of the elastic properties.

In one embodiment of a combined solution, the ambiguity of the values of the stiffness and mass in the linear model (12) can be resolved by combination with the solution of the energy-balance model (25). The solution of the linear model (12) determines the values of the first-order coefficient of viscosity $b_1$ and the combination coefficient $c_1$. The solution of the energy-balance model (25) determines the value of the fundamental natural frequency coefficient ($k_1/m$), which can be used to determine unambiguous values of stiffness and mass using the expression (13) for the combination coefficient $c_1$:

$$m = \frac{c_1}{\left(\frac{k_1}{m}\right) - \omega^2}, \quad k_1 = \frac{c_1}{1 - \left(\frac{\omega^2}{(k_1/m)}\right)}. \qquad (30)$$

In the various embodiments of the differential equation model described herein, the known quantities comprise the known value of one or more signals representative of the driving-point response—the driving force, the driving-point acceleration, the driving-point velocity, and the driving-point displacement. The unknown quantities comprise the elastic parameter coefficients—coefficients of mass, of stiffness, and of viscosity.

3.2 Forming the System of Linear Equations: Step (aa)

It can be seen in the various embodiments of the differential equation model described herein in equations (10), (11), (12), (14) (15) (16), (17), (18), (19), (20), (22), (24), (25), and (26) supra that the differential equation model may be represented by a linear combination of terms and a right-hand side function:

$$c_1 Z_1(t) + c_2 Z_2(t) + \ldots + c_N Z_N(t) = y(t). \quad (31)$$

Each term may be represented as a function of time, the function of time comprising the product of an unknown parameter coefficient and a known function of the driving-point response signals. Each function of time may be represented mathematically by a term of the form $c_j Z_j(t)$, where $c_j$ represents an unknown parameter coefficient and $Z_j(t)$ represents a known function of the driving-point response signals. Each function of the driving-point response signals $Z_j(t)$ is called a basis function, and the differential equation may be expressed as a linear combination of the set of basis functions. There is one basis function for each term of a differential equation model. Each basis function comprises a function of one or more of the known driving-point response signals.

A basis function $Z_j(t)$ may be a linear or a nonlinear function of time, including but not limited to polynomial functions, trigonometric functions, exponential functions, and logarithmic functions. A basis function $Z_j(t)$ may be a constant function of time. The description "linear equation" and "linear combination" refer to linear dependence of the unknown parameter coefficients $c_j$.

Therefore, in one embodiment the differential equation model comprises a right-hand side function and a linear combination of a set of basis functions representative of the terms of the differential equation model. The coefficients of the linear combination are the unknown parameter coefficients, one or more of which is representative of an elastic property of the elastic material. In this embodiment, the differential equation model may be expressed mathematically by an equation of the form $$\sum_{j=1}^{N} c_j Z_j(t) = y(t) \quad (32)$$

where y(t) represents the right-hand side function, $Z_j(t)$ represents the set of N basis functions corresponding to the N terms of the differential equation, and $c_j$ represents the N unknown parameter coefficients.

For example, equation (16) is an embodiment of the differential equation model (32) wherein N=7; the right-hand side function y(t) is the driving force $F_d$; the set of seven basis functions $Z_j(t)$ are $$a, v, v^2, v^3, x, x^2, x^3; \quad (33)$$

and the seven unknown parameter coefficients $c_j$ are $$m, b_1, b_2, b_3, k_1, k_2, k_3. \quad (34)$$

In another example, equation (26) is an embodiment of the differential equation (32) wherein the right-hand side function y(t) is $(-v^2/2)$; the set of basis functions $Z_j(t)$ are $$\frac{x^2}{2}, \frac{x^3}{3}, \frac{x^4}{4}, \ldots, \frac{x^{n+1}}{n+1}, -1, -t, -t^2; \quad (35)$$

and the unknown parameter coefficients $c_j$ are $$\left(\frac{k_1}{m}\right), \left(\frac{k_2}{m}\right), \left(\frac{k_3}{m}\right), \ldots, \left(\frac{k_n}{m}\right), \frac{e_0}{m}, \frac{e_1}{m}, \frac{e_2}{m}. \quad (36)$$

In one embodiment of the present invention, forming the system of linear equations in step (aa) comprises evaluating the differential equation at a set of M distinct times $t_i$ to produce a set of M distinct equations representative of the differential equation. In the set of equations, each distinct equation represents the differential equation evaluated at one distinct time $t_i$ in the set of M distinct times, the distinct time being the abscissa of the basis functions and the right-hand side function. The set of equations so produced are a system of linear equations which represent a model of the driving-point response of an elastic material. The system of linear equations can be expressed mathematically by a set of equations of the form:

$$\sum_{j=1}^{N} c_j z_{ij} = y_i \text{ for } i = 1, 2, 3, \ldots, M. \quad (37)$$

where $c_j$ are N unknown parameter coefficients which are related by the set of M equations, each coefficient $c_j$ corresponding to the unknown coefficient of the $j^{th}$ term of the differential equation (32);

$z_{ij}$ are known values determined from the basis functions corresponding to the terms of the differential equation, each $z_{ij}$ representing the value of the basis function of the $j^{th}$ term of the differential equation (32) evaluated at time $t_i$, such that $z_{ij} = Z_j(t_i)$;

$y_i$ are M known values that make up the right-hand side of the equations, each $y_i$ being the value of the right-hand side function evaluated at time $t_i$, such that $y_i = y(t_i)$;

i indicates the equation number, and it is the first subscript index of $z_{ij}$;

j indicates the term number for the position of the terms in the differential equation;

N represents the number of terms in the differential equation.

The set of equations (37) is a system of M linear equations in N unknowns, and the system (37) may be expressed by an equivalent set of equations in expanded form:

$$\begin{aligned} c_1 z_{11} + c_2 z_{12} + c_3 z_{13} + \ldots + c_N z_{1N} &= y_1 \\ c_1 z_{21} + c_2 z_{22} + c_3 z_{23} + \ldots + c_N z_{2N} &= y_2 \\ c_1 z_{31} + c_2 z_{32} + c_3 z_{33} + \ldots + c_N z_{3N} &= y_3 \\ \vdots \quad \vdots \quad \vdots \quad \ddots \quad \vdots \quad &\vdots \\ c_1 z_{M1} + c_2 z_{M2} + c_3 z_{M3} + \ldots + c_N z_{MN} &= y_M \end{aligned} \quad (38)$$

Each equation in the set of equations (38) represents the differential equation of motion for the driving-point response evaluated at a distinct point in time $t_i$. The system of equations

(38) is formed by evaluating the basis functions $z_{ij}=Z_j(t_i)$ and the corresponding right-hand side values $y_i=y(t_i)$ based on the differential equation model (32) at each time in the set of times $t_i$.

The set of times $t_i$ span a range of time of defined duration called a time window, having a start time and an end time. The time window may include the entire duration of the available driving-point response signal, or the time window may be of shorter duration that includes only a portion of the available driving-point response signal.

The set of distinct points in time $t_i$ comprises any one or more of the following: a sequence of times at substantially uniform intervals of time; a sequence of times at intervals of time that are not substantially uniform intervals of time; a set of times not in time-sequential order; a set of times including substantial gaps in time; and/or combinations thereof. There is no limitation on the uniformity of time intervals, the order of the times, or the pattern of time intervals. In one embodiment, the set of times $t_i$ represent the times of a sequence of samples of the driving-point response signals that are sampled at substantially uniform intervals of time. In a non-uniform embodiment, the set of times $t_i$ may represent a series fractional-cycle-interval times of a phase-sampled signal which is sampled at a series of fractional-cycle-intervals represented by $t_k$ in equation (61). In yet another embodiment, the set of times $t_i$ may be at non-uniform intervals of time that are unrelated.

The number of equations M in the system of equations is selected such that the number of equations M is greater than or equal to N the number of unknown coefficients in the equations (M≧N). If the number of equations is greater than the number of unknown coefficients, the system of linear equations is overdetermined, and the solution represents a best-fit solution for the time period represented by the set of times $t_i$ at which the equations are evaluated. Increasing the number of equations may produce an improved solution due to cancellation of noise and residual errors in the driving-point response signals. However, if the elastic properties change substantially with time during the duration of the driving-point response, and if increasing the number of equations requires increasing the duration of the time window represented by the set of times $t_i$, then increasing the length of the time window would reduce the resolution of the change in the elastic properties as a function of time, the solution being representative of a time-average of the changing elastic properties. Increasing the number of equations also increases the processing required to form and solve the system of linear equations. The number of equations M is selected depending on the noise cancellation requirements of the particular application, the time resolution requirements of the particular application, and the resources available in the particular implementation system.

For clarity, the following example comprises one specific embodiment of the system of linear equations, wherein the system represents the driving-point response described by the differential equation (16), the differential equation (16) is evaluated at a set of M distinct times $t_i$ to produce a system of M distinct equations for i=1, 2, 3, ..., M:

$$ma_1 + b_1 v_1 + b_2 v_1^2 + b_3 v_1^3 + k_1 x_1 + k_2 x_1^2 + k_3 x_1^3 = F_1 \quad (39)$$
$$ma_2 + b_1 v_2 + b_2 v_2^2 + b_2 v_2^3 + k_1 x_2 + k_2 x_2^2 + k_3 x_2^3 = F_2$$
$$ma_3 + b_1 v_3 + b_2 v_3^2 + b_3 v_3^3 + k_1 x_3 + k_2 x_3^2 + k_3 x_3^3 = F_3$$
$$\vdots \quad \vdots \quad \vdots \quad \vdots \quad \vdots \quad \vdots \quad \vdots \quad \vdots$$
$$ma_M + b_1 v_M + b_2 v_M^2 + b_3 v_M^3 + k_1 x_M + k_2 x_M^2 + k_3 x_M^3 = F_M$$

where
$F_i$ represents the value of the driving force at the time $t_i$;
$a_i$ represents the value of the driving-point acceleration at the time $t_i$;
$v_i$ represents the value of the driving-point velocity at the time $t_i$;
$x_i$ represents the value of the driving-point displacement at the time $t_i$; and
m, $b_1$, $b_2$, $b_3$, $k_1$, $k_2$, $k_3$ represent the unknown values of the parameter coefficients in the differential equation (16).

Each equation in the set of equations (39) represents the differential equation (16) evaluated a distinct time in the set of times $t_i$. The known values of the driving force $F_1$, $F_2$, $F_3$, ..., $F_M$ on the right-hand side of the equations in the system (39) correspond to the $y_i$ on the right-hand side of the equations in the system (37). The values $a_i$, $v_i$, $v_i^2$, $v_i^3$, $x_i$, $x_i^2$, $x_i^3$ in the system (39) represent the basis functions evaluated at the set of times $t_i$, and correspond to the basis function values $z_{i1}$, $z_{i2}$, $z_{i3}$, $z_{i4}$, $z_{i5}$, $z_{i6}$, $z_{i7}$ in the system (37). The unknown parameter coefficients m, $b_1$, $b_2$, $b_3$, $k_1$, $k_2$, $k_3$ in the system (39) correspond to the unknown coefficients $c_j$ in the system (37). Therefore, the system of equations (39) is a specific embodiment of the general system of linear equations (38) based on the differential equation (16) wherein N=7, there being seven basis functions and seven unknown parameter coefficients representing elastic properties of the elastic material.

Note that the equations (39) are nonlinear in x and v, but are linear with respect to the unknown coefficients $c_j$. In the description of the present invention, the term "system of linear equations" refers to linear dependence of the unknown parameter coefficients $c_j$ in the set of equations (37); the known basis functions $z_{ij}$ may or may not be linear.

In one embodiment, the system of linear equations (37) may be represented by an equivalent equation in matrix form:

$$Z \cdot C = Y \quad (40)$$

where the raised dot denotes matrix multiplication, Z represents an M×N matrix of the values of the basis functions $z_{ij}$ on the left-hand side of the system (37), Y represents a one-column matrix of the M known values $y_i$ on the right-hand side of the system (37), and C represents a one-column matrix of the set of N unknown coefficients $c_j$:

$$Z = \begin{bmatrix} z_{11} & z_{12} & z_{13} & \cdots & z_{1N} \\ z_{21} & z_{22} & z_{23} & \cdots & z_{2N} \\ z_{31} & z_{32} & z_{33} & \cdots & z_{3N} \\ \vdots & \vdots & \vdots & \ddots & \vdots \\ z_{M1} & z_{M2} & z_{M3} & \cdots & z_{MN} \end{bmatrix} \quad C = \begin{bmatrix} c_1 \\ c_2 \\ c_3 \\ \vdots \\ c_N \end{bmatrix} \quad Y = \begin{bmatrix} y_1 \\ y_2 \\ y_3 \\ \vdots \\ y_M \end{bmatrix}. \quad (41)$$

The matrix Z is called a design matrix. Each row of the design matrix Z represents one equation in the system of linear equations evaluated at a distinct time. Each column in the design matrix Z represents one basis function of the differential equation model of the driving-point response of the elastic material. The matrix row index is the first subscript and the matrix column index is the second subscript of the matrix elements $z_{ij}$.

The matrix C is called the parameter matrix, and the vector Y is called the right-hand side function.

In one embodiment of the present invention, forming the system of linear equations comprises determining a differential equation model having a set of basis functions, a set of parameter coefficients, and a right-hand side function; forming the design matrix Z and the right-hand side matrix Y according to expression (41); determining the values of the elements of the design matrix Z by evaluating the basis functions at a set of distinct times using the driving-point response signals according to a differential equation model; and determining the values of the elements of the right-hand side matrix Y by evaluating the right-hand side function at the set of distinct times. The matrices so formed are representative of the system of linear equations. In this embodiment, in step (bb) the system of linear equations is solved in matrix form to determine the best-fit parameter matrix C.

An advantage of solving the system of linear equations in matrix form is that the rows of the design matrix do not need to be in time-sequential order. In one embodiment of the system of linear equations, the design matrix is embodied as a circular buffer in a digital memory system, which allows for efficient means for forming the system of linear equations. Solving the system of linear equations may be accomplished with the rows of the design matrix in any order, regardless of the order that the rows are stored in the circular buffer. In another embodiment, the system of linear equations may be formed based on portions of the driving-point response including gaps in time. For example, the design matrix may be formed using only the negative velocity portion of each stroke cycle of the driving force, with the positive velocity portion if each stroke cycle excluded. Excluding portions of each stroke cycle may produce time gaps in the system of linear equations, the time gap resulting from the excluded portion of the stroke cycle.

Analyzing compressive strokes separately from de-compressive strokes is useful because elastic properties may be different for a compressive stroke than for a de-compressive stroke of the driving force. Solving the system of linear equations in matrix form is therefore useful as a method for determining distinct values for compressive elastic properties or for dilatational elastic properties from a dynamic driving force.

In another embodiment, each basis function of the differential equation model is represented by a signal, rather than by a column of the design matrix. In other words, each column of the design matrix Z is embodied as a distinct signal. In this embodiment, forming the system of linear equations comprises determining a differential equation model having a set of basis functions, a set of parameter coefficients, and a right-hand side function; producing a set of basis function signals each of which is representative of one distinct basis function $Z_j(t)$ corresponding to one column of the design matrix Z, with a one-to-one correspondence of the basis function signals to the basis functions $Z_j(t)$; and producing a right-hand side signal y(t) representative of the right-hand side function. The set of basis function signals $Z_j(t)$ and the right-hand side signal y(t) so formed are representative of the system of linear equations. In this embodiment, in step (bb) the system of linear equations is solved by determining a best-fit linear combination of the basis function signals that fits the right-hand side signal. The coefficients of the best-fit linear combination are representative of the unknown parameter coefficients.

3.3 Solving the System of Linear Equations: Step (bb)

In step (bb), the system of linear equations formed in step (aa) is solved to determine a value of one or more of the elastic properties. It is an object of the present invention to determine the value of one or more of the elastic properties by solving the system of linear equations (37) to determine a solution which comprises a best-fit set of parameter coefficients. One or more of the set of parameter coefficients so determined are representative of one or more elastic properties of the material, in accordance with the differential equation model used to form the system of linear equations.

In one embodiment, the best-fit solution is determined by solving the matrix equation Z·C=Y for the unknown parameter matrix C, given the design matrix Z and the right-hand side vector Y which are determined from the known driving-point response as described above. As long as the number of equations M is greater-than or equal to N the number of unknown parameters in the parameter matrix C, a solution may be possible if the design matrix Z is not singular. Even if the design matrix Z is singular or ill-conditioned, a best-fit solution may be found that produces the best approximation to the system of linear equations (37). The best-fit solution is the set of parameter coefficients C that produces the best approximation to the system of linear equations (37) in the least-squares sense. In other words, one embodiment of the best-fit solution comprises the solution C which minimizes $$\chi^2 = |Z \cdot C - Y|^2 \qquad (42)$$

where $\chi^2$ represents a chi-squared merit function to be minimized.

Other merit functions other than chi-squared are also known which may be used to determine a best-fit solution, including but not limited to L-norms.

Various numerical methods are well known in the art for solving the system of linear equations (37) to determine the unknown parameter coefficients, the methods including but not limited to Gauss-Jordan elimination, LU decomposition, matrix inversion methods, general linear least squares methods, singular value decomposition methods, and Kalman filter methods. Detailed description of these methods are widely available in the art, including in Press et al. (Press et al., *Numerical Recipes in C*, Cambridge University Press, 1988, pp. 28-84 and pp. 528-539).

If the number of equations M is equal to the number of unknowns N, the design matrix Z is a square matrix, and the system of linear equations may be solved by direct methods, including but not limited to Gauss-Jordan elimination or LU decomposition. However, if the matrix Z is singular or nearly singular, the direct methods may fail or the solution so produced by direct methods may be substantially affected by solution error such that the solution is not the best-fit solution, or may not be substantially representative of the actual elastic properties of the elastic material.

If the number of equations M is greater than the number of unknowns N, the system of linear equations is overdetermined, and a best-fit solution method is needed. If the number of equations M is less than the number of unknowns N, the system of linear equations is underdetermined, but it may be possible to find a particular solution which is a best-fit solution that minimizes equation (42).

It is well known by those skilled in the art of linear systems that the solution of the system of linear equations (37) is a particular solution, and there may also be one or more homogeneous solutions which may be combined with the particular solution to form a general solution. For each system of linear equations (37), there is another associated system called the homogeneous system wherein the right-hand side elements $y_i$ are all zero value:

$$\sum_{j=1}^{N} c_j z_{ij} = 0 \text{ for } i = 1, 2, 3, \ldots, M. \qquad (43)$$

or the equivalent matrix expression:

$$Z \cdot C = 0. \qquad (44)$$

The system of linear equations (37) wherein one or more of the elements $y_i$ are non-zero is called a non-homogeneous system. The system of linear equations (43) is the homogeneous system corresponding to the non-homogeneous system (37). A solution of the non-homogeneous system (37) is called a particular solution. A solution of the homogeneous system (43) is called a homogenous solution. The solution C=0 is always a solution of the homogeneous system, but there may also exist non-zero homogeneous solutions. The set of all solutions of the homogeneous system is the nullspace of the non-homogeneous system. A set of independent solutions of the homogeneous system form a vector basis determining the nullspace. Any linear combination of a particular solution and a homogeneous solution is also a particular solution of the non-homogeneous system:

$$Z \cdot (C+H) = Y \quad (45)$$

where C is a particular solution and H is a homogeneous solution of the associated homogeneous system (43). The general solution is the sum of a particular solution and linear combinations of the basis vectors of the null space:

$$G = C + g_1 H_1 + g_2 H_2 + \ldots + g_k H_k \quad (46)$$

where G is the general solution, C is the particular solution, $H_k$ are a set of homogeneous solutions which are k independent vectors forming a k-dimensional vector basis for the nullspace of the non-homogeneous system, and $g_k$ are arbitrary scalars. If H=0 is the only homogeneous solution (i.e. there are no non-zero homogeneous solutions), then the general solution is the particular solution C.

A system of linear equations is singular if it has a non-zero null space; that is, if there exists a non-zero homogeneous solution of the system of linear equations, the system is singular. The system of linear equations is nearly singular if there exists a non-zero solution which substantially approximates a solution of the homogeneous system. The design matrix Z is singular if there exists a non-zero parameter matrix H such that $Z \cdot H = 0$, where H is a non-zero homogeneous solution. The design matrix Z is nearly singular if there exists a non-zero parameter matrix H which substantially approximates a homogeneous solution, such that $Z \cdot H \approx 0$, where the approximation is sufficiently close to zero that the solution to the non-homogeneous system is overwhelmed by nearly homogeneous components resulting in a particular solution which may not be substantially representative of the actual elastic properties of the elastic material. A singular or nearly singular matrix is also called an ill-conditioned matrix.

In practice, for systems of linear equations (37) based on differential equation models of the nonlinear driving-point response of nonlinear elastic material, the system of linear equations may be ill-conditioned, due to characteristics inherent in the driving-point response of real nonlinear elastic materials. An ill-conditioned system of linear equations produces a design matrix Z that is singular or is nearly singular. To produce a solution that accurately represents one or more elastic properties of real elastic materials, the method for solving the system of linear equations needs to solve ill-conditioned systems in a way that controls the contribution of the nullspace components of the solution.

An example of a singular system of linear equations based on an elastic differential equation model is the linear elastic model represented by equation (11) supra. As described for equations (12) and (13) supra, even though there are three parameter coefficients in equation (11), for a mono-frequency sinusoidal displacement there are only two independent parameters in this linear model which is a condition known as column degeneracy. Any combination of values of stiffness $k_1$ and mass m that produce a zero-valued combination coefficient $c_1$ in equation (13), such that $k_1 = \omega^2 m$, represents a homogeneous solution of the system of linear equations. Therefore, the system of linear equations based on the linear elastic model described by equation (11) supra for a driving-point motion which is a sinusoidal function of a single frequency is a singular system.

In the present invention, the best-fit solution of the system of linear equations (37) is a particular solution. However, if the design matrix Z is ill-conditioned, there may exist a nullspace of non-zero homogeneous solutions or nearly homogeneous solutions of the associated homogeneous system, and therefore a general solution may be formed by combining the particular solution and a linear combination of the vector basis of the nullspace. The general solution may be used to find other particular solutions of the system of linear equations (37).

It is an object of the present invention to solve the system of linear equations (37) for overdetermined systems, underdetermined systems, and/or ill-conditioned systems, by a method which provides control of nullspace components of the solution.

3.4 Solution by Singular Value Decomposition

In one embodiment, the method for solving the system of linear equations is a singular value decomposition (SVD) method, comprising singular value decomposition of the design matrix Z to solve the system of linear equations (37) to determine the best-fit set of coefficients. SVD methods are known in the art to produce a particular solution that is the best-fit solution in the least squares sense, which minimizes the chi-square merit function $\chi^2$ in equation (42) for overdetermined systems, underdetermined systems, and/or ill-conditioned systems. Singular value decomposition of the design matrix Z identifies the nullspace components of the design matrix Z that are singular or nearly singular, and these nullspace components may be controlled or may be removed from the solution.

There are several advantages of the singular value decomposition method. Singular value decomposition of the design matrix Z provides a method for determining a particular solution that is the best-fit solution. Singular value decomposition of the design matrix Z provides a method for determining the best-fit solution of an ill-conditioned system of linear equations. SVD also provides a method to determine homogeneous solutions $H_k$ that are substantially representative of a vector basis of the null space, and thereby provides a method for determining the general solution through combination of the particular solution and the vector basis of the null space. SVD provides a method to control the contribution of the nullspace components of the solution, to either eliminate the nullspace components, or to form a particular solution by a linear combination of the nullspace components and the best-fit solution. SVD provides a method for evaluating the degree of ill-conditioning of the system of linear equations. SVD provides a method for determining a measure of an estimated probable error of each coefficient in the best-fit solution, and thereby provides a method to estimate a probable error of each of the elastic properties determined from the best-fit solution.

In one embodiment of step (bb), the system of linear equations formed in step (aa) is solved by singular decomposition to determine a best-fit solution, wherein the system of linear equations is embodied by a design matrix Z and by a right-hand side vector Y, the method for determining the solution comprising:

(cc) determining a singular value decomposition of the design matrix, to produce three distinct matrices whose product is equivalent to the design matrix, the three distinct matrices being a left-side matrix which is a column-orthogonal matrix, a singular value matrix which is a diagonal matrix comprising diagonal elements representing singular values each having a value which is positive or zero, and the transpose of a basis matrix which is an orthogonal square matrix representing a normalized vector basis of the solution space, each column of the basis matrix comprising a solution basis vector;

(dd) eliminating nearly singular basis vectors from the singular value decomposition so determined, to produce an adjusted singular value decomposition;

(ee) forming a dot product of the right-hand side matrix with each column of the left-side matrix weighted by the inverse of the corresponding singular value in the adjusted singular value decomposition so produced;

(ff) forming a linear combination of the solution basis vectors so determined in step (cc) to produce the best-fit solution, the coefficients of the linear combination being the corresponding dot products so formed in step (ee).

The best-fit solution produced in step (ff) is the best-fit set of parameter coefficients C, one or more of which are representative of elastic properties of the elastic material.

In step (cc), the design matrix Z is factored as the equivalent product of three distinct matrices, called the singular value decomposition, and the factorization may be expressed by the following matrix equation:

$$Z = U \cdot W \cdot V^T \quad (47)$$

where the raised dot denotes matrix multiplication, and

Z represents the design matrix comprising M rows by N columns;

U represents the left-side matrix comprising M rows by N columns;

W represents the singular value matrix, a square diagonal matrix comprising N diagonal elements each having a value greater than or equal to zero;

$V^T$ represents the transpose of the basis matrix V, the basis matrix V comprising a square orthogonal matrix N rows by N columns.

The matrices U, W, and $V^T$ together represent the singular value decomposition of the design matrix Z.

Various numerical methods for performing the singular value decomposition of a matrix are well known by those skilled in the art, and any one of these various numerical methods may be used as an embodiment for performing the singular value decomposition in step (cc). For example, Press, et al. provide a describe of one embodiment of SVD procedures and numerical algorithms (W. Press et al., *Numerical Recipes in C*, Cambridge University Press, 1988, pages. 60-72, pp. 534-539, and pp. 556-557).

Other embodiments of methods for performing the singular value decomposition are widely known in public domain software and in commercially available software libraries, including software for embedded digital signal processors (DSP's). Some of these available methods have various advantages in efficiency, accuracy, or ease of implementation. In one embodiment of the present invention, the system for determining the singular value decomposition of the design matrix in step (cc) is by a singular value decomposition method and numerical algorithm embodied in software or firmware code procedures executing on a digital processor.

The basis matrix V comprises a normalized vector basis of the solution space of the system of linear equations represented by the design matrix Z. Each column of the basis matrix V comprises an independent basis vector of the solution space, the set of columns comprising an orthonormal set of basis vectors which spans the solution space. Determining the best-fit solution in step (ff) comprises forming a linear combination of the basis vectors which are the columns of the basis matrix V. The columns of the basis matrix V which correspond to a zero-valued or nearly zero-valued singular value in the same column of the singular value matrix W comprise a normalized vector basis of the nullspace of the system of linear equations.

In an embodiment of steps (ee) and (ff) the method for determining the best-fit solution may be expressed by the following matrix equation:

$$C = V \cdot (W^{-1} \cdot (U^T \cdot Y)) \quad (48)$$

where the raised dot denotes matrix multiplication, and

C represents the parameter coefficient matrix comprising the best-fit solution;

V represents the basis matrix comprising an N row by N column matrix of solution basis vectors;

$W^{-1}$ represents the inverse of the singular value matrix;

$U^T$ represents the transpose of the left-side matrix U.

In the embodiment represented by equation (48), forming the dot product in step (ee) comprises the matrix product result within the parentheses; and forming a linear combination of the solution basis vectors in step (ff) comprises the matrix product of the basis matrix V and the result of the matrix product within the outer parentheses.

Since the solution basis matrix W is a diagonal matrix, the inverse $W^{-1}$ is also a diagonal matrix comprising diagonal elements ($1/w_k$) equal to the reciprocal of the corresponding diagonal elements of W.

In an equivalent embodiment of steps (ee) and (ff), equation (48) may be represented by an equivalent expression in expanded notation by the pair of equations:

$$d_k = \sum_{i=1}^{M} \frac{u_{ik} y_i}{w_k} \text{ for } k = 1, 2, \ldots, N \quad (49)$$

$$c_j = \sum_{k=1}^{N} d_k v_{jk} \text{ for } j = 1, 2, \ldots, N \quad (50)$$

where $d_k$ represents the dot product of the $k^{th}$ column of U with the right-hand side matrix Y, weighted by the reciprocal of the corresponding singular value $w_k$;

$u_{ik}$ represents an element of the left-side matrix U at row i, column k;

$y_i$ represents an element of the right hand side matrix Y at row i;

$w_k$ represents a diagonal element of the singular value matrix W at column k;

$v_{jk}$ represents an element of the basis matrix V at row j, column k; and $c_j$ represents the $j^{th}$ element of the parameter coefficient matrix C, formed by the linear combination of columns of the basis matrix V using as coefficients the set of $d_k$ dot product results from equation (49).

Equation (49) represents an embodiment of step (ee), equivalent to the matrix product within the parentheses in equation (48). Equation (50) represents an embodiment of step (ff), equivalent to the matrix product within the parentheses in equation (48).

It is apparent from equation (49) why a singular or nearly singular system of linear equations may produce an unstable solution which may not be representative of the true parameter coefficients. If the value of $w_k$ is substantially close to zero, the reciprocal of $w_k$ is exceedingly large, so the value of $d_k$ determined by equation (49) is exceedingly large, and the contribution of the corresponding component to the linear combination in equation (50) overwhelms the other components of the linear combination of basis vectors. The columns of the basis matrix V corresponding to the same column $w_k$ with values near zero represent a vector basis for the nullspace. Referring to equation (46) for the general solution, the scalars $g_k$ of equation (46) are equivalent to the $d_k$ determined by equation (49) corresponding to $w_k$ with values near zero, and the $H_k$ of equation (46) are equivalent to the columns of the basis matrix V corresponding to $w_k$ with values near zero. A system of linear equations that is singular or nearly singular may result in a solution embodied by equation (46) wherein the homogeneous solution components $g_k H_k$ overwhelm the particular solution C. Therefore, it is necessary to control the contribution of the nullspace components of the solution, and the singular value decomposition method provides a way to do so.

Step (dd) comprises eliminating the nullspace basis vectors from the linear combination which determines the solution. In one embodiment of step (dd), the dot product value $d_k$ determined in step (ee) by equation (49) is set to a value of zero if the corresponding singular value $w_k$ is substantially near zero, as expressed in the following equation using the same notation as equation (49):

$$d_k = \begin{cases} 0 & \text{for } w_k < \varepsilon \\ \sum_{i=1}^{M} \frac{u_{ik} y_i}{w_k} & \text{for } w_k \geq \varepsilon \end{cases} \quad \text{for } k = 1, 2, \ldots, N \qquad (51)$$

where the value of $\varepsilon$ represents a threshold limit for determining if $w_k$ is substantially near zero; the case for $w_k < \varepsilon$ is an embodiment of step (dd); and the case for $w_k \geq \varepsilon$ is an embodiment of step (ee) which is equivalent to equation (49). Assigning a value of zero to $d_k$ corresponding to $w_k < \varepsilon$ in equation (51) has the effect of eliminating the corresponding components from the linear combination in the summation of equation (50), thereby controlling the contribution of the nullspace components of the solution.

In another embodiment of step (dd), the components $(d_k v_{jk})$ for each k corresponding to $w_k < \varepsilon$ are excluded from the summation in equation (50), thereby controlling the contribution of the nullspace components of the solution.

The value of the near-zero threshold $\varepsilon$ is chosen depending on characteristics of the system of linear equations. In practice, the value of the limit $\varepsilon$ depends on various factors, including but not limited to the largest singular value, the precision of the numerical representation of $w_k$, and the columns in the basis matrix V. In one embodiment, the limit $\varepsilon$ for $w_k$ substantially near zero may be assigned a value representative of an estimate of the limit of round-off error, according to the following expression:

$$\varepsilon = N \times (\text{machine epsilon}) \times \max(w_k) \qquad (52)$$

where N is the number of columns in the basis matrix V; (machine epsilon) represents the precision of the numerical representation of $w_k$; and $\max(w_k)$ represents the maximum singular value $w_k$ in the singular value matrix W. In another embodiment, the value of the limit $\varepsilon$ is assigned a value much larger than equation (52) by as much as several orders of magnitude in order to eliminate components that substantially approximate homogeneous solutions as identified by the singular value decomposition. In yet another embodiment, the limit $\varepsilon$ is chosen sufficiently large in order to eliminate components of the solution that do not contribute substantially to reducing the $\chi^2$ best-fit measure of the solution.

In another embodiment of the present invention, the SVD determined in step (cc) is used to estimate a measure representative of a probable error of one or more of the parameter coefficients of the solution. The probable error is determined by relationships well known in the art (W. Press et al., *Numerical Recipes in C*, Cambridge University Press, 1988, pp. 556-557), and may be determined according to the following expression:

$$\text{probable error} = \sqrt{\sum_{k=1}^{N} \left(\frac{v_{jk}}{w_k}\right)^2} \quad \text{for the } j^{th} \text{ parameter coefficient } c_j \qquad (53)$$

where
$w_k$ represents a diagonal element of the singular value matrix W at column k; and
$v_{jk}$ represents an element of the basis matrix V at row j, column k.

If a standard deviation error of the driving-point motion signals is known or estimated, then the elements of the design matrix Z and the right-hand side matrix Y may be weighted by the reciprocal of the corresponding standard deviation error estimate, to produce an error-weighted design matrix and an error weighted right-hand side matrix. The probable error determined from the SVD of the error-weighted design matrix represents an estimate of a standard deviation error of the corresponding parameter coefficient. If the design matrix and the right-hand side matrix are not error-weighted, the probable error determined from the SVD does not represent a standard deviation error, but does represent a relative error estimate, which is representative of the relative errors of the various parameter coefficients.

It is useful to estimate a measure of the probable error of the parameter coefficients in order to measure the accuracy and reliability of the elastic property values determined by the methods of the present invention.

In another embodiment, the SVD determined in step (cc) is used to determine a rank, a nullity, and/or a condition number of the system of linear equations. The nullity is the number of nullspace basis vectors determined in step (dd) corresponding to $w_k < \varepsilon$ as described for equation (51). The rank is the number of basis vectors which are not nullspace basis vectors; the rank plus the nullity is equal to the total number of solution basis vectors N (which is also the same as the number of columns in the basis matrix V, and the same as the number of parameter coefficients in the C matrix). The condition number is the ratio of the largest singular value to the smallest singular value; a large condition number represents indicates that the system of linear equations is ill-conditioned. If the smallest singular value is zero valued, the condition number is infinite and the matrix is singular. It is useful to determine the rank, the nullity, and/or the condition number as a measure of the degeneracy of the particular differential equation model used to form the system of linear equations. Identifying which combinations of the model basis functions are components of the nullspace vectors is helpful for selecting a differential equation model with a lower condition number and therefore less degeneracy.

In another embodiment of the method for solution of the system of linear equations, a value is determined for the goodness of fit of the solution, by evaluating the chi-squared merit function $\chi^2$ according to equation (42), substituting the actual solution C into equation (42). It is useful to have a measure of the goodness of fit, to measure relative reliability of the elastic properties determined from the solution, or to compare solutions for various differential equations models or for various elastic materials.

Solution by Other Methods

The best-fit solution of the system of linear equations may be determined by a method that uses additional information about the unknown parameter coefficients. For many elastic materials, a range of values that is reasonably expected for the value of one or more of the parameter coefficients may be known in advance. For example, the differential equation model may be designed such that the first-order stiffness coefficient $k_1$, the first-order viscosity coefficient $b_1$, and/or the inertial coefficient m are known to be positive quantities having a value greater than zero. A reasonably expected range of values within an order of magnitude or better is typically known for one or more of the parameter coefficients, especially for repeated measurements of the same or similar materials. There are various methods known by those skilled in the art which may be used for solving the system of linear equations that incorporates the known probable values and/or probable uncertainties by use of a priori covariances of one or more of the unknown parameter coefficients.

Another method for solution of the system of linear equations is the method of Kalman filtering which is well known by those skilled in the art. In one embodiment, the system of linear equations is represented by a set of basis function signals and a right-hand side signal, wherein each basis function signal represents a basis function value of the differential equation model as a function of time, and the right-hand side signal represents the right-hand side value as a function of time. Kalman filtering is a method for analyzing the set of basis function signals and the right-hand side signal to determine a best-fit parameter estimate as a function of time for one or more of the parameter coefficients.

4. The Elastic Properties

The systems and methods of the present invention determine parameter coefficients corresponding to a system of linear equations based on a measured driving-point response. The parameter coefficients so determined are representative of one or more elastic properties of the elastic material. The elastic properties comprise one or more of the following properties: stiffness, viscosity, shear-wave speed, shear modulus, inertial mass density.

The stiffness properties comprise one or more of the following properties: first-order stiffness, second-order stiffness, third-order stiffness, etc. or higher-order stiffness coefficients. The first-order stiffness is equivalent to the linear stiffness for small-amplitude driving-point motions which approximate the response of a linear elastic force obeying Hooke's law, even though the first-order stiffness may be determined using a driving force exceeding the small-amplitude approximation limit.

The first-order stiffness is representative of a combination of the shear modulus and Poisson's ratio, approximated by the relationship for static stiffness:

$$K = \frac{4Gr_0}{1-\mu} \quad (54)$$

where K represents stiffness, G represents shear modulus, $r_0$ represents the radius of a circular area equivalent to the defined surface area size of the driving element, and $\mu$ represents Poisson's ratio.

The viscosity properties comprise one or more of the following properties: first-order viscosity, second-order viscosity, third-order viscosity, etc. or higher-order viscosity coefficients. The first-order viscosity is equivalent to the linear viscosity for small-amplitude driving-point motions.

Other measures representative of viscosity are also used in the art. Quantitative measures representative of viscosity, damping, or dissipation of elastic energy comprise the following: viscosity, damping capacity, constant of internal friction, hysteretic constant, specific damping capacity, logarithmic decrement, elastic phase constant, coefficient of internal friction, damping modulus, resonance-amplification factor, damping factor, specific damping energy, stress-strain phase angle, loss angle, specific dissipation function, relaxation time, creep function, relaxation function, attenuation, absorption coefficient, and quality factor Q. These properties are interrelated and can generally be converted from one form of expression to another.

The nonlinear stiffness and viscosity coefficients (second-order, third-order, etc.) are representative of the degree of nonlinearity of the elastic material. The nonlinear stiffness coefficients represent a quantitative measure of the degree of nonlinear stiffness. The nonlinear viscosity coefficients represent a quantitative measure of the degree of nonlinear viscosity. The relationships of the even-order and odd-order coefficients represent a measure of the symmetry or asymmetry of the corresponding stiffness or viscosity. The degree of nonlinear symmetry or asymmetry represents an elastic property of the material.

Each of the one or more properties so determined in relation to the driving force may be converted to a value of the property expressed as per unit area by dividing the value of the property by the defined area size of the contact surface area where the driving force is exerted. The driving force may be expressed as a driving stress by dividing the driving force by the defined area size of the contact surface area where the driving force is exerted.

One or more elastic properties of a heterogeneous elastic material may be determined by separately determining elastic properties at each of a plurality of locations on or within a body of the material, thereby determining a spatial variation of the elastic properties.

An advantage of the present invention is that linear (i.e. first-order), small-amplitude properties may be determined using large-amplitude, nonlinear driving-point motions. Another advantage of the present invention is that compressional properties may be determined separately from de-compression or extensional properties, by segmenting the driving-point response into compressive stroke segments or de-compressive stroke segments, and analyzing the compressive stroke segments separately from the de-compressive stroke segments. Another advantage of the present invention is that elastic properties may be determined as a function of time during the application of the driving force, and as a function of the fundamental frequency of the applied driving force.

Other useful elastic properties determined by the systems and methods of the present invention are described in detail in Example 1 herein.

5. Determining Acceleration, Velocity, and Displacement from Measured Driving-Point Motion The driving-point motions representing the response of the elastic material are the acceleration, the velocity, and the displacement of the contact surface area where the driving force is exerted. Any one of these motions can be used to determine the other two. Integration of the acceleration produces the velocity. Integration of the velocity produces the displacement. The time derivative of the displacement produces the velocity. The time derivative of the velocity produces the acceleration. Given any one of the three types of motion signals, the other two can be determined by appropriate integration or differentiation.

In one embodiment of the present invention, an acceleration sensor rigidly coupled to the driving element of a dynamic actuator produces an acceleration signal representative of the driving-point acceleration. In this embodiment, the driving-point velocity is determined by integration of the measured acceleration, and the driving-point displacement is determined by integration of the velocity.

The integration introduces errors, and the integration error must be substantially removed for the integrated signals to be useful.

5.1 Integration Error

It is known by those skilled in the art that integration of a real signal introduces accumulating errors that increase as the length of the integration interval increases. One type of error is cumulative measurement error in the signal, such that the signal being integrated is not a perfectly accurate representation of the true quantity being measured. Another type of error is caused by limited precision of the integration process. For example, numeric integration of a digital signal is subject to accumulating round-off errors caused by the finite precision of the digital representation of the signal.

It is also known in the art that the integration errors may tend to be statistically random, resulting in a cumulative error which is substantially similar to what is known as a random walk. The cumulative error therefore may include a wide range of component frequencies, including frequencies lower than, similar to, and higher than the frequencies representing the signal being integrated.

Integration also introduces an unknown constant value (i.e. a DC shift, or zero-frequency component) to the integrated signal, because the integrated signal's initial value at the beginning of the integration interval is typically unknown. This unknown initial value is another integration error in the integrated signal.

If acceleration, velocity, or displacement signals containing substantial integration error are analyzed to determine elastic properties of a material, the elastic properties so determined may not be representative of the actual elastic properties of the material. If the degree of integration error is large, the elastic properties so determined may be substantially meaningless.

In practice, I have found that integration of measured driving-point acceleration signals produces velocity signals that are a poor representation of the actual velocity even for short time periods, due to accumulated integration error comprising a broad range of frequency components. Double integration of a measured driving-point acceleration signal sometimes produces a displacement signal with integration error that substantially exceeds the actual displacement.

For these integrated signals to be useful, it is essential to substantially remove the integration error. For the elastic properties derived from these integrated signals to be meaningful, the method used to remove the integration error must substantially preserve the phase relationships and amplitude relationships between the acceleration, the velocity, and the displacement signals.

There are known methods typically used in the art to estimate and remove integration errors. One method is to fit a smooth curve to the integrated signal, using a smooth function such as a low-degree polynomial function, the low-degree polynomial typically being a constant, a first-degree, or a second-degree polynomial. The polynomial fit represents an approximation of a long-term average of the signal over a number of cycle periods. The polynomial fit is assumed to be an estimate of the average integration error over the interval being fit, and the estimated error is removed by subtracting the polynomial fit from the integrated signal. Another procedure used in the art is to filter the integrated signal with a high-pass filter or band-pass filter to remove the components of the integration error that occur at frequencies outside the frequency band of the signal.

Existing methods are limited to estimating and attenuating the low-frequency components of the integration error, and are unable to estimate or attenuate the broad-band range of frequencies present in a random-walk integration error. The existing methods can also introduce relative phase errors and relative amplitude errors which result in loss of accuracy in the determination of elastic properties.

5.2 Harmonic Components in the Response of Elastic Materials

A object of the present invention is to take advantage of characteristics of the driving-point motions of elastic materials to enable a method to estimate and attenuate broadband errors in driving-point motion signals and in driving force signals—including measurement errors and/or broadband random-walk integration errors—while substantially preserving the phase relationships and the amplitude relationships of the components of the integrated signal that are representative of the actual response of the material. The components representative of the actual response are the harmonics of the driving force, and the transient response.

An elastic material which is deformed by a driving force will respond with driving-point motions comprising component frequencies at harmonics of the frequency of the applied force. The response of a linear elastic material comprises the same component frequencies as the driving force. The response of a nonlinear elastic material is an anharmonic response comprising a superposition of a plurality of harmonic frequency components at harmonics of the frequency components of the driving force. There is no substantial response at any other frequencies, except for the transient response having components at the natural modal frequencies.

If the frequency components of the dynamic force applied to the material are known, then any component frequency in the driving-point motion signal which is not a harmonic of the known dynamic force frequencies can be assumed to be error or noise, except for the transient components at the natural modal frequencies.

The driving force exerted by a controlled dynamic actuator is controlled to be similar to a continuous-phase reference signal which is a known signal. Based on knowledge of the response characteristics of an elastic material, it may be assumed that the driving-point motion of the contact surface area has component frequencies at harmonics of the known continuous-phase reference signal. In the present invention, the error components of the signal are estimated by attenuating the known harmonic components at harmonics of the reference signal. The frequencies of the transient component may also be attenuated, if present, to improve the error estimate. The estimated error is subtracted from the signal to produce an error-corrected signal.

This error estimation and attenuation method may be described mathematically as follows:

Let $\phi(t)$ be the angular phase function of a known continuous-phase reference signal $P(t)$ used by a controlled dynamic actuator to control a driving-force:

$$P(t)=A(t)e^{i(\phi(t))} \tag{55}$$

where
- A(t) represents an amplitude envelope function of the known reference signal;
- φ(t) represents the angular phase function of the known reference signal;
- $i=\sqrt{-1}$; and
- $e^{i\theta} = \cos\theta + i\sin\theta$.

Based on the anharmonic response of real elastic materials, the driving force and the driving-point motion are assumed to comprise the superposition of components at frequencies that are harmonics of the reference signal, the components therefore having angular phase functions kφ(t), where k is a positive integer:

$$R(t) = \sum_{k=1}^{\infty} a_k(t) e^{i(k\varphi(t)+\delta_k)} \quad (56)$$

where
- R(t) represents driving-point response signal, comprising a driving-point acceleration, driving-point velocity, driving-point displacement, or driving force signal;
- $a_k(t)$ represents the amplitude envelope function of the $k^{th}$ harmonic component of the signal;
- φ(t) represents the angular phase function of the known reference signal;
- kφ(t) represents the angular phase function of the $k^{th}$ harmonic component, which is a positive integer multiple k of the phase function of the reference signal;
- $\delta_k$ represents a phase shift constant of the $k^{th}$ harmonic component of the driving-point motion signal;
- k represents the harmonic number, a positive integer 1, 2, 3 . . . .

In practice for real materials, the amplitude functions $a_k(t)$ become very small as k increases, so that R(t) can be accurately approximated by the finite sum of n harmonics:

$$R(t) \approx \sum_{k=1}^{n} a_k(t) e^{i(k\varphi(t)+\delta_k)} \quad (57)$$

where $a_k(t) \approx 0$ for k>n.

The number of harmonics n is chosen sufficiently large to achieve the desired accuracy in the summation.

In addition to the driving-point motion signals and the driving force signal, other signals representative of the motion or output of the controlled dynamic actuator can also be accurately approximated by the superposition of harmonic components represented by equation (72). Examples of such signals comprise a reaction mass motion signal, and a relative displacement signal representative of the relative displacement of the reaction mass relative to the baseplate.

The measured driving-point response signals contain measurement errors. The driving-point motion signals formed by integration contain integration errors. The known signal comprises the sum of the unknown errors and the "true" signal, which is assumed to be a superposition of harmonics described by R(t):

$$S(t) = R(t) + E(t) \quad (58)$$

where S(t) represents the known driving-point response signal, R(t) represents the "true" response signal, and E(t) represents the measurement error and/or integration error.

The value of the continuous-phase reference signal P(t) is known, and the value of the driving-point response signal S(t) is known, being determined by measurement or by integration or differentiation. The values of the "true" response signal R(t) and of the error signal E(t) are unknown. The object is to estimate the unknown error E(t), so that it may be subtracted from the known signal S(t) to produce a more accurate representation of the "true" response signal R(t).

However, the phase functions kφ(t) of the harmonic components of the "true" motion signal R(t) are known, because the material is assumed to respond at harmonics of the driving force. The parts of R(t) which are not known are the amplitude functions $a_k(t)$ and the phase shifts $\delta_k$. The known signal S(t) is filtered to selectively attenuate components having harmonic phase functions substantially equal to kφ(t), which substantially attenuates the true motion signal R(t). The remaining components represent a broad-band estimate of the measurement and/or integration error E(t).

Therefore, the measurement error or integration error E(t) can be estimated based on knowledge of the phase functions of the harmonic components of the "true" response signal R(t) having phase functions kφ(t). The knowledge of the phase functions is based on characteristics of the physical response of real elastic materials, which respond at harmonics of the driving force, the driving force being similar to the reference signal. These principles can be used to estimate not only integration error, but also other errors, such as measurement errors, in any driving-point motion signal or any driving-point force signal. Except for the frequency components of the transient component of the signal, any components of a driving-point signal at frequencies other than harmonics of the driving force may be considered to be not physically realizable in an elastic material, and these non-harmonic components may therefore be assumed to represent error. The error may comprise measurement error, integration error, or any other noise or error which is not physically realizable in an elastic material.

An object of the present invention is to estimate the error E(t) in an driving-point response signal, based on knowledge of the phase functions of the harmonic components of the "true" response signal R(t). It is an object of this invention to estimate an integration error which includes a broad range of frequency components. It is useful to include a broad range of frequency components in the estimated integration error because real integration errors encountered in practice typically represent a statistical random walk which comprises a broad range of frequency components. It is also an object of the present invention to remove the estimated error from anharmonic driving-point response signals while substantially preserving the amplitudes and phases of the plurality of harmonic components of the "true" response signal R(t). It is useful to preserve these harmonic components because the relationships between the amplitudes and phases of the harmonic components of driving-point motions carry information about the nonlinear response of a real elastic material. If only the fundamental frequency component is preserved, attenuation or distortion of the higher harmonic components results in loss of information about the elastic properties of the material.

It is an object of the present invention to estimate and to attenuate a broad-band estimate of integration errors and/or measurement errors from the driving-point motion signals and from the driving force signal. These errors are estimated using a filter which I call a fractional-cycle-interval filter, and attenuated by subtracting the estimated error from the driving-point motion signal using an error attenuator.

The fractional-cycle-interval filter is useful for estimating an error component in an anharmonic driving-point response signal while substantially preserving the amplitude and phase relationships of the plurality of harmonic frequency components of the anharmonic response.

5.3 A Fractional-Cycle-Interval Filter and an Error Attenuator

I disclose in the present invention a system and a method to filter an input signal to either attenuate or preserve selected harmonic components that are harmonics of a known continuous-phase signal, referred to herein as a phase reference signal. I call this filter a fractional-cycle-interval filter, the filter method comprising the following:

(pp) determining a series of time values at equal intervals of phase of the phase reference signal, wherein the equal intervals of phase are fractional-cycle intervals;

(qq) sampling the input signal at the time points represented by the series of time values so determined, to produce a phase-sampled signal;

(rr) filtering the phase-sampled signal so produced, using a filter adapted to substantially attenuate or preserve each of one or more selected harmonic frequency components at harmonics of the continuous-phase signal, wherein the harmonics of the continuous-phase signal are substantially equal to harmonic multiples of the reciprocal of one phase-cycle period, to produce a filtered phase-sampled signal;

(ss) re-sampling the filtered phase-sampled signal so produced, at equal intervals of time, based on the series of time values determined in step (pp), above, thereby producing a fractional-cycle-interval filtered signal.

The filtered phase-sampled signal produced in step (rr) and the fractional-cycle-interval filtered signal produced in step (ss) are estimated error signals representative of an error component of the input signal. An error attenuator method to attenuate the estimated error component of the input signal comprises the following:

(tt) attenuating the estimated error component of the input signal by subtracting the estimated error signal from the input signal to produce an error-corrected signal.

The fractional-cycle-interval filter has two distinct inputs: an input signal to be filtered (symbolized herein by S(t)), and a phase reference signal (symbolized herein by P(t)). The phase reference signal comprises a continuous-phase signal having a phase function symbolized by $\phi(t)$.

In step (pp) the phase of the phase reference signal is analyzed to determine the time values of points at equal intervals of phase. In particular, the equal interval of phase is a fractional-cycle interval, such that each cycle is evenly divided into an integral number of equal intervals of phase. Each equal interval of phase is equal to one-$N^{th}$ of one cycle (a fractional-cycle interval):

$$\Delta\varphi = \frac{2\pi}{N} \tag{59}$$

$$\varphi_k = k\Delta\varphi = k\frac{2\pi}{N}, k = 0, 1, 2, 3, \ldots \tag{60}$$

$$t_k = \text{time at which } \phi(t_k) = \phi_k \tag{61}$$

where $\Delta\phi$ represents the phase interval equal to one-$N^{th}$ of one cycle (a fractional-cycle interval), expressed here as a phase-interval in radians;

N represents an integer constant, representing the number of intervals per cycle;

$\phi_k$ represents the phase value of the ending point of the $k^{th}$ interval;

$t_k$ represents a series of time values at equal intervals phase of the phase function $\phi(t)$, such that $\phi(t_k)=\phi_k$.

The number of intervals per cycle (symbolized by N) may be any positive integer, including odd or even integers. The number of intervals per cycle, N, is selected to optimize the resolution and performance of the filter, with larger N producing a higher-resolution phase-sampled signal but larger N also producing a larger data volume to be filtered.

In one embodiment, the phase reference signal P(t) is represented by a known set of parameters that define the phase function $\phi(t)$, and the series of time values $t_k$ of the phase function $\phi(t)$ are determined analytically by evaluating the known set of parameters to find the series of times $t_k$ such that $$\varphi(t_k) = k\frac{2\pi}{N}.$$

The series of time values $t_k$ are the roots of the equation $$\varphi(t) - k\frac{2\pi}{N} = 0. \tag{62}$$

The roots $t_k$ of this equation may be determined analytically for simple phase functions, or the roots $t_k$ may be determined by a numerical root finding method, including but not limited to a bracketing bisection method, a Newton-Ralphson method, a hybrid combination of bisection and Newton-Ralphson methods (Press et al., *Numerical Recipes In C*, Cambridge University Press, 1988, pp. 255-289), and any of various other root finding methods well known by those skilled in the art.

In one embodiment, the phase function is a monotonic function of frequency, in which case there is only one root of equation (62) for each value of the index k. Each of the single roots is found efficiently in sequence by using the prior root as a lower bound for bracketing the next root.

In another embodiment, the values of the phase signal $\phi(t)$ are determined by evaluating the arctangent of the imaginary part of the phase reference signal divided by the real part of the phase reference signal:

$$\varphi(t) = \arctan\left(\frac{\text{Im}[P(t)]}{\text{Re}[P(t)]}\right) \tag{63}$$

where Re[P(t)] is the real part of P(t), Im[P(t)] is the imaginary part of P(t), and Im[P(t)] is the Hilbert transform of Re[P(t)]. In this embodiment, the arctangent function results in phase values from $-\pi$ to $+\pi$ which repeat with each cycle. By keeping account of zero-crossings of P(t), it is possible to unwrap the arctangent phase to produce a continuous phase function $\phi(t)$. The series of time values $t_k$ are determined by tracking the amplitude of the continuous-phase function $\phi(t)$, and detecting the times at which the amplitude is an integral multiple of the fractional-cycle-interval:

$$\varphi(t) = k\frac{2\pi}{N}.$$

In another embodiment, the phase value $\phi_k$ is subtracted from the phase signal $\phi(t)$ to produce a difference signal ($\phi(t)-\phi_k$), and the time value $t_k$ is determined by detecting the zero-crossing of the difference signal using a zero-crossing detector. The value of the index k is incremented after the zero-crossing is detected, to produce a new phase value $\phi_{k+1}$ which is used to find the next zero-crossing.

In step (qq), the input signal S(t) is sampled at the series of time points $t_k$ determined in step (pp), thereby producing a phase-sampled signal $S_k$. The phase-sampled signal is a series of sample values representing the amplitude of the input signal at the series of time points $t_k$ determined in step (pp): $S_k=S(t_k)$. This sampling may also be described as a transformation, the sampling transforming input signal S(t) from a function of time to a function of the phase of the phase reference signal.

In one embodiment, the input signal S(t) is a digital signal, and the sampling of the input signal S(t) comprises interpolating the digital values representing the input signal, to interpolate values at the series of time points $t_k$ determined in step (pp). The interpolation is done by any of various interpolation methods well known in the art, including but not limited to: linear interpolation, Lagrange interpolation, polynomial interpolation, cubic spline interpolation, and trigonometric interpolation such as Fourier methods or sinc-function interpolation (e.g. Shannon reconstruction). In another embodiment, the input signal is an analog signal, and the sampling is done by an analog-to-digital converter which samples at the series of time points $t_k$ determined in step (pp).

In step (rr), the phase-sampled signal is filtered to attenuate one or more harmonic frequency components which are harmonics of the phase reference signal, by applying a filter having a response with attenuation notches (zeros) at a selected set of harmonic frequencies substantially equal to harmonics of the reciprocal of one phase-cycle. Because the phase-sampled signal is sampled at equal intervals of phase, the "frequency" components of the phase-sampled signal are not temporal frequencies, but are instead pseudo-frequencies which may be expressed in units of cycles-per-radian. One phase-cycle is equivalent to the phase sample interval multiplied by N the number of phase samples per cycle, as can be expressed by the following series of equations:

$$\text{one phase-cycle} = N\Delta\varphi \qquad (64)$$
$$= N\left(\frac{2\pi}{N}\right)$$
$$= 2\pi \text{ radians.}$$

In other words, the length of one cycle of the continuous-phase signal is represented by a sequence of N sample points of the phase-sampled signal regardless of the temporal frequency of the continuous-phase signal, where N is the number of samples per cycle used for forming the phase-sampled signal. Harmonics of the continuous-phase signal occur in the phase-sampled signal at pseudo-frequencies that are harmonics of the reciprocal of N sample intervals, and these harmonic components can be expressed in terms of cycles per radian:

$$\frac{1}{2\pi}, \frac{2}{2\pi}, \frac{3}{2\pi}, \ldots, \frac{i}{2\pi} \text{ cycles per radian,} \qquad (65)$$

or in terms of cycles per phase-sample-interval:

$$\frac{1}{N}, \frac{2}{N}, \frac{3}{N}, \ldots, \frac{i}{N} \text{ cycles per phase-sample-interval,} \qquad (66)$$

where i represents the harmonic multiple number.

Because the phase-sampled signal is sampled at fractional-cycle intervals, simple digital filters are used that have a response with attenuation notches (zeros) at harmonics of the reciprocal of N sample intervals.

In one embodiment, a very simple two-point filter is used to attenuate all odd-numbered harmonic components of the phase-sampled signal, by forming the average of two points spaced one-half cycle apart:

$$E_k = \frac{(S_{k-4} + S_{k+4})}{2}, \text{ for } N = 16, \qquad (67)$$

where
- $E_k$ is the filter output at the $k^{th}$ point of the phase-sampled signal series $S_k$;
- $S_{k-4}, S_{k+4}$ are two points in the phase-sampled signal series that are spaced at an interval of one-half cycle apart, which in this case is eight phase-intervals in the phase-sampled series; and
- $S_k = S(t_k)$ is the phase-sampled signal series, sampled at points $t_k$ such that $$\varphi(t_k) = k\frac{2\pi}{16}.$$

In this embodiment N=16, so the phase-sampling interval is $\Delta\phi=\pi/8$ radians, and the interval from (k−4) to (k+4) is a phase interval equal to $\pi$, which is one-half cycle. The amplitude response of this half-cycle filter has attenuation notches (zeros) at all odd-numbered harmonics of the continuous-phase signal.

This filter is an example (for N=16) of a general class of two-point filters with points spaced one-half cycle apart, which are used to attenuate all odd-numbered harmonic components of the input signal. Filters in this class have response functions with zeros at all odd-numbered harmonics, which are represented in the phase-sampled signal as phase-sample pseudo-frequencies equal to $$\frac{1}{2\pi}, \frac{3}{2\pi}, \frac{5}{2\pi}, \ldots,$$

in units of cycles-per-radian. A general expression for this one-half cycle filter is as follows:

$$E_k = \frac{(S_{k-N/4} + S_{k+N/4})}{2}, \text{ for } N \text{ evenly divisible by 4.} \qquad (68)$$

where
- $E_k$ is the filter output at the $k^{th}$ point of the phase-sampled signal series $S_k$;
- $S_{k-N/4}, S_{k+N/4}$ are two points in the phase-sampled signal series that are spaced at an interval of one-half cycle apart, which in this example is N/2 phase-intervals in the phase-sampled series; and $S_k = S(t_k)$ is the phase-sampled signal series, sampled at points $t_k$ such that $$\varphi(t_k) = k\frac{2\pi}{N},$$

where N is a positive integer evenly divisible by 4.

The output of the half-cycle filter lags one-quarter cycle after the input. The effect of the odd-numbered harmonic filter represented by equation (68) is to attenuate the frequency components of the phase-sampled signal that are odd-numbered harmonics of the continuous-phase signal.

A filter attenuating the odd-numbered harmonics is useful because the odd-numbered harmonics dominate the anharmonic driving-point response of certain elastic materials. Elastic materials having a substantially linear elastic force response and a substantially nonlinear viscous force response tend to produce an anharmonic driving-point response comprising a superposition of odd-numbered harmonic frequency components.

Another embodiment of a filter having a response with attenuation notches (zeros) at harmonics of the reciprocal of N sample intervals is a moving-average filter with a window length equal to one cycle:

$$E_k = \frac{1}{65} \sum_{i=k-32}^{k+32} S_i, \text{ for } N = 65, \tag{69}$$

where $E_k$ is the filter output at the $k^{th}$ point of the phase-sampled signal series $S_k$;

$S_i$ are sequential points in the phase-sampled signal.

In this example N=65, so the phase-sampling interval $\Delta\phi = 2\pi/65$. The amplitude response of this has zeros at the first 64 harmonics:

$$\frac{1}{2\pi}, \frac{2}{2\pi}, \frac{3}{2\pi}, \ldots, \frac{64}{2\pi}$$

in units of cycles-per-radian.

A general class of filters having a response with attenuation notches (zeros) at harmonics of the reciprocal of an integral number of sample intervals can be expressed as follows:

$$E_k = \sum_{i=-m}^{+m} w_i S_{k+i}, \tag{70}$$

where $E_k$ is the filter output at the $k^{th}$ point of the phase-sampled signal series $S_k$;

$S_{k+i}$ are a series of points in the phase-sampled signal, sampled at points $t_k$ such that $\phi(t_k) = 2\pi/N$, where N is a positive integer;

$w_i$ are a set of filter coefficients applied to the $S_{k+i}$ phase-sampled signal, there being a total of 2m+1 filter coefficients, where m is a positive integer.

It is known to those skilled in the art that there are various filter types and filter design methods for selecting a set of filter coefficients $w_i$ that can be used to produce a filter having this type of response—with attenuation notches (zeros) at harmonics of the reciprocal of an integral number of phase-sample intervals. For example, Hamming, Hanning, Blackman, Blackman-Harris, and other filter types are well known in the art, and there are many well known filter design methods for selecting other types of optimized filter coefficients.

A characteristic of the harmonic filter used to filter the phase-sampled series in step (rr) is that the filter response has attenuation notches (zeros) at selected harmonics of the reciprocal of N phase-sample intervals, where N is the number of samples per cycle of the continuous-phase signal. When a filter having this characteristic is applied to a phase-sampled signal which is sampled at fractional-cycle-intervals as described, the combined result of the phase-sampling and filtering operation is to substantially attenuate selected harmonic components which are harmonics of the known continuous-phase signal.

In another embodiment, the filter in step (rr) can be adapted to either attenuate or preserve one or more selected harmonic multiples of the phase reference signal, such that the filter response function comprises a magnitude response either substantially equal to zero or substantially equal to unity at each of the selected harmonic multiples.

In one embodiment, the filter in step (rr) is applied by convolution of a filter operator with the phase-sampled signal. This convolution may be performed directly in the phase-sampled domain, or by Fourier transforming the phase-sampled signal (e.g. by an FFT or DFT) to a pseudo-frequency domain and performing the filtering in this pseudo-frequency domain.

The filtered phase-sampled signal produced in step (rr) represents the estimated error component of the input signal, wherein the estimated error component is represented by a phase-sampled estimated error signal. This phase-sampled estimated error signal produced in step (rr) may be used without further modification, or it may be converted back into a function of time in step (ss).

In step (ss), the filtered phase-sampled signal produced in step (rr) is re-sampled at equal intervals of time, to convert the phase-sampled signal back into a function of time. In one embodiment, the re-sampling is be done by interpolation between the phase-interval samples of the phase-sampled signal, to determine an interpolated signal amplitude value at equal intervals of time. The interpolation may be done by any of various interpolation methods known in the art, including but not limited to: linear interpolation, Lagrange interpolation, polynomial interpolation, cubic spline interpolation, trigonometric interpolation, and sinc-function interpolation (e.g. Shannon reconstruction).

The filtered phase-sampled signal produced in step (ss) represents the estimated error component of the input signal, wherein the estimated error component is represented by a signal uniformly sampled in time.

This fractional-cycle-interval filter may be applied efficiently to a collection of input signals that all share the same phase function $\phi(t)$, by determining the series of time values in step (pp) only once, and using this same series of time values repeatedly in steps (qq) and (rr) for each of the input signals in the collection. The interpolation in steps (qq) and (ss) may also be applied efficiently to a collection of input signals that all share the same phase sampling interval, by determining a series of time intervals upon which to apply an interpolation function, and using these same time intervals repeatedly for interpolation in step (qq) and/or step (ss).

For example, all the three driving-point motion signals—acceleration, velocity, and displacement—comprising a driving-point response can be filtered using the same phase reference signal, which is representative of the continuous-phase reference signal used to control the actuator output force. A series of time values $t_k$ are determined once in step (pp), and the series so determined is used repeatedly to apply a fractional-cycle interval filter to each of the three driving-point motion signals—acceleration, velocity, and displacement. Also, when a controlled dynamic actuator is used to apply a dynamic force to a collection of different substrate materials or to a collection of different locations on a substrate material, it is typical practice to select a reference signal to use repeatedly for repeated application of the same dynamic force. In this case, the same series of time values $t_k$ may be used repeatedly for each of the signals in the collection that share the same phase reference signal.

The fractional-cycle-interval filter is useful because it effectively attenuates selected components of the input signal that are harmonics of the instantaneous frequency of a known continuous-phase function having a known phase function $\phi(t)$. Because the input signal is sampled at fractional-cycle intervals, simple digital filters can be used to selectively either attenuate or preserve the selected harmonic components, the filters having a response with either zeros or unity gain at the selected harmonic components.

Because the filter in step (rr) has notches (zeros) at the selected harmonic components, when the error estimate produced by the fractional-cycle-interval filter is subtracted from the input signal, the amplitude and phase relationships of these same harmonic components in the input signal are substantially preserved.

The process employed by the present invention for estimating and attenuating measurement error, integration error, or other error in a driving-point response signal is to estimate the error component of the signal by filtering the signal using a fractional-cycle-interval filter to produce an estimated error signal, and to attenuate the error by subtracting the estimated error signal from the driving-point motion signal to produce an error-corrected driving-point motion signal.

The process for estimating and attenuating the error may be described by the following mathematical summary:

The known signal $S(t)$ is the combination of the "true" response signal $R(t)$ and the unknown error $E(t)$:

$$S(t)=R(t)+E(t). \tag{58}$$

The unknown error $E(t)$ is estimated by filtering the known signal $S(t)$ to attenuate the "true" signal $R(t)$ which consists of harmonics of known phase function $\phi(t)$, the attenuation accomplished by a fractional-cycle-interval phase filter $F_{\phi(t)}$:

$$E(t) = F_{\varphi(t)}[S(t)] = \sum_{i=-m}^{+m} w_i S(t_{k+i}), \tag{71}$$

where $t_k$ is such that $$\varphi(t_k) = k\frac{2\pi}{N}, \quad k = 0, 1, 2, 3, \ldots$$

where $w_i$ are discrete filter coefficients for a discrete filter having a response function with notches (zeros) at harmonics of the inverse of the phase sample interval. The filter is applied to phase-sampled signal $S(t_k)$ which is sampled at a discrete series of points $t_k$ at equal intervals of phase $\Delta\phi=2\pi/N$ such that each cycle of $\phi(t)$ is divided evenly in N equal phase intervals called fractional-cycle intervals, and N is a constant integer.

The error attenuation is accomplished by subtracting the estimated error $E(t)$ from the known signal $S(t)$ to produce the error-corrected signal $R(t)$:

$$R(t)=S(t)-E(t). \tag{72}$$

In another embodiment of the error attenuation, the error estimation and error subtraction are accomplished efficiently in one single operation, by combining the error estimate and the subtraction into a single filter in step (rr) of the fractional-cycle-interval filter. In this embodiment, the response function of the filter in step (rr) of the fractional-cycle-interval filter will be equivalent to one minus the response function of the harmonic phase filter:

$$R(t)=S(t)-F_{\phi(t)}[S(t)]=(1-F_{\phi(t)})[S(t)]. \tag{73}$$

An advantage of combining the subtraction and the fractional-cycle-interval filter into a single operation is that rounding error is reduced by eliminating the determination of the value of the estimated error $E(t)$.

The description given in the present invention of this fractional-cycle-interval filter uses time values as the independent variable t for describing the method. However, it should be understood that the independent variable t may represent any independent variable, including but not limited to a spatial variable such as distance. The same method applies in a similar fashion to any independent variable, such as functions of a spatial variable.

It will be apparent to one skilled in the art that there are other mathematically equivalent ways to describe the fractional-cycle-interval filter.

In one embodiment, the fractional-cycle-interval filter is applied to an anharmonic driving-point motion signal. The input signal is the driving-point motion signal, and the phase reference signal P(t) comprises a representation of the reference signal of a controlled actuator which produces the driving-point motion. As already explained, the driving-point motion of an elastic material consists of anharmonic response components at harmonics of the driving force. The fractional-cycle-interval filter selectively attenuates these harmonics, so the phase-filtered signal produced in step (rr) represents a broad-band estimate of the error components of the anharmonic driving-point signal. These error components may be measurement errors and other noises not representative of the physically realizable motions of an elastic material. The estimated error is subtracted from the driving-point motion signal to produce an error-corrected driving-point motion signal. The error-corrected driving-point motion signal comprises harmonic components at harmonics of the driving force, and the amplitude and phase relationships of these harmonic components are substantially preserved by the fractional-cycle-interval filter correction. The error-corrected anharmonic driving-point motion signal is then useful for determining elastic properties of the elastic material.

In another embodiment, the fractional-cycle-interval filter is applied to an integrated motion signal, representing the integration of an anharmonic driving-point motion signal. The input signal is the integrated motion signal, and the phase reference signal P(t) comprises a representation of the actuator control reference signal. The phase-filtered signal produced in step (rr), above, represents a broad-band estimate of the integration error in the integrated motion signal. The estimated integration error is subtracted from the integrated driving-point motion signal to produce an error-corrected integrated anharmonic driving-point motion signal.

The time derivative of the estimated integration error can also used to estimate error in the signal being integrated. For example, a measured acceleration signal is integrated to produce a velocity signal. The integration error in the velocity signal is estimated using the fractional-cycle-interval filter method. The estimated integration error is subtracted from the velocity signal to produce an error-corrected velocity signal. The time derivative of the estimated integration error is determined to produce an estimate of error in the acceleration signal, and this derivative error estimate is subtracted from the acceleration signal to produce an error-corrected acceleration signal. This process can be repeated for the velocity signal, to estimate integration error in the displacement signal, which is subtracted from the displacement signal to produce an error-corrected displacement signal. The estimated displacement error can be differentiated to produce a further correction of the velocity signal, and can be double-differentiated to produce a further correction of the acceleration signal.

In another embodiment, the fractional-cycle-interval filter is applied to an anharmonic driving force signal. The input signal is the driving force signal, and the phase reference signal comprises a representation of the actuator control signal. The phase-filtered signal produced in step (rr), above, represents a broad-band estimate of the measurement error in the driving force signal. The estimated error is subtracted from the driving force signal to produce an error-corrected driving force signal. The error-corrected driving force signal is useful for determining elastic properties of the elastic material.

In another embodiment of the present invention, integration error and/or measurement error in the driving-point motion signals and in the driving force signal are estimated using a fractional-cycle interval filter, and the errors are attenuated by subtracting the estimated error from the corresponding signal. The error-corrected signals are representative of the driving-point response, and are analyzed to determining one or more elastic properties of the elastic material.

A fractional-cycle-interval filter system (FCIF) for error estimation may be described by referring to the drawings and in particular to FIG. 2. FIG. 2 shows a particular embodiment of a fractional-cycle-interval filter constructed in accordance with the present invention and designated by the reference numeral 10. The fractional-cycle-interval filter 10 is provided with a phase detector 11, a phase sampler 12, a harmonic filter 13, and a re-sampler 14.

In operation, the fractional-cycle-interval filter 10 receives an input signal S(t) to be filtered and a phase reference signal P(t). The fractional-cycle-interval filter 10 has one output signal. The output signal comprises an error signal representative of an estimated broad-band error component E(t) of the input signal S(t).

The phase reference signal P(t) is communicated to the phase detector 11 via signal path 15. The phase detector 11 detects the phase of the phase reference signal P(t) and produces an output signal at the end of each fractional-cycle-interval, based on fractional-cycle-intervals in accordance with the description of equations (59), (60), and (61) supra and the description of step (pp) of the fractional-cycle-interval method above. The phase detector 11 has a configurable parameter setting for the number N of sample intervals per cycle. The output signal of the phase detector 11 is a phase-sample timing signal representative of a series of times of fractional-cycle-intervals. The phase-sample timing signal is provided to the phase sampler 12 over signal path 16 and is also provided to the re-sampler via signal path 29.

An input signal S(t) to be filtered is input via signal path 24 to the phase sampler 12. The phase-sample timing signal received over signal path 16 triggers the phase sampler 12 to sample the input signal S(t) at the end of each fractional-cycle interval. Each sample value produced by the phase sampler 12 is output via signal path 17 to the harmonic filter 13. The series of samples output by the phase sampler 12 are representative of a phase-sampled signal sampled at fractional-cycle intervals based on the phase of the phase reference signal P(t). In effect, the phase sampler 12 converts the input signal S(t) from being a function of time to being a function of phase, based on the phase of the phase reference signal P(t).

The harmonic filter 13 filters the series of samples representative of the phase-sampled signal using a filter having one or more attenuation notches (zeros) in the filter response at selected harmonics of the phase-cycle in accordance with the description of step (rr) of the fractional-cycle-interval filter method above. The attenuation notches are selected to coincide with one or more harmonic multiples of the cycle frequency which is one cycle per N samples, where N is the number of sample intervals per cycle. Because the input signal is sampled at fractional-cycle-intervals, one embodiment of the harmonic filter 13 comprises a simple, efficient digital FIR filter with attenuation notches (zeros) that substantially coincide with harmonic multiples of the per-sample phase-cycle frequency which is substantially representative of the instantaneous frequency of the phase reference signal P(t).

The filter output of the harmonic filter 13 is a filtered, phase-sampled signal representative of the estimated error component of the input signal, the estimated error being represented as a series of phase-sampled values. The filtered, phase-sampled signal is output by the harmonic filter 13 via signal path 18. The filtered, phase-sampled signal may be used as the final output of the fractional-cycle-interval filter 10, or it may be converted from a phase-sampled signal to a time-based signal by the re-sampler 14.

The re-sampler 14 receives the filtered, phase-sampled signal from the harmonic filter 13 via signal path 18, and re-samples the filtered, phase-sampled signal at equal intervals of time determined by interpolating the non-uniform times represented by the phase-sample time signal from the phase detector 11 provided via signal path 29. However, the filter output of the harmonic filter 13 has a time lag introduced by the filter. The re-sampler receives the filtered, phase-sampled signal via signal path 18 after a substantial time lag after the corresponding sample-time signal received via signal path 29 from the phase detector 11. The filter output lags the sample-time signal by an amount of time equivalent to the harmonic filter 13 delay. Therefore, the re-sampler 14 is provided with a storage buffer means to store the intervening sample-time signals received via signal path 29. The re-sampler 14 synchronizes each received sample of the filtered, phase-sampled sample to the corresponding phase-sample timing signal in the storage buffer and re-samples the filtered, phase-sampled signal at equal intervals of time. The re-sampler 14 outputs the re-sampled signal over signal path 19 which carries the output signal of the fractional-cycle-interval filter 10. The output signal on signal path 19 comprises a filtered, time-sampled signal representative of an estimated broad-band error component E(t) of the input signal S(t).

In another embodiment of the fractional-cycle-interval filter 10, the phase reference signal P(t) is represented by a monotonic phase signal φ(t). The phase detector 11 receives the phase signal φ(t) over signal path 15 and subtracts a fractional-cycle-interval phase value $$\varphi_k = k\frac{2\pi}{N}$$

from the phase signal φ(t) to produce a phase difference (φ(t)−φ$_k$). The phase detector 11 detects the end of a fractional-cycle-interval by detecting the zero-crossing of the phase difference (φ(t)−φ$_k$), and upon detecting the zero-crossing the phase detector 11 produces a phase-sample timing signal via signal path 16 representative of the time of the end of the fractional-cycle interval. To detect the time of the next fractional-cycle-interval, the phase detector 11 increments the value of the index k, to produce a new phase value φ$_{k+1}$ and a new phase difference for detecting the next zero-crossing.

In another embodiment, the harmonic filter 13 can be adapted to either attenuate or preserve one or more selected harmonic multiples of the phase reference signal, such that the filter response function comprises a magnitude response either substantially equal to zero or substantially equal to unity at each of the selected harmonic multiples. In this embodiment, the output signal on signal path 19 comprises a phase-filtered, time-sampled signal wherein selected harmonic phase components are either preserved or attenuated.

An error attenuator constructed in accordance with the present invention is shown in FIG. 2 and designated by the reference numeral 20. The error attenuator 20 is provided with a fractional-cycle-interval filter 10, a notch filter 21, and an adder 22.

In operation, the error attenuator 20 receives via signal path 23 an input signal S(t) to be error-attenuated. The input signal S(t) on signal path 23 is communicated to the fractional-cycle-interval filter 10 via signal path 24, and also communicated to the adder 22 via signal path 25. A continuous-phase signal P(t) which serves as a basis for phase sampling is provided to the fractional-cycle-interval filter 10 over signal path 15. The fractional-cycle-interval 10 filters the input signal S(t) to produce an estimated error signal representative of the estimated error component of the input signal S(t). The estimated error signal produced by the fractional-cycle-interval filter is communicated via signal path 19 to the notch filter 21 which attenuates one or more temporal frequency components, or frequency bands, substantially representative of a transient response component of the driving-point response. The transient response component frequencies are estimated or measured in advance, to establish the filter parameters for the notch filter 21. The effect of the notch filter 21 is to attenuate the transient response component. It is useful to attenuate the transient response component because the transient may not be sufficiently attenuated by the fractional-cycle-interval filter 10, because the transient response frequency components are typically not related to the frequency of the continuous-phase signal P(t). If the transient response component comprises more than one frequency or more than one frequency band, the notch filter 21 can be designed with an attenuation reject band for each frequency component of the transient response. The notch filter 21 produces via signal path 26 an output signal which is a transient-attenuated estimated error signal representative of the estimated error component of the input signal S(t).

The notch filter 21 output signal on signal path 26 is also coupled to signal path 27. The error attenuator 20 provides the transient-attenuated estimated error signal as an output signal via signal path 27.

It should be noted that the notch filter 21 can be adapted to attenuate one or more frequency bands, one or more narrow-band notches, or combinations thereof.

The adder 22 receives via signal path 26 the negative of the transient-attenuated estimated error signal which the adder 22 adds to the input signal S(t) to produce an error-corrected signal which is output by the error attenuator via signal path 28. It should noted that the fractional-cycle-interval filter 10 and the notch filter 21 each produce a time-delayed output, so that the transient-attenuated estimated error signal received by the adder 22 via signal path 26 is delayed relative to the input signal S(t) received via signal path 25. Therefore, the adder 22 is provided with a time-delay means to delay the received input signal S(t) prior to forming the summation.

The error attenuator 20 output signal on signal path 28 comprises an error-corrected signal R(t) representative of the input signal S(t) with the estimated error E(t) attenuated, in accordance with the description of equations (71) and (72) supra.

The error attenuator 20 together with the fractional-cycle-interval filter 10 provide a means to estimate and attenuate measurement error and integration error in anharmonic driving-point response signals while substantially preserving the amplitude and phase relationships of a plurality of the anharmonic component frequencies, so that these signals become more usefully representative of the actual anharmonic driving-point response of real, nonlinear elastic material.

6. Driving-Point Analyzer System for Determining Elastic Properties

Figure 3:
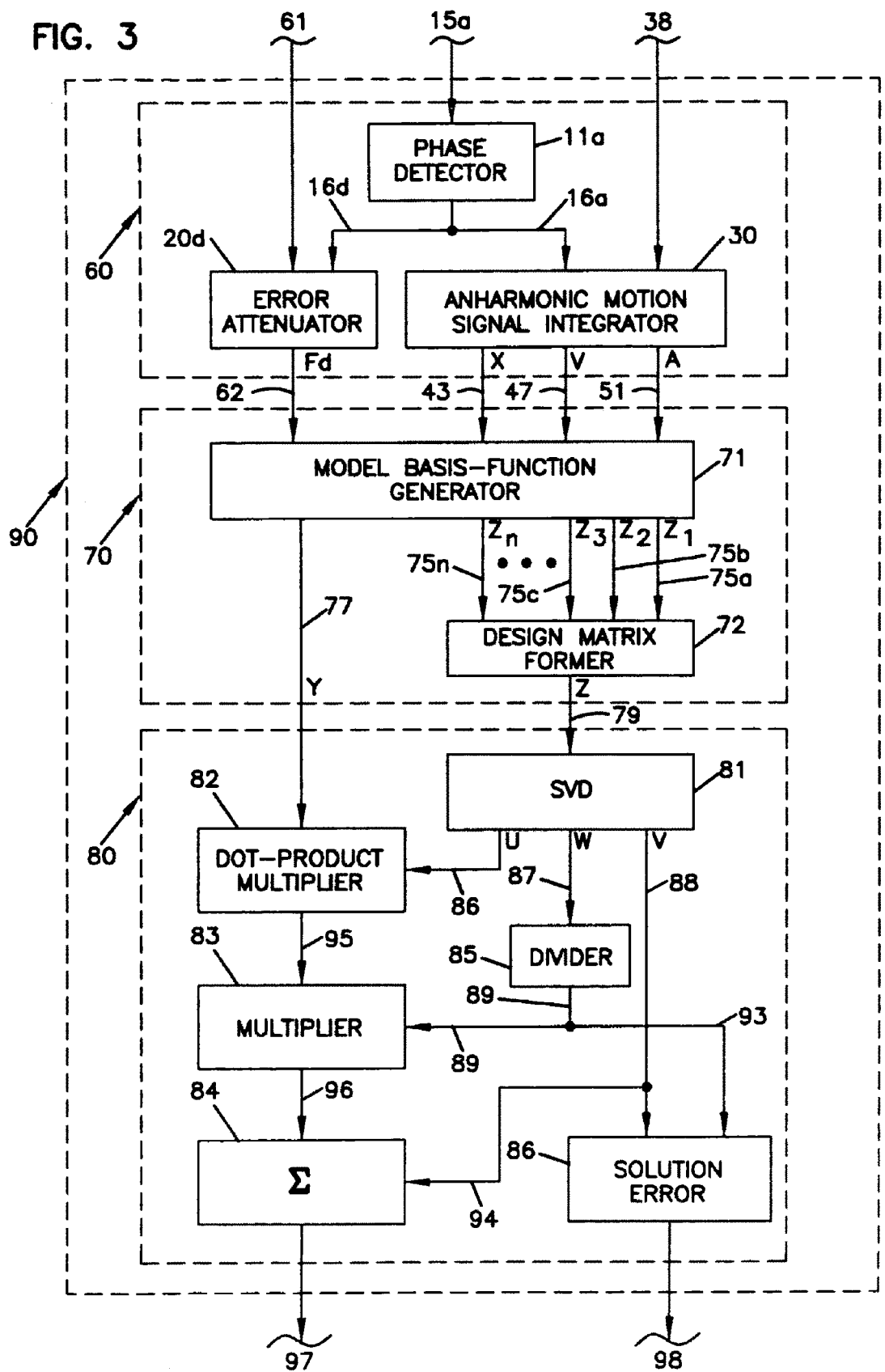
FIG. 3 is a schematic, diagrammatic view of a driving-point analyzer system 90 constructed in accordance with the present invention.

A driving-point analyzer system for determining elastic properties of an elastic material is described by referring to the drawings. FIG. 3 shows a particular embodiment of the driving-point analyzer system constructed in accordance with the present invention for determining elastic properties. The driving-point analyzer system is designated by the reference numeral 90. The driving-point analyzer 90 analyzes signals representative of a driving-point response of the elastic material. The driving-point analyzer system 90 is provided with a driving-point signal conditioner 60, a linear-system former 70, and a solver 80.

In operation, the driving-point analyzer system 90 is provided with three input signals comprising: a driving force signal via signal path 61, a driving-point motion signal via signal path 38, and a reference signal via signal path 15*a*. The driving force signal is representative of a driving force applied to the elastic material. The driving-point motion signal is representative of a driving-point motion corresponding to the driving force. The reference signal is representative of a continuous-phase reference signal used to by an actuator to control the driving-force output, such that the phase of the driving force is substantially similar to the phase of the reference signal.

In the embodiment shown, the driving-point motion signal is a driving-point acceleration signal, and the driving-point response is represented by the driving force signal and the driving-point acceleration signal.

The three input signals are received by the driving-point signal conditioner 60 where the input signals are error-corrected and the driving-point acceleration signal is integrated to produce a driving-point velocity signal and a driving-point displacement signal. The signal conditioner 60 outputs four driving-point response signals: an error-corrected acceleration signal a, an error-corrected velocity signal v, an error-corrected displacement signal x, and an error-corrected driving force signal F$_d$ via respective signal paths 51, 47, 43, and 62. The driving-point response signals are together representative of the driving-point response of the elastic material, and these four signals are communicated to the linear-system former 70.

The linear-system former 70 converts the driving-point response signals to a design matrix Z and a right-hand side vector Y which are representative of a system of linear equations representing the driving-point response of the elastic material, in accordance with a selected differential equation model as described herein above. The design matrix Z and the right-hand side matrix Y are output via respective signal paths 79 and 77 to the solver 80 which is adapted to produce a best-fit solution signal C representative of one or more elastic properties of the elastic material. The best-fit solution signal C is output via signal path 97. The solver 80 is also adapted to produce an estimated probable error signal which is output via signal path 98, and which is representative of an estimate of probable accuracies of the parameter coefficients comprising the best-fit solution C.

In the driving-point signal conditioner 60, the reference signal is communicated over signal path 15*a* to a phase detector 11*a* which functions in accordance with the phase detector 11 shown in FIG. 2 and described herein supra. The phase detector 11*a* detects the phase of the reference signal and outputs a phase-sample timing signal at a series of times of fractional-cycle-intervals. The phase-sample timing signal is communicated to an anharmonic motion signal integrator 30 via signal path 16*a* and to an error attenuator 20*d* via signal path 16*d*.

Figure 4:
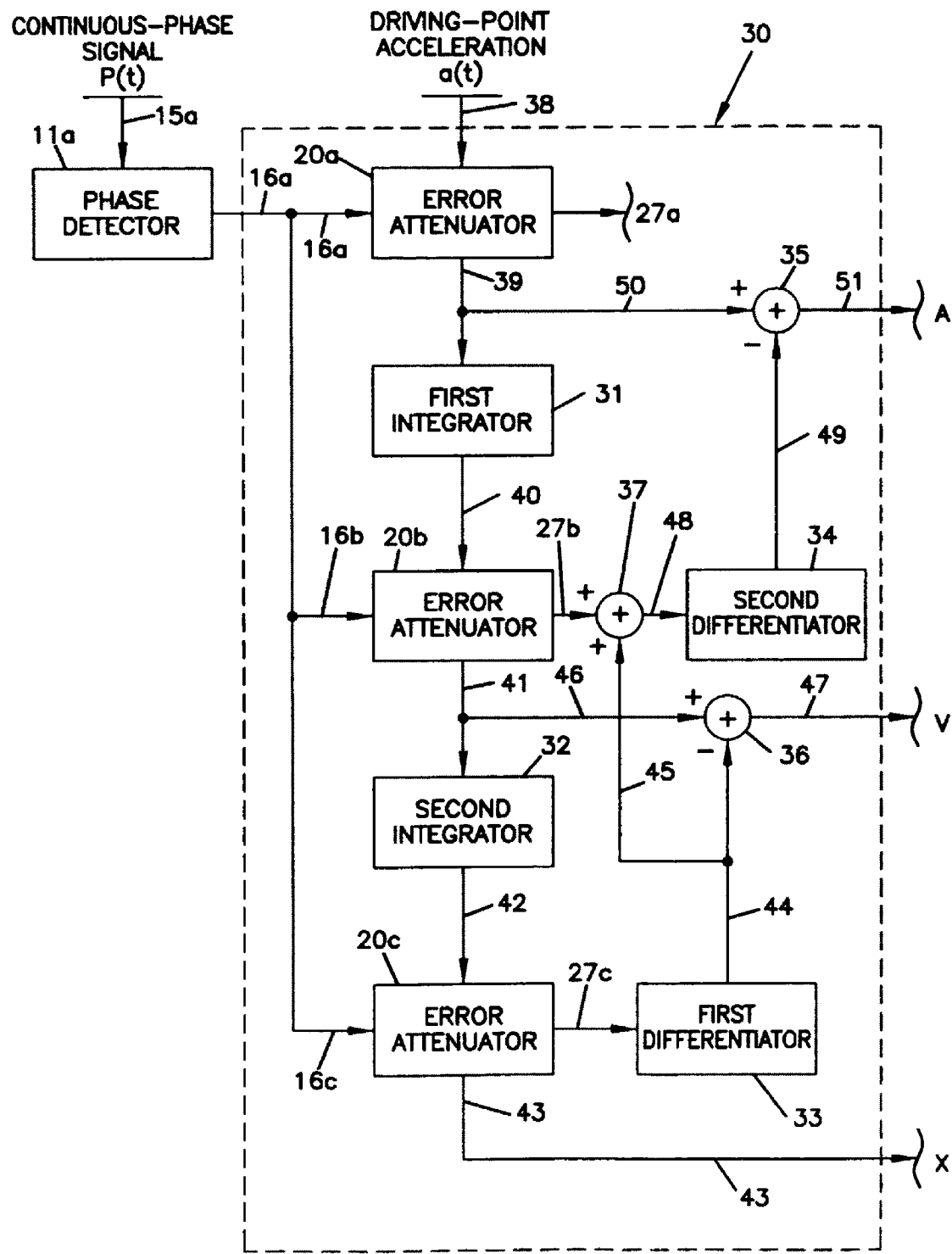
FIG. 4 is a schematic, diagrammatic view of an anharmonic motion signal integrator 30 constructed in accordance with the present invention.

The anharmonic motion signal integrator 30 also receives the input driving-point acceleration signal via signal path 38. The anharmonic motion signal integrator 30 is described by referring to FIG. 4. In summary, the anharmonic motion signal integrator 30 attenuates measurement error in the driving-point acceleration signal using a first error attenuator 20*a*, integrates the error-corrected acceleration signal once using a first integrator 31 to produce a velocity signal, and integrates the velocity signal using a second integrator 32 to produce a displacement signal. Each integrator 31, 32 is followed by an error attenuator 20 to attenuate integration error. The anharmonic motion signal integrator 30 is provided with a series of three error attenuators 20 designated by the reference numerals 20*a*, 20*b*, and 20*c* for purposes of clarity. The error attenuators 20*a*, 20*b*, and 20*c* (FIG. 4) and 20*d* (FIG. 3) are constructed and function in accordance with the error attenuator 20 shown in detail in FIG. 2 and described herein supra. However, in the embodiments shown in FIG. 3 and FIG. 4, the error attenuators 20*a*, 20*b*, and 20*c* (FIG. 4) and 20*d* (FIG. 3) all share a single, common phase detector 11*a*.

Referring again to FIG. 4, the output of the phase detector 11*a* is communicated to the error attenuators 20*a*, 20*b*, and 20*c* via signal paths 16*a*, 16*b*, and 16*c* respectively. The input driving-point acceleration signal is received via signal path 38 by the first error attenuator 20*a* which estimates and attenuates measurement error in the driving-point acceleration signal to produce an error-corrected driving-point acceleration signal. The first error attenuator 20*a* outputs the error-corrected driving-point acceleration signal via signal path 39 to a first integrator 31. The first integrator 31 integrates the error-corrected driving-point acceleration signal to produce a velocity signal which is output via signal path 40 to the second error attenuator 20*b*. As a result of the integration, the velocity signal contains integration error which must be removed before the velocity signal is useful for determining elastic properties. The second error attenuator 20*b* estimates and attenuates the integration error in the velocity signal and outputs an error-corrected velocity signal via signal path 41. The second error attenuator 20*b* also outputs a velocity error signal via signal path 27*b* representative of the estimated error component of the velocity signal.

The second integrator 32 receives the error-corrected velocity signal via signal path 41 and integrates the error-corrected velocity signal to produce a displacement signal which is output via signal path 42 to the third error attenuator 20*c*. The third error attenuator 20*c* estimates and attenuates the integration error in the displacement signal and outputs a final error-corrected driving-point displacement signal via signal path 43.

The third error attenuator 20*c* also outputs a displacement error signal via signal path 27*c* representative of the estimated error component of the displacement signal. The displacement error signal on signal path 27*c* is received by a first differentiator 33 which produces the time derivative of the displacement error signal, and outputs the time derivative as a derivative velocity error signal via signal path 44. The derivative velocity error signal represents an estimate of residual velocity error that was not attenuated by the second error attenuator 20*b*. A first adder 36 receives the negative of the derivative velocity error signal on signal path 44 and adds it to the error-corrected velocity signal on signal path 46 to produce a final error-corrected driving-point velocity signal output via signal path 47.

The derivative velocity error signal via signal path 45 is also added to the velocity error signal on signal path 27*b* by a second adder 37 to produce a combined velocity error signal output via signal path 48 to a second differentiator 34. The second differentiator 34 produces the time derivative of the combined velocity error signal, and outputs the time derivative as a derivative acceleration error signal via signal path 49. The derivative acceleration error signal represents an estimate of residual acceleration error that was not attenuated by the first error attenuator 20*a*.

A third adder 35 receives the negative of the derivative acceleration error signal via signal path 49 and adds it to the error-corrected driving-point acceleration signal from signal path 50 to produce a final error-corrected driving-point acceleration signal output via signal path 51.

It should be noted that the error attenuators 20*a*, 20*b*, and 20*c* each introduce a constant time delay between the input signal and the corresponding error-corrected output signal due to filter delays in the operation of the error attenuator 20. Therefore, the second error attenuator 20*b* and the third error attenuator 20*c* are provided with an input buffer for the respective input of the fractional-cycle-interval sample time signal 16*b* and 16*c* to compensate for the prior filter delays. The adders 36, 37, and 35 are also each provided with an input buffer means to keep their input signals synchronized.

It is noted that the first integrator 31 and the second integrator 32 are reset to zero upon initiation of the input of the start of the driving-point acceleration signal, which also represents the start of the exertion of the driving force by the actuator. Resetting the integrators 31 and 32 to zero represents an assumption of initial conditions that the elastic material is initially at rest and that the driving-point acceleration, the driving-point velocity, the driving-point displacement, and the driving force are all substantially zero-valued at the start of the input of the driving-point acceleration signal on signal path 38.

In another embodiment, either the first differentiator 33, or the second differentiator 34, or both the first differentiator 33 and the second differentiator 34 are optionally disabled such that each disabled differentiator produces a substantially zero-valued output signal on respective signal paths 44 and/or 49. This embodiment adapts the anharmonic motion signal integrator 30 to be configurable to operate without the derivative error corrections.

In another embodiment, the fractional-cycle-interval filter 10 in any one or more of the error attenuators 20*a*, 20*b*, 20*c*, or 20*d* can be replaced by a high-cut filter, wherein the high-cut corner frequency is below the fundamental frequency of the driving-force. In yet another embodiment, the error attenuator 20 can be replaced by a DC offset filter or a low-cut filter, wherein the low-cut corner frequency is below the fundamental frequency of the driving force. These two embodiments are useful for analyzing a driving-point response produced by an actuator without a reference signal, such as an impulse actuator.

In summary, the anharmonic motion signal integrator 30 integrates the input acceleration signal, and attenuates measurement error and integration error while substantially preserving the amplitude and phase relationships of the anharmonic signal components at harmonics of the continuous-phase reference signal, so that the output signals are representative of the anharmonic driving-point response of nonlinear elastic material. The net result of the operation of the anharmonic motion signal integrator 30 is to produce three output signals: a final error-corrected driving-point acceleration signal via signal path 51, a final error-corrected driving-point velocity signal via signal path 47, and a final error-corrected driving-point displacement signal via signal path 43.

Referring now to FIG. 3 and to the driving-point signal conditioner 60, the driving-force signal is communicated over signal path 61 to a fourth error attenuator 20d, which estimates and attenuates measurement error in the driving-point force signal, to produce an error-corrected driving-point force signal which is output via signal path 62.

In summary, the driving-point signal conditioner 60 receives the driving-point acceleration signal (signal path 38), the driving force signal (signal path 61), and the reference signal (signal path 15a), and outputs four final error-corrected driving-point response signals: the final error-corrected driving-point acceleration signal (signal path 51), the final error-corrected driving-point velocity signal (signal path 47), the final error-corrected driving-point displacement signal (signal path 43), and the error-corrected driving force signal (signal path 62). The driving-point signal conditioner 60 substantially preserves the amplitude and phase relationships of a plurality of harmonic frequency components of the driving-point response signals representative of the anharmonic response of non-linear elastic material.

The operation of the linear system former 70 is in accordance with the description of step (aa) supra. The solver 80 operates in accordance with the description of step (bb) supra, and in particular the embodiment shown in FIG. 3 operates in accordance with the description of steps (cc) through (ff) supra.

The final error-corrected driving-point response signals are received by the linear system former 70 where they are communicated to a model basis-function generator 71. The model basis-function generator 71 generates a set of signals representative of a system of linear equations based on a differential equation model of the response of the elastic material. The set of signals comprises a right-hand side signal Y and a set of model basis-function signals $Z_j$. Each model basis function signal $Z_j$ is representative of a corresponding model basis-function $Z_j(t)$ in accordance with equation (32) supra and the description of step (aa) supra. The right-hand side signal Y is representative of a corresponding right-hand side function y(t) in accordance with equation (32) supra and the description of step (aa) supra. In operation, the model basis-function generator 71 is configured by selecting a particular differential equation model. The model basis-function generator 71 is adapted to generate the right-hand side signal Y and the model basis-function signals $Z_j$ in accordance with the particular differential equation model that is selected. The model basis-function generator 71 uses the driving-point response signals received on signal paths 51, 47, 43, and 62 to generate the right-hand side signal Y and the model basis-function signals $Z_j$ in accordance with equation (32) and the description thereof supra. Each model basis-function signal $Z_j$ generated by the model basis-function generator 71 is a signal which comprises a function of one or more of the driving-point response signals.

As an example for purposes of clarity, in one embodiment the model basis-function generator 71 is configured with a selected differential equation model represented by equation (18) supra. Operating with the selected differential equation model represented by equation (18) supra including terms to the fifth power of velocity and to the third power of displacement, the model basis-function generator 71 generates the following set of eight distinct signals:

$Z_j$: a, v, $v^3$, $v^5$, x, $x^2$, $x^3$ and $Y=F_d$, where a set of seven distinct model basis-function signals $Z_j$ are as follows:

$Z_1$: a represents the final error-corrected driving-point acceleration signal;

$Z_2$: v represents the final error-corrected driving-point velocity signal;

$Z_3$: $v^3$ represents the third power of the final error-corrected driving-point velocity signal;

$Z_4$: $v^5$ represents the fifth power of the final error-corrected driving-point velocity signal;

$Z_5$: x represents the final error-corrected driving-point displacement signal;

$Z_6$: $x^2$ represents the second power of the final error-corrected driving-point displacement signal;

$Z_7$: $x^3$ represents the third power of the final error-corrected driving-point displacement signal;

and the right-hand side signal Y is

Y: $F_d$ represents the error-corrected driving force signal.

The model basis-function generator 71 outputs each model basis-function signal $Z_j$ over a corresponding signal path 75 which are indicated in FIG. 3 for purposes of clarity by the reference numerals 75a, 75b, 75c, . . . , $75_N$. For each model basis-function signal $Z_j$ there is a corresponding signal path 75. The number N of model basis-function signals generated by the model basis-function generator corresponds to the number N of unknown parameter coefficients in the selected differential equation model. In one embodiment, the model-basis function generator 71 is adapted to operate with a maximum number of distinct signal paths 75 that does not substantially exceed thirty-two signal paths 75 and does not substantially exceed thirty-two distinct model basis-function signals $Z_j$. Other embodiments may have substantially more than 32 basis-function signal paths as needed for the desired differential equation model.

The model basis-function generator 71 outputs the right-hand side signal Y over signal path 77.

The model basis-function generator 71 is provided with a storage means to store the driving-point response signals which are received from the driving-point signal conditioner 60. The model basis-function generator 71 may be operated to repeatedly use the stored driving-point response signals to form a series of different systems of linear equations wherein each system of linear equations is based on a different differential equation model for the same driving-point response signals. The series of systems of linear equations are solved by the solver 80 to determine a series of different best-fit solutions each representative of a different differential equation model. The different best-fit solutions may be combined to determine a combined solution based on two or more different differential equation models.

The particular embodiment of the model basis-function generator 71 shown in FIG. 3 is provided with four input signals. Depending on the differential equation model, one or more of the input signals may not be required to form the set of basis-function signals and the right-hand side signal. The driving-point response signals which are not used to form a basis-function signal are not needed, and the unused signal inputs are optional.

The present invention encompasses a model basis-function generator 71 adapted and operated with fewer than four input signals or more than the four input signals shown. To practice the present invention, the minimum input needed to operate the linear system former 70 and the model basis-function generator 71 is a driving force signal and any two of the corresponding driving-point motion signals. To practice a particular embodiment of the present invention, the actual input needed comprises the signals needed to form the set of basis functions corresponding to the desired differential equation model. The present invention encompasses use of a differential equation model and a corresponding set of basis functions which can be functions of any combination of a driving-point motion in any of six component directions of normal, shear, and/or rotation; a driving force in any of six component directions of normal, shear, and/or rotation; and/or signals representative of actuator element motions such as reaction-mass motion, relative baseplate-to-reaction-mass motion, hold-down mechanism motions, and/or hydraulic pressure signals.

The present invention encompasses basis functions which are equivalent to one of the input driving-point motion signals, such that generating a basis function signal comprises simply passing the input signal through to the design matrix former 72. In the case where generating a basis function signal comprises passing the input signal through to the design matrix former 72, the signal so produced is nevertheless considered to comprise a basis function signal generated by a model-basis function generator 71.

The design matrix former 72 receives the model basis-function signals $Z_j$ via respective signal paths 75, and forms a matrix Z representative of a design matrix in accordance with equations (41) and (37) supra and the description of step (aa) supra. For each distinct model basis-function signal $Z_j$ there is a corresponding distinct column of the design matrix Z. There are the same number N of columns in the design matrix Z as the number N of model basis-function signals $Z_j$ produced by the model basis-function generator 71. Each row of the design matrix comprises the values representative of each of the model basis-function signals $Z_j$ at a distinct time $t_i$; the N values at each distinct time $t_i$ thereby comprise the elements $z_{ij}$ of a matrix row. The distinct time $t_i$ represents a time relative to the initiation of the driving force. There is a distinct time $t_i$ corresponding to each row of the design matrix. There is a distinct model basis-function signal $Z_j$ corresponding to each column of the design matrix.

The design matrix former 72 is provided with a configurable matrix design criterion which represents a set of distinct times $t_i$ to form the rows of the design matrix Z. The design matrix former 72 samples the model basis-function signals $Z_j$ at the set of distinct times $t_i$ to fill the rows of the design matrix Z.

The distinct set of times can be any one or more of the following: a set of times comprising a continuous sequence of times, a set of times comprising a discontinuous sequence of times, a set of times not in time-order, a set of times at uniform intervals, a set of times at non-uniform intervals, or any combinations thereof.

In one embodiment, the matrix design criterion comprises a defined time interval and a defined number of rows comprising the design matrix Z. The design matrix former 72 evaluates the basis-function signals at the defined time intervals and fills rows of the design matrix Z by storing the values the matrix elements $z_{ij}$ until the criterion for the defined number of rows is reached, whereupon the design matrix Z is output via signal path 79.

In another embodiment, the matrix design criterion comprises a defined time window for a time period within the time period of the model basis-function signals $Z_j$. The design matrix former 72 fills rows of the design matrix Z by storing the values the matrix elements $z_{ij}$ beginning with a time $t_0$ at the start of the time window criterion and continuing until the criterion for end of the time window is reached, whereupon the design matrix Z is output via signal path 79.

In another time window embodiment, the matrix design criterion comprises a defined sequence of time windows. The design matrix former 72 forms the design matrix Z for each particular time window in the sequence, removing the matrix elements $z_{ij}$ that have expired from the particular time window and adding the matrix elements $z_{ij}$ until the criterion for end of the particular time window is reached. A distinct design matrix Z is output for each distinct time window in the defined sequence of time windows, thereby producing a sequence of design matrices Z corresponding to the sequence of time windows determined by the matrix design criterion. The defined sequence of time windows may be overlapping time windows or non-overlapping time windows. The design matrix former 72 operating with a design matrix criterion representing a sequence of time windows provides a means for determining the value of one or more elastic properties as a function of time, by analyzing each design matrix so produced to determine a value of one or more elastic properties for each time window.

In another embodiment, the matrix design criterion comprises a direction of stroke of the driving force. The design matrix former 72 fills rows of the design matrix Z by storing the values the matrix elements $z_{ij}$ corresponding to times $t_i$ when the direction of stroke, as determined by the sign of the driving-point velocity for example, is in the direction defined by the matrix design criterion. The design matrix former 72 operating with a direction-of-stroke matrix design criterion provides a means for determining values of one or more elastic properties as a function of the direction of stroke of the driving force exerted by the actuator.

The example embodiments of the matrix design criterion may also be used in combinations. For example, another embodiment of the matrix design criterion comprises a defined time interval, a defined direction of stroke, a defined number of matrix rows, and a defined sequence of time windows.

It will be apparent to one skilled in the art that there are other embodiments of time criteria and other combinations of time criteria which may be used to form the design matrix.

The design matrix former 72 is adapted for amplitude control of the basis-function signals. The design matrix former 72 applies a desired scale factor to each of the basis-function signals in the design matrix. The scale factors provide a means to independently control the amplitude of each basis-function signal in the design matrix. Adjusting the amplitude of the basis-function signals in the design matrix provides a means to control the conditioning of the design matrix, and to control the quality of the solution of the system of linear equations.

Each element of the design matrix comprises a scaled value representative of the value of the corresponding basis-function signal multiplied by the desired scale factor. There is a distinct scale factor corresponding to each basis-function signal. Each of the distinct scale factors is constant within a single design matrix.

In one embodiment, the scale factors are chosen such that the scaled basis-function signals all have approximately the same a.c. amplitude level. This is useful because the amplitude scales of the basis-function signals may otherwise differ by several orders of magnitude. Using basis function signals with widely different amplitudes produces an ill-conditioned design matrix, and results in a solution for the parameter coefficients which may be dominated by rounding error and other numerical noises. Using basis functions scaled to approximately the same amplitude level improves the conditioning of the design matrix, and improves the quality of the solution.

In another embodiment, the scale factors can be chosen based on characteristics other than a.c. amplitude, such as probable error of each signal, to provide a means to control other characteristics of the solution.

If the design matrix former 72 produces a series of design matrices for a series of time windows, the amplitude control scale factors can be different for each design matrix in the series. The relative amplitudes of the basis-function signals can change with time, so it is useful to adjust the scale factors for each design matrix. The scale factors are constant within each design matrix, but each scale factor is adjusted for each new design matrix, thereby providing amplitude control for the basis-function signals.

In one embodiment, the amplitude control scale factors can be defined as a configuration setting of the design matrix former 72. In another embodiment, the design matrix former 72 can be adapted to determine a set of scale factors based on the relative amplitudes of one or more basis-function signals within the time period spanned by the set of distinct times used to form the design matrix.

The amplitude control scale factors used by the design matrix former 72 are known values, which can be used to re-scale the solution results output by the solver 80 to a desired scale.

Amplitude control of the basis-function signals can be disabled by specifying unity scale factors for all basis-function signals.

The design matrix former 72 is provided with a storage means to store the values of the elements $z_{ij}$ comprising the design matrix Z while the design matrix Z is being formed. The design matrix former 72 outputs the design matrix Z to the solver 80.

The solver 80 receives the design matrix Z via signal path 79 and the right-hand side signal Y via signal path 77. The solver 80 analyzes the design matrix Z and the right-hand side signal Y to determine a best-fit solution C comprising a best-fit linear combination of the columns of the design matrix Z that fits the right-hand side signal Y. The solver 80 may use any of various known methods for solving a system of linear equations, in accordance with the description of step (bb) herein supra.

In the embodiment shown in FIG. 3, the solution is by a singular value decomposition method, in accordance with steps (bb) and (cc) through (ff) and the description thereof supra.

Referring to FIG. 3, the solver 80 is provided with a singular value decomposition (SVD) block 81. The SVD block 81 receives the design matrix Z via signal path 79 and factors the design matrix Z in accordance with equation (47) and the description thereof supra to produce a singular value decomposition comprising a left-side matrix U (output via signal path 86), a singular value matrix W (output via signal path 87), and a basis matrix V (output via signal path 88).

The singular value matrix W is received via signal path 87 by a divider 85. The divider 85 is provided with a minimum threshold $\epsilon$ which is a configurable parameter value representative of the threshold for rejecting singular values in accordance with equation (51) and the description thereof supra. For each singular value element $w_k$ of the singular value matrix W, the divider 85 produces a reciprocal singular value representative the reciprocal of the singular value element ($1/w_k$) if the value of the singular value element $w_k$ is greater-than or equal-to the minimum threshold $\epsilon$; or produces a zero-value output if the value of the singular value element $w_k$ is less than the minimum threshold $\epsilon$. The divider outputs the values so produced via signal path 89 and also provided by connection to signal path 93.

The left-side matrix U is received by a dot-product multiplier 82. The dot-product multiplier 82 is configured with a time selection criterion representing the same set of distinct times $t_i$ that were used by the design matrix former 72 to produce the design matrix Z. The dot-product multiplier 82 produces the dot-product multiplication of each column of the left-side matrix U with the right-hand side signal Y received from signal path 77 in accordance with step (ee) and the description thereof supra. The correspondence of the right-hand side signal Y with the columns of the left-side matrix U is determined by the same set of distinct times $t_i$ used for forming the design matrix Z. The dot-product multiplier 82 uses the values of the right-hand side signal Y at the set of distinct times $t_i$ to form a dot-product with each column of the left-side matrix U. The dot-product output comprises one dot-product value for each column of the N columns of the left-side matrix U. The set of N dot-product values are output via signal path 95 to a multiplier 83.

The multiplier 83 multiplies each of the N dot-product values received via signal path 95 by the corresponding reciprocal singular values received via signal path 89. The result of the multiplication is a set of N weighted dot-product values $d_k$ which are weighted by the corresponding reciprocal singular values ($1/w_k$). The weighted dot-product values $d_k$ are output from the multiplier via signal path 96.

The net effect of the operation of the dot-product multiplier 82, the divider 85, and the multiplier 83 is to produce a set of N values $d_k$ in accordance with equation (51) and the description thereof supra and in accordance with steps (dd) and (ee) and the description thereof supra. The configurable minimum threshold $\epsilon$ in the divider 85 provides control over the nullspace solution in accordance with step (dd) and the description thereof supra.

The basis matrix V is communicated from signal path 88 coupled through signal path 94 to a weighted summing block 84, which also receives the weighted dot-product values $d_k$ via signal path 96. The weighted summing block 84 operates in accordance with step (ff) and the description thereof supra. The weighted summing block 88 forms the weighted sum of the column vectors of the basis matrix V using as weights the corresponding weighted dot-product values $d_k$, the summation thereby producing a solution vector C comprising elements $c_j$ in accordance with equation (50) and the description thereof supra. The elements $c_j$ of the solution vector C are output from the weighted summing block 84 via signal path 97.

The solution vector C output via signal path 97 represents a best-fit solution of the system of linear equations formed by the linear system former 70.

An estimate of the relative probable error of the elements $c_j$ of the solution vector C is produced by a solution error block 86. The solution error block 86 has two inputs and one output. The two inputs are the basis matrix V received via signal path 88 and the reciprocal singular values ($1/w_k$) received via signal path 93 which is coupled to the signal path 89 output of the divider 85. The solution error block 86 produces an output representative of an estimate of the relative probable error the solution C from the basis matrix V and the reciprocal singular values ($1/w_k$) in accordance with equation (53) and the description thereof supra. The estimated relative probable error is output by the solution error block via signal path 98.

The elements of the solution vector C output on signal path 97, and the estimated relative probable error on signal path 98, represent an output of the solver 80 and comprise an output of the driving-point analyzer system 90.

The values of the elements $c_j$ of the solution vector C output on signal path 97 comprise a best-fit solution of the system of linear equations formed by the linear system former 70. The values of the elements $c_j$ comprising the solution vector C are representative of a best-fit solution for the values of the parameter coefficients of the particular differential equation model that is selected in the configuration of the model basis-function generator 71, and for the particular time selection represented by the matrix design criterion configuration of the design matrix former 72.

The values of the parameter coefficients which are output by the solver 80 can be re-scaled to a desired output scale based on the known values of the several scale factors used within the system. The scale of the parameter coefficient values are affected by the following scale factors: the scale of the driving-point acceleration signal used as initial input to the driving-point analyzer system 90 on signal path 38; the scale of the driving-force signal used as initial input to the driving-point analyzer 90 on signal path 61; the set of scale factors applied to the basis-function signals by the design matrix former 72; scale factors representative of the amplitude scale used to represent each of the various signals in the driving-point analyzer system 90; and other scale factors which may have been applied by the model basis-function generator 71, the anharmonic motion signal integrator 30, the error-attenuator 20d, or the solver 80.

The best-fit set of parameter coefficients are representative of one or more elastic properties of the elastic material. The meaning of each parameter coefficient is based on the meaning of the corresponding term of the selected differential equation model selected in the configuration of the model basis-function generator 71. The best-fit solution values of the parameter coefficients are representative of the best-fit solution for a particular matrix design criterion, wherein the matrix design criterion comprises the set of distinct times used by the design matrix former 72.

To operate the driving-point analyzer system 90, the model basis-function generator 71 is configured with a desired differential equation model representing the driving-point response of the elastic material. The design matrix former 72 is configured with a desired matrix design criterion for a set of distinct times to analyze, and a desired set of scale factors for amplitude control of the basis-function signals. The fractional-cycle-interval filters 10 in each of the error-attenuators 20a, 20b, 20c, 20d, are configured with a desired harmonic filter response. The phase detector 11a is configured with a desired number of phase-intervals-per cycle to use for generating the phase-timing signal.

The input signals representative of the driving-point response of an elastic material are input to the driving-point signal conditioner 60: the driving-point acceleration signal via signal path 38, the driving force signal vial signal path 61, and the corresponding reference signal via signal path 15a. The driving-point signal conditioner 60 integrates the acceleration and attenuates integration error and measurement error in the driving-point response signals to produce a set of error-corrected driving-point response signals that are useful for determining elastic properties of the elastic material. The linear system former 70 forms the error-corrected driving-point response signals into a system of linear equations in accordance with the selected differential equation model and for the set of distinct times, to produce a design matrix Z and a right-hand side matrix Y output via respective signal paths 79 and 77 to the solver 80. The solver 80 is adapted to produce a best-fit solution of the system of linear equations by means of singular value decomposition of the design matrix Z. The solver 80 outputs the best-fit solution C via signal path 97 along with an estimated relative probable error of the solution on signal path 98.

7. Estimated Force Output of a Reciprocating Actuator Using an Error-attenuator

The present invention provides systems and methods to estimate and attenuate errors in the measured force output of a reciprocating actuator, such as a seismic vibrator. The error-attenuator 20 and fractional-cycle-interval filter 10 are useful for attenuating errors in an actuator force output.

It is well known in the art that the force output of a reciprocating actuator can be estimated as the mass-weighted sum of the baseplate acceleration and the reaction-mass acceleration (J. Sallas, 1984, "Seismic vibrator control and the downgoing P-wave": Geophysics, v. 49, no. 6, pp. 732-740):

$$F_d = (M_b a_b + M_r a_r), \qquad (74)$$

where $F_d$ is the driving force exerted by the actuator on the substrate material; $M_b$ is the inertial mass of the baseplate; $a_b$ is the acceleration motion of the baseplate; $M_r$ is the inertial mass of the reaction-mass; and $a_r$ is the acceleration motion of the reaction mass.

In one embodiment, each of the acceleration signals $a_b$ and $a_r$ is error-corrected by an error attenuator 20 (FIG. 2) prior to forming the weighted sum.

The baseplate acceleration and the reaction-mass acceleration are measured motion signals, typically measured by acceleration sensors. Referring to FIG. 2, an actuator reference signal corresponding to the two acceleration signals is provided to the error attenuator 20 via signal path 15 to serve as the phase reference signal. Each of the two acceleration signals is input to a distinct error attenuator 20 via a distinct signal path 23, to produce an error-corrected baseplate acceleration signal and an error-corrected reaction-mass acceleration signal. The mass-weighted sum of the error-corrected baseplate acceleration and the error-corrected reaction-mass acceleration comprises an estimated actuator output force signal wherein the anharmonic signal components are preserved and other components are attenuated.

In another embodiment, each of the two acceleration signals—the baseplate acceleration signal and the reaction-mass acceleration signal—is error-corrected by an anharmonic motion signal integrator 30 (FIG. 4) prior to forming the weighted sum. The anharmonic motion signal integrator 30 operates as already described herein. The anharmonic motion signal integrator 30 outputs a final error-corrected acceleration signal via signal path 51 which is then used to form an error-corrected weighted sum force signal.

Figure 7:
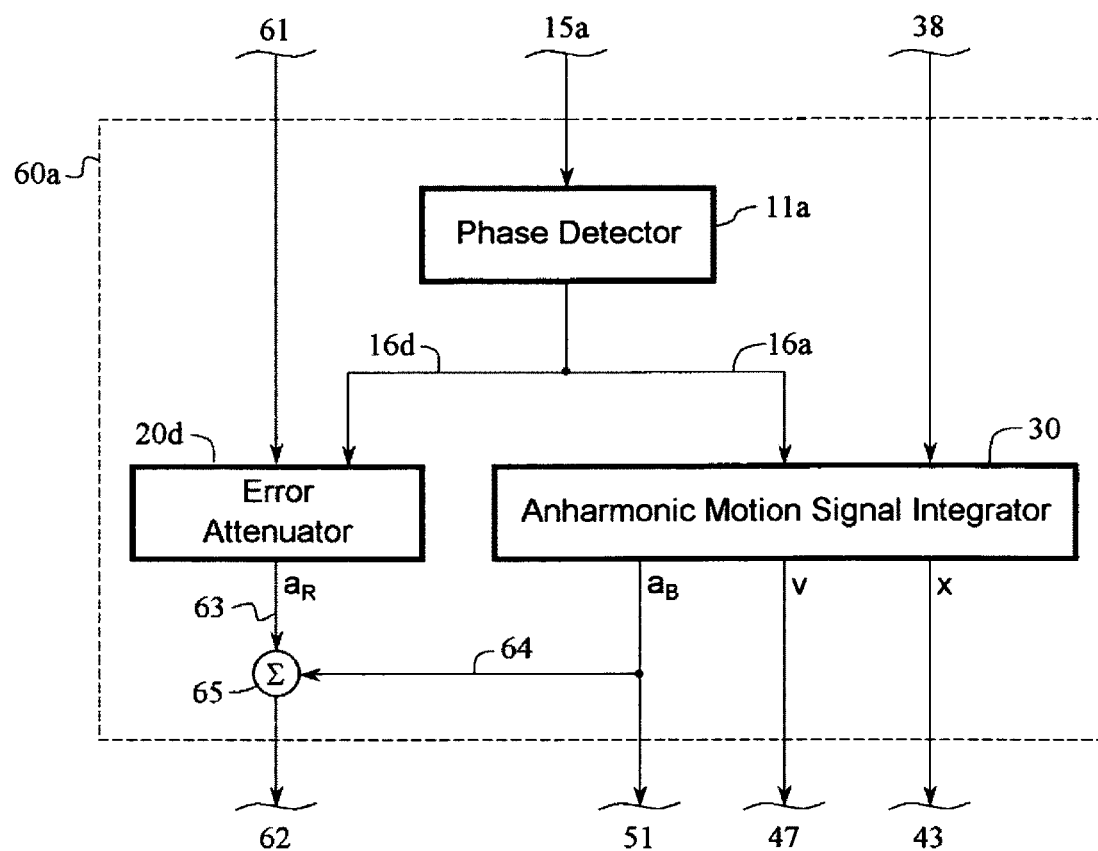
FIG. 7 is a schematic, diagrammatic view of a particular embodiment of a driving-point signal conditioner 60a constructed in accordance with the present invention.

FIG. 7 depicts yet another embodiment of a system to produce an error-corrected driving-force signal, included in a driving-point signal conditioner 60a. The driving-point signal conditioner 60a produces an output signal on signal path 62 representative of an error-corrected driving force signal. The driving-point signal conditioner 60a receives a baseplate acceleration signal via signal path 38, a phase reference signal via signal path 15a, and a reaction-mass acceleration signal via signal path 61. The anharmonic motion signal integrator 30 receives the baseplate acceleration signal via signal path 61, and estimates and attenuates error in the baseplate acceleration signal to produce an error-corrected driving-point acceleration signal on signal path 51. The error attenuator 20d receives the baseplate acceleration on signal path 61, and estimates and attenuates error to produce an error corrected baseplate acceleration signal on signal path 63. A weighted summing component 65 receives the error corrected driving-point acceleration signal via signal path 64 and the error-corrected baseplate acceleration signal via signal path 63. The weighted summing component 65 forms a weighted sum of the two acceleration signals to produce an error-corrected driving force signal output on signal path 62. Further description of the operation of the driving-point signal conditioner 60a is provided in Example 1.

In another embodiment, a weighted sum force signal is formed prior to error correction, and then the weighted sum force signal is error-corrected using an error attenuator 20 to form an error-corrected driving force signal. This embodiment is included in the particular driving-point analyzer system 90 shown in FIG. 3. Referring to FIG. 3, the driving-force signal is input to the error attenuator 20d via signal path 61. A phase reference signal representative of the actuator reference signal is provided to the phase detector 11a via signal path 15a. The output of the error attenuator 20 via signal path 62 is representative of an error-corrected actuator force output signal.

The error-corrected driving-force signal produced by these embodiments is more accurately representative of the anharmonic response of a real, nonlinear elastic material, and is thereby useful for determining elastic properties of the material.

8. An Improved Estimate of a Reciprocating Actuator Output Using a Relative Displacement Measurement Reciprocating actuators often have a measurement sensor that measures the position of the reaction-mass relative to the position of the baseplate. For example, some reciprocating actuators such as seismic vibrators have a displacement transducer, such as a Linear Variable Displacement Transducer (LVDT), coupled to the reaction-mass and the baseplate such that output of the displacement transducer is representative of the displacement of the reaction mass relative to the baseplate. The relative displacement signal can be used in combination with the two acceleration signals (baseplate acceleration, reaction-mass acceleration) to produce an improved estimate of the driving-point motion of the actuator baseplate, and also to produce an improved estimate of the driving force output of the reciprocating actuator.

In one embodiment of a reciprocating actuator, three distinct signals are measured which are representative of the motion of the actuator: a baseplate acceleration signal, a reaction-mass acceleration signal, and a relative displacement signal. The relative displacement signal is measured by a displacement transducer which produces a signal representative of the displacement of the reaction-mass relative to the baseplate. The baseplate acceleration signal is measured by an acceleration sensor coupled to the baseplate such that the acceleration sensor produces an output signal representative of the acceleration motion of the baseplate. The reaction-mass acceleration signal is measured by an acceleration sensor coupled to the reaction-mass such that the acceleration sensor produces an output signal representative of the acceleration motion of the reaction-mass.

The present invention discloses a system and two methods for combining these three signals.

One method is to use the second time-derivative of the relative displacement signal to produce a relative acceleration signal which is combined with the baseplate acceleration signal and the reaction-mass acceleration signal. The actuator force output is estimated as a weighted sum of the baseplate acceleration, the reaction-acceleration, and the relative acceleration. The baseplate acceleration and the reaction-mass acceleration are weighted by a factor proportionally representative of the sum of the baseplate mass and the reaction-mass mass. The relative acceleration is weighted by a factor proportionally representative of the difference between the reaction-mass mass and the baseplate mass.

Applying algebraic rearrangement to equation (74) supra for the weighted-sum force output of a reciprocating actuator results in the following expression representative of an estimated force output of a reciprocating actuator:

$$-F_{d+} = \sigma \times \left(\frac{M_r + M_b}{2}\right) + \delta'' \times \left(\frac{M_r - M_b}{2}\right), \tag{75}$$

where × denotes multiplication, and
$F_{d+}$ represents a combined estimate of the force exerted by the actuator baseplate on the substrate material at the contact surface area;
$M_r$ is the inertial mass of the reaction-mass;
$M_b$ is the inertial mass of the baseplate;
$\sigma = a_r + a_b$, which is the sum of the reaction-mass acceleration $a_r$ and the baseplate acceleration $a_b$;
$\delta = x_r - x_b$, which is the relative displacement of the reaction-mass position $x_r$ relative to the baseplate position $x_b$, as measured by a displacement transducer; and $$\delta'' = \frac{d^2\delta}{dt^2},$$

which represents the second derivative of the relative displacement $\delta$ with respect to time, so is therefore representative of the relative acceleration of the reaction-mass relative to the baseplate: $\delta'' = a_r - a_b$.

In other words, the force exerted on the substrate material by a reciprocating actuator is estimated as the sum of two quantities: (a) the first quantity is the average of the masses of the reaction-mass and the baseplate, the average multiplied by the sum of the reaction-mass acceleration and the baseplate acceleration; and (b) the second quantity is the second derivative of the relative displacement multiplied by one-half the difference in the masses of the reaction-mass and the baseplate. It is understood that the accelerations, the relative displacement, and the force are all functions of time. It is also understood that the accelerations and the relative displacement are measured relative to the same defined direction, such that positive acceleration and positive displacement are both in the same direction, and negative acceleration and negative displacement are in the opposite direction.

Dividing equation (75) by the average mass of the reaction-mass and the baseplate produces another embodiment of the combined estimate of actuator force output:

$$-\left(\frac{2}{M_r + M_b}\right) \times F_{d+} = a_r + a_b + \delta'' \times \left(\frac{M_r - M_b}{M_r + M_b}\right), \tag{76}$$

where the left-hand side of equation (76) represents the driving force scaled by a constant factor representing the reciprocal of the average mass of the baseplate and the reaction-mass, and the right-hand side of equation (76) represents the weighted sum the reaction-mass acceleration $a_r$, the baseplate acceleration $a_b$, and the relative acceleration $\delta''$.

Figure 5:
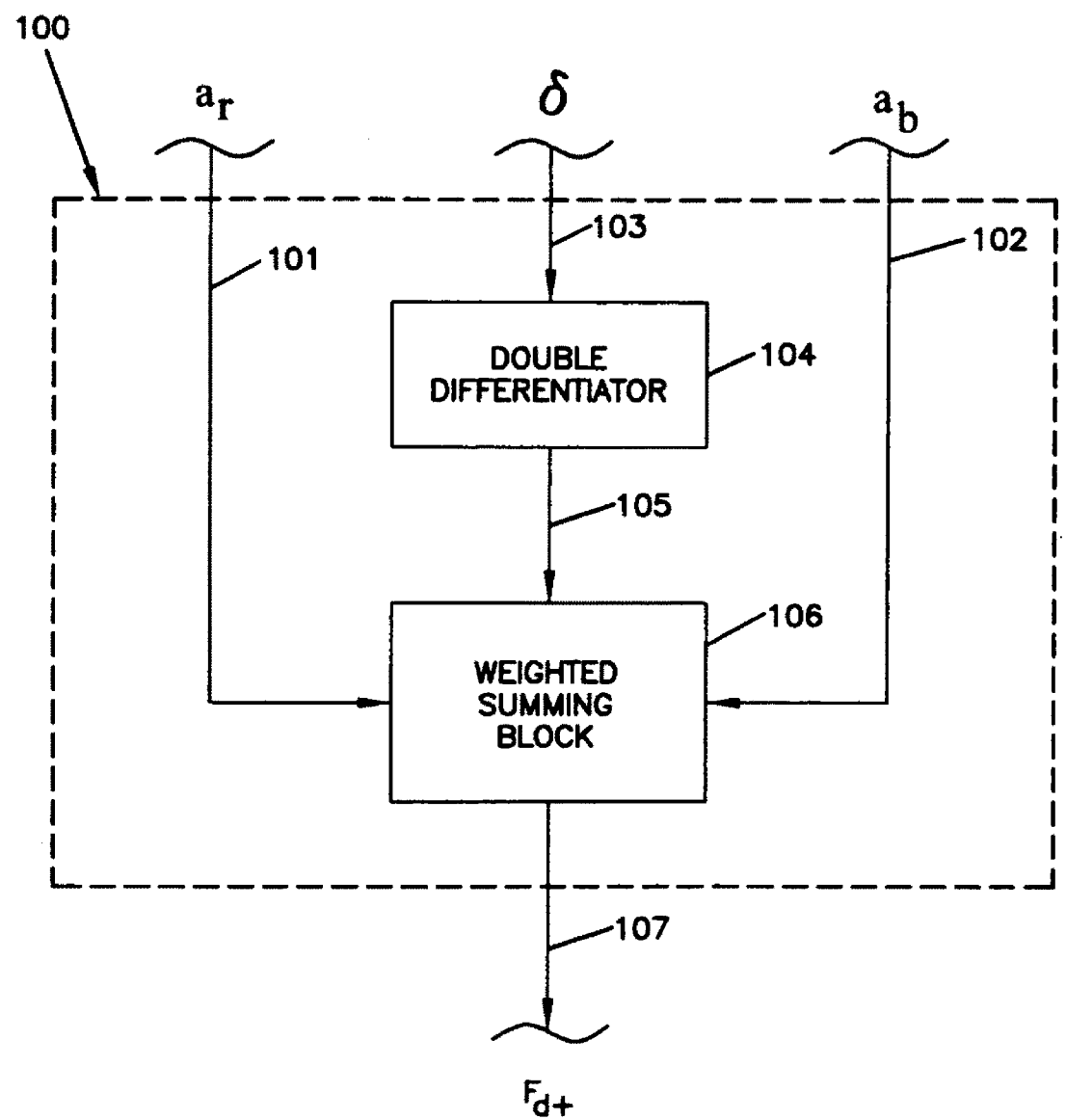
FIG. 5 is a schematic, diagrammatic view of a weighted-sum driving force estimation system 100 constructed in accordance with the present invention.

FIG. 5 shows a weighted-sum driving force estimation system 100 configured to produce an output representative of the driving force output of a reciprocating actuator. The weighted-sum driving force estimation system 100 has three input signals: a reaction-mass acceleration signal $a_r$ input via signal path 101, a baseplate acceleration signal $a_b$ input via signal path 102, and a relative displacement signal $\delta$ input via signal path 103. The reaction-mass acceleration signal $a_r$ is representative of the acceleration of the reaction-mass of the reciprocating actuator. The baseplate acceleration signal $a_b$ is representative of the acceleration of the baseplate of the reciprocating actuator. The relative displacement signal $\delta$ is representative of the relative displacement of the reaction-mass relative to the baseplate.

The relative displacement signal $\delta$ is input via signal path 103 to a double differentiator 104 which produces an output signal representative of the second time derivative $\delta''$ of the relative displacement signal. The second time derivative $\delta''$ of the relative displacement signal is equivalent to a relative acceleration signal. The double differentiator 104 can be provided with a high-cut filter as needed to attenuate high-frequency noise produced by the differentiator. The relative acceleration signal $\delta''$ output by the double differentiator 104 is provided via signal path 105 to a weighted summing block 106.

The weighted summing block 106 receives three input signals: the relative acceleration signal $\delta''$ received via signal path 105, the reaction-mass acceleration $a_r$ signal received via signal path 101, and the baseplate acceleration signal $a_b$ received via signal path 102. The weighted summing block 106 produces the weighted sum of the three input signals in accordance with equation (76) and the description thereof. The weighting coefficient of the relative acceleration signal $\delta''$ is also scaled by an additional factor representative of the amplitude scale of the relative displacement signal $\delta$. The relative displacement signal $\delta$ is measured by a different kind of sensor than the baseplate and reaction-mass acceleration signals, so the amplitude values of the relative acceleration signal $\delta''$ may represent different scale units that the amplitude scale units of the baseplate acceleration signal and the reaction mass acceleration signal. Therefore, the weighting coefficient of the relative acceleration signal $\delta''$ is scaled by a factor to substantially compensate for any difference in the scaling of the relative acceleration signal $\delta''$ as compared to the baseplate acceleration signal $a_b$ and the reaction-mass acceleration signal $a_r$. The weighted summing block 106 provides the weighted sum as an output signal on signal path 107.

The weighted sum output signal on signal path 107 is the output signal of the weighted-sum driving force estimation system 100. The weighted sum signal output on signal path 107 is representative of the driving force output of the reciprocating actuator.

The relative displacement measurement can also be used to produce a combined estimate of the baseplate acceleration and a combined estimate of the reaction mass acceleration:

$$a_{r+} = \frac{(\sigma + \delta'')}{2}, \tag{77}$$

$$a_{b+} = \frac{(\sigma - \delta'')}{2}, \tag{78}$$

where
- $a_{r+}$ is a combined estimate of the reaction-mass acceleration, adjusted by the second derivative of the relative displacement measurement;
- $a_{b+}$ is a combined estimate of the baseplate acceleration, adjusted by the second derivative of the relative displacement measurement;
- $\sigma = a_r + a_b$, which is the sum of the non-adjusted reaction-mass acceleration signal $a_r$ and the non-adjusted baseplate acceleration signal $a_b$;
- $\delta = x_r - x_b$, which is the relative displacement of the reaction-mass position $x_r$ relative to the baseplate position $x_b$, as measured by a displacement transducer; and $$\delta'' = \frac{d^2\delta}{dt^2},$$

which represents the second derivative of the relative displacement with respect to time, so is therefore representative of relative acceleration.

Another method for combining the three signals is to double-integrate the baseplate acceleration and the reaction-mass acceleration signals to produce a baseplate displacement signal and a reaction-mass displacement signal which can be combined with the relative displacement signal. The baseplate acceleration and the reaction-mass acceleration may each be double-integrated separately and them summed, or the baseplate acceleration and the reaction-mass acceleration may be first summed and then the sum double-integrated.

Integrating the reaction-mass acceleration and the baseplate acceleration produces displacement signals which can be combined with the relative displacement measurement to produce a combined estimate of the reaction-mass displacement and a combined estimate of the baseplate displacement, as described by the following equations:

$$x_{r+} = \frac{(\xi + \delta)}{2} \tag{79}$$

$$x_{b+} = \frac{(\xi - \delta)}{2} \tag{80}$$

where
- $x_{r+}$ represents a combined estimate of the reaction-mass displacement, adjusted by the relative displacement measurement;
- $x_{b+}$ represents an combined estimate of the baseplate displacement, adjusted by the relative displacement measurement;
- $\xi = \iint \sigma dt\, dt = \iint (a_r + a_b) dt\, dt = \iint a_r dt\, dt + \iint a_b dt\, dt = x_r + x_b$, which is the double time-integral of the sum of the non-adjusted reaction-mass acceleration signal $a_r$ and the non-adjusted baseplate acceleration signal $a_b$, so $\xi$ represents the sum of the non-adjusted displacements of the reaction-mass and baseplate as determined from acceleration measurements;
- $\delta = x_r - x_b$, which is the relative displacement of the reaction-mass position $x_r$ relative to the baseplate position $x_b$, as measured by a displacement transducer.

The combined estimate of the baseplate displacement $x_{b+}$ may be used for determining a combined estimate of baseplate velocity and a combined estimate of baseplate acceleration:

$$v_{b+} = x'_{b+} = \frac{d(x_{b+})}{dt}, \quad (81)$$

$$a_{b+} = x''_{b+} = \frac{d^2(x_{b+})}{dt^2}. \quad (82)$$

Combined estimates of the reaction-mass velocity and of the reaction-mass acceleration may be determined in a similar way.

These combined, adjusted estimates of the baseplate motions—baseplate displacement $x_{b+}$, baseplate velocity $v_{b+}$, and baseplate acceleration $a_{b+}$—are estimates of the driving-point motions of the substrate material, and may be used in combination with the actuator force $F_{g+}$ to determine the elastic properties of a substrate material upon which the actuator exerts a force.

Each of the signals used to produce an adjusted estimate of the actuator output—the relative displacement $\delta$, the reaction-mass acceleration $a_r$, and the baseplate acceleration $a_b$—can also be corrected by applying the fractional-cycle-interval filter method to estimate and attenuate measurement error and/or integration error while substantially preserving the phase and amplitude relationships of components of the signals which are harmonics of a continuous-phase reference signal. The error correction may be applied to the signals before producing a combined, adjusted estimate of the actuator output, and/or the error correction may be applied to the combined, adjusted estimate after producing the estimate.

These methods for determining an estimate of the output force and/or of the motions of a reciprocating actuator by combining the three measurements—the relative displacement $\delta$, the reaction-mass acceleration $a_r$, and the baseplate acceleration $a_b$—are useful, because the relative displacement measurement is independent of the acceleration measurements, and incorporating all three measurements produces an improved estimate of the actuator output force and motions.

It is known in the art that the weighted sum estimate of the driving force of a reciprocating actuator may differ somewhat from the actual driving force, due to various factors that depend on mechanical properties of the actuator, comprising any one or more of the following: inaccuracy in the inertial mass attributed to the baseplate, inaccuracy in the inertial mass attributed to the reaction mass, inaccuracy in measurement of the acceleration of the reaction mass and the baseplate, flexing of the baseplate at high frequencies, imperfect coupling of the reaction-mass force to the baseplate, imperfect isolation of the baseplate from the holddown apparatus, rocking motion of the baseplate and/or reaction mass, and combinations thereof. The driving-point analyzer system can compensate for errors in the weighted sum driving force signal which are attributable to mechanical properties of the actuator, the compensating being accomplished by using a differential equation model comprising terms which represent a dynamic mechanical response of one or more elements of the actuator, and including motion signals and basis-function signals corresponding to the motion of elements of the actuator, in addition to the driving-point motion of the baseplate.

9. Spectral Estimation Using Fractional-cycle-intervals

When evaluating the performance of error attenuation methods, or evaluating the performance of methods for determining the elastic properties of real, nonlinear elastic materials, it is useful to have a means to estimate spectral amplitude and phase of anharmonic components of driving-point motion signals at frequencies that are harmonics of the driving force. Such spectral estimates are also useful for evaluating the performance of dynamic actuators acting upon elastic materials, and useful for representing the anharmonic components of the response of elastic materials in the frequency domain. It is an objective of the present invention to estimate the spectral amplitude and phase of anharmonic components of driving-point motion signals or actuator output signals at frequencies that are harmonics of a known continuous-phase signal, while substantially preserving the relative amplitude and relative phase relationships of these harmonic components.

I disclose in the present invention a system and a method for spectral estimation of harmonic component frequencies of an input signal at harmonics of a known continuous-phase signal with a known phase function, using the method of fractional-cycle-interval phase sampling, the method comprising the following:

(pp) determining a series of time values at equal intervals of phase of the known phase function, wherein the equal intervals of phase are fractional-cycle intervals;

(qq) sampling the input signal at the time points represented by the series of time values so determined, to produce a phase-sampled signal;

(rr) estimating the spectral components of the phase-sampled signal so produced, to produce an estimated spectral function representative of the spectral components of the phase-sampled signal.

The method has two distinct inputs: an input signal (symbolized herein by S(t)), and a phase function (symbolized herein by $\phi$(t)). The phase function is representative of the known phase of a continuous-phase signal (symbolized by P(t)).

Step (pp) and step (qq) are in accordance with the fractional-cycle-interval filter steps (pp) and (qq) already described herein supra in complete detail. Step (uu) is different. In step (uu), instead of applying a filter, spectral analysis is applied to the phase-sampled signal. The spectral analysis provides a means to estimate an amplitude spectrum and/or a phase spectrum of harmonic components of the phase-sampled signal. The spectral analysis comprises any of various spectral analysis methods known in the art, including but not limited to a Fourier analysis method (e.g. Fast Fourier Transform or Discrete Fourier Transform), or a Maximum Entropy Method (Press et al., *Numerical Recipes in C*, Cambridge University Press, 1988, pp. 447-452).

The spectral components produced by this method are not temporal frequencies, because the signal being analyzed is a phase-sampled signal. The spectral components are pseudo-frequencies of phase components relative to the known phase function, and these phase components are in units of cycles-per-radian. The amplitude and phase relationships of the spectral components that are harmonics of the known phase function are substantially preserved, and these harmonic components are sharply resolved by this method. The pseudo-frequency values in units of cycles-per-radian may be converted to units of cycles-per-second based on the instantaneous frequency of the known phase function used as the basis of the fractional-cycle-interval phase sampling.

It is well known in the art of spectral estimation that there is a trade-off in resolution between the length of the analysis window and the frequency resolution of the spectral estimation. A longer window is needed to obtain higher resolution estimate of components frequencies. However, for a swept-frequency signal wherein frequency is changing continuously with time, a longer window includes a wider range of frequencies in the sweep, and therefore the spectral estimation will be smeared over the entire frequency range of the sweptsignal within the window. It is not possible with conventional temporal frequency estimation methods to obtain a sharply resolved estimate of harmonic frequency components in a swept-frequency signal within a short time window. An advantage of using spectral analysis of a fractional-cycle-interval phase-sampled signal is that this method provides a sharply resolved spectral estimate of harmonic frequency components that are harmonics of the known phase function.

Figure 6:
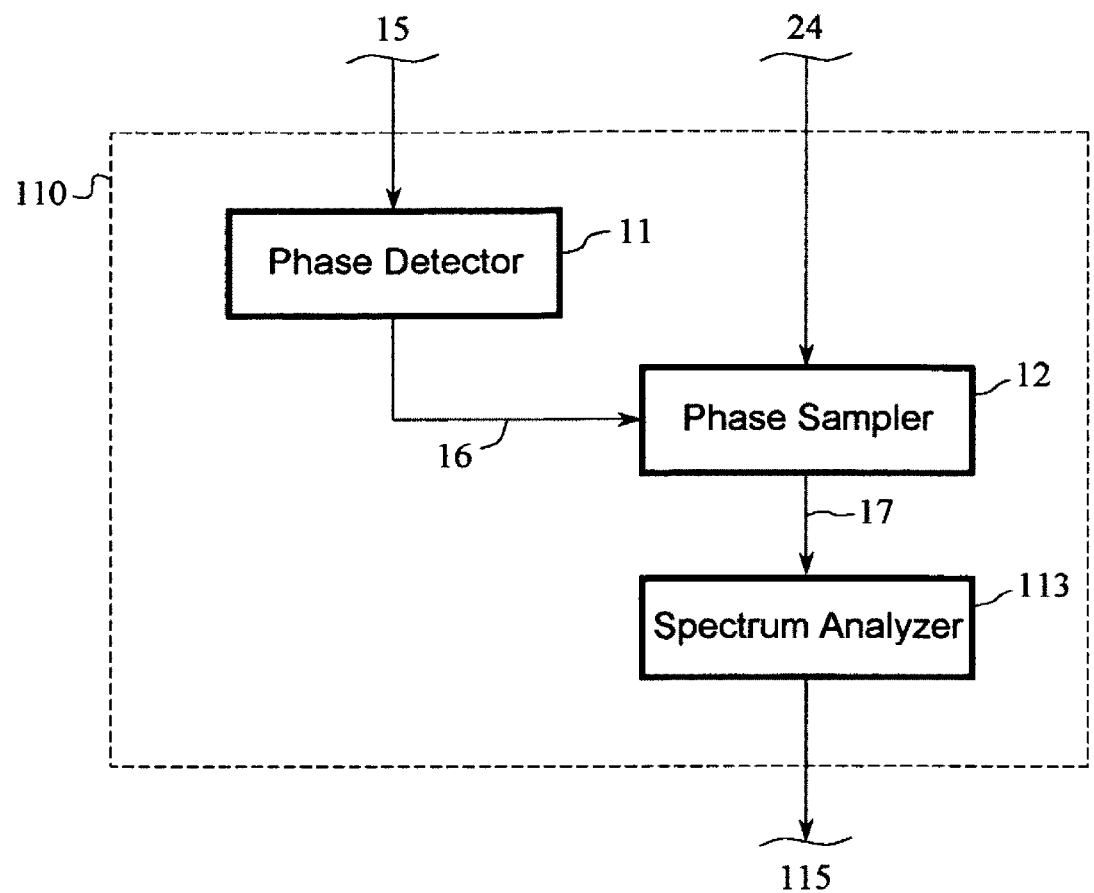
FIG. 6 is a schematic, diagrammatic view of a fractional-cycle-interval spectral analyzer system 110 constructed in accordance with the present invention.

FIG. 6 shows a fractional-cycle-interval spectrum analyzer system constructed in accordance with the present invention and designated by the reference numeral 110. The fractional-cycle-interval spectral analyzer system 110 is provided with a phase detector 11, a phase sampler 12, and a spectrum analyzer 113. The phase detector 11 and the phase sampler 12 operate in accordance with the description already given herein in conjunction with the fractional-cycle-interval filter 10. Referring to FIG. 6., in operation the fractional-cycle-interval spectrum analyzer 110 receives an input signal to be analyzed and a phase reference signal. The phase reference signal is communicated to the phase detector 11 via signal path 15. The phase detector 11 detects the phase of the phase reference signal and produces a phase-sample timing signal representative of a series of times of fractional-cycle-intervals. The phase-sample timing signal is provided to the phase sampler 12 over signal path 16. An input signal to be analyzed is input via signal path 24 to the phase sampler 12. The phase-sample timing signal received over signal path 16 triggers the phase sampler 12 to sample the input signal at the end of each fractional-cycle interval. The series of sample values produced by the phase sampler 12 are output via signal path 17 to the spectrum analyzer 113. The series of samples output by the phase sampler 12 are representative of a phase-sampled signal. In effect, the phase sampler 12 converts the input signal from being a function of time to being a function of phase, based on the phase of the phase reference signal. The spectrum analyzer 113 estimates a frequency spectrum of the phase sampled signal, and outputs a signal representative of the frequency spectrum on signal path 115.

The frequency spectrum output of the spectrum analyzer 113 comprises the output of the fractional-cycle-interval spectrum analyzer system 110. The frequency spectrum output comprises a spectrum of the input signal at harmonics of the phase reference signal. One embodiment of the frequency spectrum output is in the form of a complex-valued signal representative of the spectrum. Another embodiment of the frequency spectrum output is in the form of an amplitude spectrum and/or a phase spectrum.

Figure 8A:
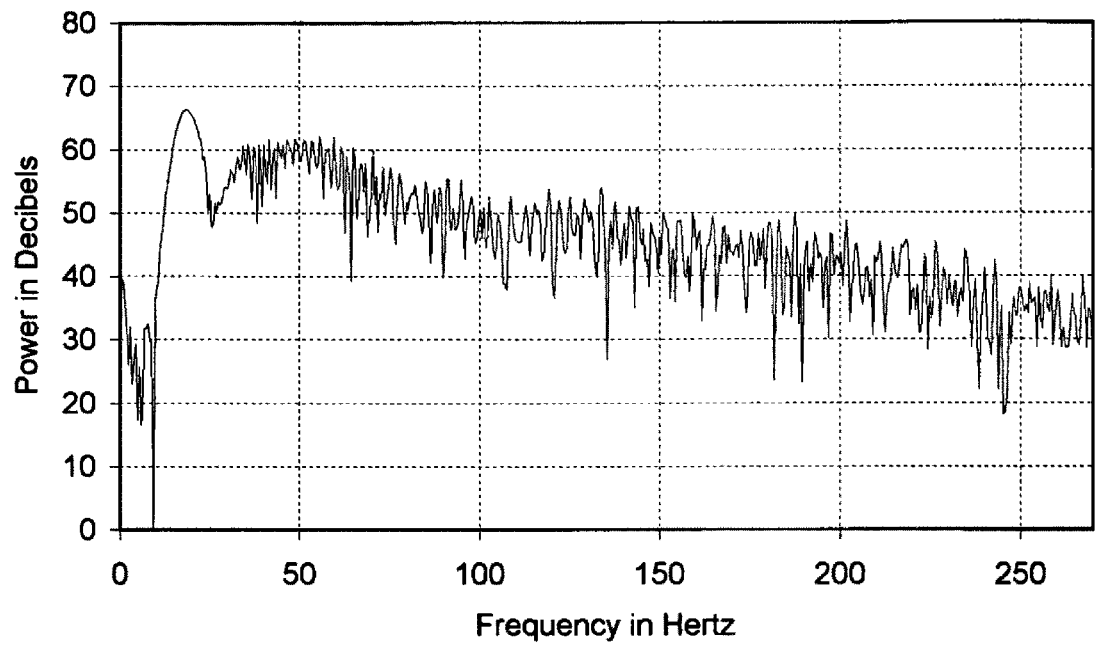
FIG. 8A is a plot of a power spectrum of a driving-point acceleration signal measured from a seismic vibrator on soil (Example 1), wherein the power spectrum is produced by conventional FFT method.
Figure 8B:
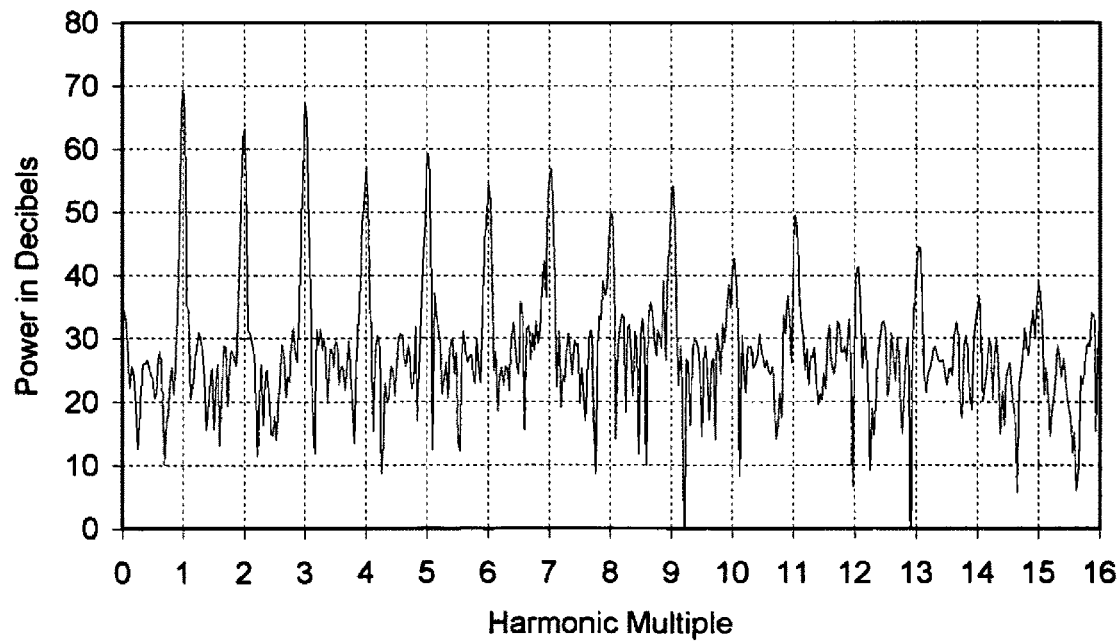
FIG. 8B is a plot of a harmonic power spectrum produced by a fractional-cycle-interval spectrum analyzer system 110 using the same acceleration signal as in FIG. 8A, showing the advantages provided by the present invention.

An example of a harmonic power spectrum produced by an embodiment of the fractional-cycle-interval spectrum analyzer 110 is shown in FIG. 8B and described in Example 1.

It is understood by skilled practitioners that any of the various forces described herein can be expressed as pressure or stress by dividing the force by the surface area size of the corresponding contact surface area over which the force is applied. The elasticity and viscosity relationships have been described herein in terms of force solely for purposes of clarity and uniformity of the description, and can be expressed in terms of pressure or stress without changing the substance, logic, or scope of the present invention.

It should be understood that all of the signals, processes, steps, or equations of the several methods of the present invention have been shown and described separately herein for the sole purpose of clearly identifying the information being used in each of the individual steps or processes and the method or process used in each of the steps. In practice, the signals, processes, steps, or equations may be separate or combined so long as the logic of the method is executed substantially as described herein.

It should be understood that any of the intermediate values of any one or more of the signals described herein may be stored; and each of the methods may be practiced, and each of the systems may be operated, in separate, discontinuous stages by retrieving the stored signal values, so long as the logic of the method is executed substantially as described herein.

It should be understood that all of the signal paths and components, blocks, or systems of the several systems have been shown and described separately herein for the sole purpose of clearly identifying the information being communicated between each of the individual components of the system and the operation of each of the components. In operation, the signal paths and components, blocks, or systems may be separate or combined so long as the logic of the system is executed substantially as described herein.

It should also be understood that each system described herein can be embodied as: one or more software program executing on one or more suitable processors, microprocessors, digital signal processors, or computers; a plurality of discrete or integrated electrical components; and/or combinations thereof.

It will become apparent to one skilled in the art that changes may be made in the construction and the operation of the various components, elements, and systems described herein and changes may be made in the steps or the sequence of steps of the methods described herein without departing from the spirit and scope of the invention as described.

EXAMPLES

Example 1

Elastic properties of the soil at the surface of the earth at a test location were determined from the driving-point response of the soil, using an embodiment of the systems and methods of the present invention. A seismic vibrator actuator generated the driving force applied to the soil, and a vibrator control system acquired signals representative of the driving-point response of the soil. The soil being tested was in situ, in place at the surface of the earth.

Background

Seismic vibrators are designed for use as a seismic energy source for imaging the subsurface of the earth using various seismic surveying systems and methods which are well known. In the seismic surveying methods, a seismic vibrator applies a vibrating force to a surface of the earth at a source location, generating elastic waves which propagate into the earth and are subsequently received by one or more seismic sensors. A seismic data acquisition system synchronizes the seismic vibrator and the seismic sensors, and records the seismic sensor signals. In a typical seismic survey, a plurality of seismic vibrators can be used, and each seismic vibrator vibrates at many distinct source locations throughout the survey area, to produce a collection of many distinct seismic recordings. The collection of seismic recordings is processed to produce a seismic image of the subsurface geology of the survey area.

To serve this purpose efficiently, a seismic vibrator is designed to generate large, dynamic vibration forces in a controlled manner, to maximize the power of elastic-wave energy that is transmitted into the earth and received at the seismic sensors with optimal signal strength. In seismic surveying operations, the time duration that vibrations are applied at each source location is limited by economic considerations, to minimize the elapsed time and economic cost of the survey, while still achieving the seismic imaging objective.

To achieve the seismic surveying objectives, the vibration forces and motions generated by a seismic vibrator during seismic surveying typically exceed the small amplitude approximation of linear elastic models. The high power output of seismic vibrators produces a non-linear elastic response at the driving-point. Also, due to practical economic limitations, the duration of the applied vibration force is typically too short to approximate steady-state motions.

Therefore, the driving force and driving-point motions generated by a seismic vibrator during typical seismic surveying comprise an anharmonic superposition of harmonics of the driving-force caused by the non-linear elastic response, and also comprise a superposition of both a steady-state component and a transient component. The transient component also comprises a superposition of a set of harmonics.

A typical current practice has been to use a Laplace transform method or various related frequency domain methods to determine elastic properties from driving-point motions, including driving-point motions generated by seismic vibrators engaged in seismic surveying. These methods are based on applying a Laplace transform to a differential equation of motion of a linear spring-damper model, converting the equation to a Laplace domain representation wherein a complex-vector ratio of the driving force to the driving-point motion results in a simple algebraic relationship. In these methods, the elastic properties are typically derived by fitting a curve to a frequency domain representation of the complex ratio of the driving force signal to the driving-point motion signal. If the driving-point motion used is the driving-point velocity, the complex-vector ratio of the driving force to the driving-point velocity is also known as the mechanical impedance or the complex impedance. This type of solution method is also called a transfer function solution. An explicit mathematical requirement in these Laplace transform and related methods is that both the driving force and the driving-point motion must approximate steady-state, pure sinusoidal signals. The presence of anharmonic signal components (also called harmonic distortion) or transient components invalidates the mathematical basis of these Laplace Transform methods. Skilled practitioners have tried to work around these limitations by combinations of several well known methods, including but not limited to 1) applying tracking filters to the driving-point response signals, to attenuate all anharmonic and transient components other than the fundamental driving frequency; 2) restricting the magnitude of the driving force to within the limitations of the small-amplitude approximation to obtain an approximately linear elastic response; and 3) applying the driving force for sufficiently long duration to reach steady-state motions. An implicit assumption is that the transient and harmonic signal components are sufficiently attenuated that the Laplace transform methods produce a fair approximation of the true elastic properties.

For example, Hamblen, et al. (U.S. Pat. No. 6,604,432) teach a Laplace transform type method for determining the mechanical stiffness of soil from the complex ratio of driving force to driving-point acceleration, or alternatively from the complex ratio of driving force to driving-point displacement. Hamblen, et al. require in their method that the amplitude of the driving force must be limited to a low level, and they suggest that tracking filters be applied to the driving force and displacement signals to attenuate all signal components other than the fundamental driving frequency. Hamblen's method produces a single value of stiffness by taking an average over a wide range of frequencies.

In contrast, the systems and methods of the present invention are free of mathematical limitation in the accurate use of anharmonic or transient signal components. The present example shows how the systems and methods of the present invention were used to determine in situ elastic properties of a test location on the surface of the earth using a seismic vibrator actuator to generate a high amplitude, short duration driving force. The amplitude of the driving force used for the present example exceeds the small-amplitude approximation, and the resulting elastic response was a non-linear, anharmonic driving-point response including transient components. The values of first-order stiffness and first-order viscosity were determined as a function of frequency, which provided a means for analysis to determine a depth-profile of shear-wave speed.

One use for the elastic properties so determined is for improving the seismic image produced by seismic surveying. The elastic properties at and near the surface of the earth are typically highly variable, which causes distortions in the seismic image of the deeper geologic features. The elastic wavefield becomes distorted as it propagates through the near-surface material, both when it is radiated from the energy source and when it is received at the seismic sensors. These distortions can be characterized as static time delays, phase shifts, frequency dependent attenuation, critical-angle reflections, elastic wave mode conversions, and other elastic wave propagation effects. If the elastic properties of the near-surface material are known, seismic imaging methods can reduce the effects of the near-surface distortions to improve the resulting image of the deeper features. In particular, it is useful to know a profile of the seismic wave-speed in the near-surface material.

One method in seismic surveying practice for determining near-surface wave-speed is to drill a bore-hole and directly measure a depth profile of seismic wave-speed between the surface and one or more sub-surface depth levels within the bore-hole. This bore-hole measurement method is called an "up-hole" method in the seismic surveying art. This method is relatively time-consuming and economically costly, and it is typically impracticable to obtain measurements for more than a few, widely spaced bore-holes. Several advantages of determining the near-surface elastic properties by using the driving-point response produced by a seismic vibrator during seismic surveying are that the properties can be determined at each seismic vibrator source location, which is exactly where the properties are most useful; the seismic vibrator source locations are typically closely spaced, which allows for good measurement of the spatial variation of the near-surface properties; and no additional time or effort is incurred beyond what is already required for the seismic surveying operation. It is therefore an advantage to be able to determine the elastic properties from a driving-point response comprising both transient and steady-state responses, and comprising a driving force that exceeds the small-amplitude approximation.

Another use for the near-surface elastic properties is in the field of civil engineering. The elastic properties of soil and other materials at and near the surface are important factors influencing the design and construction of structures, roads, excavations, embankments, tunnels, and other types of foundations and earth works. For many structures, the elastic properties of the foundation soil must be measured and sometimes modified by various construction methods (such as compaction, fill, or excavation), and then verified, to meet the design criteria of the structure. An advantage of using the driving-point response systems and methods of the present invention is that they provide a means to quickly and efficiently determine elastic properties at a large number of driving-point locations using relatively short duration chirps and relatively large amplitude driving forces.

Richart, et al. have shown that the driving-point response of an elastic half-space can be represented by a differential equation model of an equivalent spring-damper model (Richart, F. E. Jr., 1970, *Vibrations of Soils and Foundations*, Prentice-Hall, p. 191-213). Richart teaches that the coefficients of stiffness and viscosity for the equivalent spring-damper model are not constants; the values of the coefficients of stiffness and viscosity are complicated functions of the frequency of the driving force and of the properties of the elastic half-space—the density, shear modulus, and Poisson's ratio. Lysmer presents a solution for the coefficients of stiffness and viscosity for the particular case of a rigid circular disk applying a vertical driving force to a horizontal surface of an elastic half space (Lysmer and Richart, 1966, "Dynamic response of footings to vertical loading", Journal of the Soil Mechanics and Foundations Division, Proc. ASCE, vol. 92, no. SM 1, p. 65-91). The response for the case of a rigid rectangular footing has also been studied, and Richart, et al., teach that the driving-point response of an elastic half-space to a vertical driving force applied by a rigid rectangular footing can be reasonably approximated by the response of a rigid circular disk of the same surface area size.

For the soil under test in the present example, the properties of the soil vary with depth below the baseplate. The elastic half-space solution presented by Lysmer (1966) is for a homogeneous half-space. The majority of the elastic-wave energy which is radiated into the elastic material by the driving force comprises Rayleigh waves propagating along the surface of the material (F. E. Richart, Jr., et al., 1970, Prentice-Hall, p. 91). Because it is a surface wave, the Rayleigh wave generation and propagation are influenced predominately by the properties of the elastic material within about one wavelength of the surface. In particular, it has been observed that the Rayleigh wave propagation speed can be approximated by the elastic properties at a depth of about one-half the wavelength of the Rayleigh wave (F. E. Richart, Jr., et al, 1970, Prentice-Hall, p. 115-118). Therefore, it can be assumed that the driving point response of the soil under test will be predominantly influenced by the elastic properties at a depth of about one-half the wavelength of the Rayleigh wave radiated by the driving force.

Experimental Procedure

In the present example, the elastic material being tested was in situ soil at the surface of the earth along with underlying geologic formations. A seismic vibrator actuator generated the driving force applied to the soil. The seismic vibrator was a servo-hydraulic, reciprocating actuator positioned in a vertical orientation, also known as a P-wave vibrator. Description of the actuator is listed in Table 1.

TABLE 1

| | |
|---|---|
| Actuator used for Example 1: | class: reciprocating actuator |
| | type: servo-hydraulic seismic vibrator |
| Reaction-mass weight: | 3039 kilograms |
| Baseplate weight: | 1361 kilograms |
| Baseplate surface area: | 2.5 square meters; |
| | radius of an equivalent circular area: |
| | $r_0$ = 0.9 meter |
| Orientation: | Vertical; The driving force output was a normal force, applied in a vertical direction perpendicular to the baseplate contact surface area. |
| Driving force reference signal: | swept-frequency chirp |
| Duration of chirp: | 8 seconds |
| Starting frequency: | 8 Hertz |
| Ending frequency: | 82 Hertz |

TABLE 1-continued

| | |
|---|---|
| Frequency function: | linear frequency increase with time |
| Amplitude envelope function: | constant amplitude with 250 millisecond starting and ending cosine tapers |

The baseplate of the seismic vibrator was in direct contact with the soil. Driven by the actuator, the baseplate applied a vertical, reciprocating driving force in a direction perpendicular to the surface of the soil (a normal force). The amplitude of the driving-force generated by the seismic vibrator in this example was approximately 200,000 Newtons.

As is standard practice for seismic vibrators, the seismic vibrator actuator was provided with a hold-down mechanism which applied a static, downward hold-down force to the baseplate, to maintain mechanical contact coupling of the baseplate to the surface of the soil. The amplitude of the driving force was limited such that the upward directed driving force would not exceed the downward directed static hold-down force, thereby preventing the baseplate from jumping off the ground. The static hold-down force was produced by the static weight of the vehicle on which the actuator is mounted. The hold-down mechanism was coupled to the baseplate by airbag isolators, and the hold-down force was applied through the airbag isolators which substantially isolate the driving-point motions of the baseplate from being transferred to the hold-down mechanism.

An actuator control system controlled the amplitude and phase of the driving-force output of the seismic vibrator to substantially match a continuous-phase reference signal. Table 1 gives the parameters of the reference signal used for the present example. The reference signal was a swept-frequency chirp from 8 to 82 Hertz, 8 seconds duration, with a linear frequency function. The control system comprised both phase control and amplitude control. The control system monitored the actuator output driving force while the driving force was being generated, and adjusted the actuator drive to optimize the similarity of the driving force to the reference signal. To monitor the driving force, the control system used a weighted sum estimate of the driving force, which is the sum of the reaction-mass acceleration and the baseplate acceleration each multiplied by a factor proportional to their corresponding inertial mass. For the results described in this Example 1, the control system reported a maximum phase error of less than 3 degrees phase difference between the reference signal and the fundamental frequency of the actuator output driving force, and reported the average phase error was 1.25 degrees.

The actuator control system measured the reaction-mass acceleration in the vertical direction with a reaction-mass acceleration sensor, and measured the baseplate acceleration in the vertical direction with a baseplate acceleration sensor, to produce a reaction-mass acceleration signal and a baseplate acceleration signal. The reaction-mass acceleration signal and the baseplate acceleration signal were output by the control system as digitally sampled signals, sampled at one millisecond sample intervals throughout the duration of the 8 second chirp.

The reaction-mass acceleration signal and the baseplate acceleration signal produced by the control system represent the driving-point response of the soil at the driving-point location.

A driving-point analyzer system processed the driving-point response signals in accordance with the systems and methods of the present invention to determine elastic properties of the soil at the driving point location. The particular embodiment of the driving-point analyzer system which was used for this example was constructed and operated in accordance with the system depicted schematically in FIG. 3 and the description thereof, and in accordance with the component systems depicted in FIG. 2 and FIG. 4 and descriptions thereof, except for several specific differences.

Specific details of the configuration and operation of the particular driving-point analyzer system which was used for the present example are listed in Table 2. The specific differences from the embodiment depicted in FIG. 3 are described as follows:

1.01> In this example, a driving-force signal was not received directly as an input signal to the driving-point signal conditioner 60. Instead, a driving-force signal was generated by a different embodiment of a driving-point signal conditioner by means of a weighted sum of an error-corrected reaction-mass acceleration signal and a final error-corrected baseplate acceleration signal.

FIG. 7 shows in schematic form the specific embodiment of the driving-point signal conditioner 60a which was used for the present example, designated by the reference numeral 60a for clarity to distinguish this particular embodiment. The driving-force signal conditioner 60a was configured to be capable of generating a weighted sum driving-force signal.

1.02> Referring to FIG. 7, the error attenuator 20d received the reaction-mass acceleration signal via signal path 61.

The error attenuator 20d (FIG. 7) was configured and operated in accordance with the error attenuator 20a (FIG. 4) and the description thereof. The error attenuator 20d estimated and attenuated error in the reaction-mass acceleration signal in the same way that error attenuator 20a estimated and attenuated error in the baseplate acceleration signal (received via signal path 38).

The output of the error attenuator 20d was an error-corrected reaction-mass acceleration signal $a_R$ which was output via signal path 63.

1.03> The driving-point signal conditioner 60a was provided with a weighted summing component 65, for forming the weighted sum driving force signal. The weighted summing component was provided with two input signals: the error-corrected reaction-mass acceleration via signal path 63, and a final error-corrected baseplate acceleration signal received on signal path 64 via 51. The weighted summing component 65 produced a weighted sum of the two input signals, each weighted by a factor proportional to their respective inertial masses (as listed in Table 1). The operation of the weighted summing component 65 can be represented mathematically as follows:

$$F_d = -M_R a_R - M_B a_B \qquad (83)$$

where $F_d$ represents the driving-force signal, output on signal path 62;

$a_R$ represents the error-corrected reaction-mass acceleration signal (path 63);

$a_B$ represents the final error-corrected baseplate acceleration signal (path 64);

$M_R$ represents the inertial mass of the actuator reaction-mass;

$M_B$ represents the inertial mass of the actuator baseplate.

The polarity of the two accelerations $a_R$ and $a_B$ is negative in equation (83) because the driving force acting on the soil is equal and opposite to the net accelerating forces acting on the reaction-mass and baseplate.

The weighted sum signal so produced on signal path 62 represents an error-corrected driving force signal which is output from the driving-point signal conditioner 60a.

The driving-point signal conditioner 60a shown in FIG. 7 comprises an embodiment of a weighted sum driving-force error-correction system to attenuate measurement error in a weighted sum force signal representing the output force of a reciprocating actuator.

Other than the several differences described herein, the components and operation of driving-point signal conditioner 60a (FIG. 7) used for the present example were the same as the corresponding components and operation described herein for the driving-point signal conditioner 60 (FIG. 3). The output signal paths 51, 47, and 43 are shown in FIG. 7 in a different order than shown in FIG. 3, but this difference is solely for clarity of the schematic representation in the figure, and does not represent a material departure from the operation or components described herein and shown in FIG. 3.

TABLE 2

| COMPONENT OR SIGNAL | REFERENCE NUMERAL | CONFIGURATION USED FOR EXAMPLE 1 |
|---|---|---|
| Driving-Point Acceleration Signal | 38 | The baseplate acceleration signal which was measured by the actuator control system is representative of the driving-point acceleration in the vertical direction, and comprised a digital signal at 1 msec sample intervals, input on signal path 38. |
| Continuous-Phase Reference Signal | 15a | The driving-force reference signal was represented in parametric form by the parameters describing the swept-frequency chirp; the chirp parameters (Table 1) were configured into the phase detector 11a. |
| Reaction-Mass Acceleration Signal | 61 | The reaction-mass acceleration signal which was measured by the actuator control system is representative of the reaction-mass acceleration in the vertical direction, and comprised a digital signal at 1 msec sample intervals, input on signal path 61. |
| Driving-Force Signal | 62 | Generated by the weighted sum of reaction-mass and baseplate acceleration signals in accordance with equation (83) and the description thereof in detail item 1.03. |

TABLE 2-continued

| COMPONENT OR SIGNAL | REFERENCE NUMERAL | CONFIGURATION USED FOR EXAMPLE 1 |
|---|---|---|
| Phase Detector | 11a | Configured for 32 equal phase intervals per cycle. The phase-sample timing signal was generated in accordance with equation (87) and the description thereof in detail item 1.05 |
| Error Attenuators | 20a 20b 20c 20d | All four error attenuators were configured with the same parameter settings for each of their respective components. The parameter settings for the phase samplers 12, the harmonic filters 13, and the re-samplers 14 are listed below. |
| Phase Sampler | 12 | Sampling by cubic spline interpolation at the sequence of fractional-cycle-interval times represented by the phase-sample timing signal produced by phase detector 11a |
| Harmonic Filter | 13 | Digital filtering in accordance with equations (88) and (89) and the description thereof. |
| Re-sampler | 14 | Re-sampling by cubic spline interpolation at uniform time intervals of 1 millisecond. |
| Notch Filter | 21 | Not used in this example embodiment. |
| First Integrator Second Integrator | 31 32 | Numerical integration by alternative extended Simpson's rule, described by Press, et al. (Press et al., 1988, Numerical Recipes in C, Cambridge University Press, pp. 112-117). |
| First Differentiator Second Differentiator | 33 34 | Numerical differentiation by a five-point central difference method. |
| Model Basis Function Generator | 71 | Generated basis function signals for the differential equation models described in Table 3. |
| Design Matrix Former | 72 | Two example modes: first mode: single time window: 1.5 to 1.7 sec. second mode: sequence of overlapping time windows; 500 msec length of each window; 10 msec start time increment per window. |
| Solver System | 80 | Numerical solution was by singular value decomposition, based on description by Press et al. (Press et al., 1988, Numerical Recipes in C, Cambridge University Press, pp. 60-72, pp. 534-539, and pp. 556-557) |
| Divider | 85 | In this example, singular values never fell below the minimum threshold, so the entire SVD vector space was used to produce the solution results. No singular value division results were set to zero by the divider. |
| Solution Error Block | 86 | Not used in this example embodiment. |

Several of the parameters and operations used for the present example are described in detail as follows:

1.04> The polarity of the motion and force signals used was such that a motion or force directed in the upward, vertical direction was assigned a positive signal polarity. Thus, a compressive driving force had a negative signal value, and an extensional driving force had a positive signal value.

1.05> The continuous-phase reference signal was embodied in the form of a parametric representation, by a set of configurable parameters in the phase detector 11a. The phase detector 11a operated with the parametric representation of the reference signal to produce a phase-sample timing signal comprising a sequence of times of fractional-cycle-intervals. In the present example, the phase detector 11a produced the phase-sample timing signal at a phase rate of 32 equal fractional-cycle-intervals per cycle of the reference signal.

The phase function representing the linear swept-frequency chirp which was used as the reference signal in the present example is well known, and can be represented mathematically as:

$$\varphi(t) = 2\pi f_1 t + \frac{\pi(f_2 - f_1)t^2}{L} \quad (84)$$

where
  $\phi(t)$ represents the phase of a continuous-phase signal representative of the actuator reference signal, in radians;
  $f_1$ represents the chirp starting frequency, in Hertz;
  $f_2$ represents the chirp ending frequency, in Hertz;
  L represents the chirp duration, in seconds;
  t represents the time from the initiation of the chirp, in seconds.

The fractional-cycle-intervals are equal fractional intervals of each cycle, which can be represented mathematically as:

$$\varphi_k = \frac{2\pi}{N}k, \quad k = 0, 1, 2, 3, \ldots \quad (85)$$

where $\varphi_k$ represents the phase value of the ending point of the $k^{th}$ interval;

N represents the integer number of intervals per cycle.

It follows that the times corresponding to the fractional-cycle-intervals for a linear swept-frequency chirp can be represented mathematically as:

$$\frac{\pi(f_2 - f_1)t^2}{L} + 2\pi f_1 t - \frac{2\pi}{N}k = 0, \quad k = 0, 1, 2, 3, \ldots \quad (86)$$

which is in the form of a quadratic equation in the variable t, having a well known solution for the roots. Therefore, the sequence of times $t_k$ corresponding to fraction-cycle-intervals for a linear swept-frequency chirp can be represented mathematically as the sequence of roots of the quadratic equation (86) as follows:

$$t_k = \frac{-f_1 + \sqrt{f_1^2 + (2k)(f_2 - f_1)/(NL)}}{(f_2 - f_1)/L}, \quad k = 0, 1, 2, 3, \ldots \quad (87)$$

In the embodiment of the phase detector 11*a* used in the present example, the phase detector 11*a* produced the phase-sample timing signal comprising the sequence of times $t_k$ of fractional-cycle-intervals in accordance with equation (87), with the specific value of N=32. This resulted in 32 fractional-cycle-intervals per cycle of the reference signal, each fractional-cycle-interval being an equal interval of phase.

In the embodiment of the parametric representation of the continuous-phase reference signal used in the present example, the starting frequency $f_1$ was 8 Hz, the ending frequency $f_2$ was 82 Hz, and the chirp duration L was 8 seconds.

1.06> The error attenuators 20*a*, 20*b*, 20*c* (FIG. 4), and 20*d* (FIG. 6) were each provided with a fractional-cycle-interval filter 10 having a harmonic filter 13 (FIG. 2). All four of the corresponding harmonic filters 13 were configured and operated with the same filter, which was a filter represented mathematically by the following filter function:

$$E(k) = \sum_{i=-31}^{+31} w_i S(k+i) \quad (88)$$

and operated with the following set of filter coefficients $w_i$:

$$w_i = \frac{32 - |i|}{32^2}, \quad (89)$$

$$i = -31, -30, -29, \ldots, 0, \ldots, 29, 30, 31$$

where

E(k) represents the filter output at the $k^{th}$ point of the phase-sampled signal series S(k) input to the harmonic filter 13;

S(k+i) represents points within the phase-sampled signal series S(k);

$w_i$ represents the set of filter coefficients determined by equation (89);

|i| represents the absolute value of the coefficient index i.

The filter can also be described as the convolution of two filters each having 32 filter coefficients of uniform weight.

In operation, the response of the filter was a linear phase response and an amplitude response having zeros (notches) at the first 31 harmonics of the fundamental frequency of the reference signal, including the fundamental frequency as the first harmonic.

1.07> The model basis function generator 71 was configured for several distinct differential equation models. Results for three particular models are described herein, and the models are referred to herein as Model A, Model B, and Model C. The three particular models used are described in Table 3.

The models listed in Table 3 represent force-balance differential equation models of the driving-point response of a semi-infinite elastic half space. These models are in accordance with the zero-mass driving element model depicted in FIG. 1C. The driving element is effectively zero mass because the mass of the driving element has been incorporated into the right-hand side function, which is the weighted sum estimate of the driving force signal, in accordance with equation (83) and description thereof. Model A comprises two basis functions, Model B comprises 6 basis functions, and Model C comprises 11 basis functions.

TABLE 3

MODEL BASIS FUNCTION GENERATOR:
Differential equation models used in this example

| | | |
|---|---|---|
| Model A | linear elastic help-space model | |
| differential equation model: | $b_1 v + k_1 x = F_d$ | (90) |
| model basis functions Z(t): | v(t), x(t) | (91) |
| right-hand side function Y(t): | $F_d(t)$ | (92) |
| Model B | nonlinear elastic half-space model; $5^{th}$ degree nonlinear symmetric (odd-degree terms only) | |
| differential equation model: | $\sum_{i=1,3,5}(b_i v^i + k_i x^i) = F_d$ | (93) |
| model basis functions Z(t): | $[v(t)]^i$, $[x(t)]^i$, for i = 1, 3, 5 | (94) |
| right-hand side function Y(t): | $F_d(t)$ | (95) |
| Model C | nonlinear elastic half-space model; $5^{th}$ degree nonlinear asymmetric, with displacement-dependent damping term | |
| differential equation model: | $c_1 vx + \sum_{i=1}^{5}(b_i v^i + k_i x^i) = F_d$ | (96) |
| model basis functions Z(t): | [v(t)x(t)], $[v(t)]^i$, $[x(t)]^i$, for i = 1, 2, 3, 4, 5 | (97) |
| right-hand side function Y(t): | $F_d(t)$ | (98) |

Notes:
$F_d$ represents the driving force;
v represents the driving-point velocity;
x represents the driving-point displacement;
$b_i$ are coefficients of viscosity, $b_1$ representing first-order viscosity;
$k_i$ are coefficients of stiffness, $k_1$ representing first-order stiffness;
$c_1$ is the coefficient of the displacement-dependent damping term;
(t) represents a function of time.

The three embodiments of the differential equation model listed in Table 3 (Models A-C) comprise terms for driving-point velocity and driving-point displacement. Models A-C have no terms on the left-hand side which depend on driving-point acceleration. Therefore the model basis functions depend on two input signals only: driving-point velocity and driving-point displacement. The particular embodiment of the driving-point analyzer system 80 used for the present example comprises a model basis-function generator having two input signals: a first input signal representative of the driving-point velocity, and a second input signal representative of the driving-point displacement. Therefore the particular embodiment of the linear system former 70 used for the present example comprises three input signals: a driving force signal, a driving-point velocity signal, and a driving-point displacement signal.

1.08> The design matrix former 72 was operated in two different modes to form and produce the design matrix: a first mode having a single, fixed-length time window; and a second mode having a sequence of overlapping time windows that collectively spanned the duration of the driving force chirp. In the first mode, the solver 80 determined a single set of solution coefficients representing elastic properties for the single time window represented by the design matrix. In the second mode, the solver 80 determined a set of solution coefficients for each one of the overlapping time windows in the sequence, which resulted in a series of values for each coefficient. The series of values of each coefficient represents the value of the coefficient as a function of time.

In the first mode the single time window comprised 200 data samples for each basis function signal (200 msec at 1 msec sample interval). In the second mode each time window comprised 500 data samples for each basis function signal (500 msec at 1 msec sample interval). Because the number of data samples per basis function signal exceeds the number of basis functions for the particular differential equation models of this example, each design matrix output produced by the design matrix former 72 in the present example comprises an overdetermined system of linear equations.

The design matrix former 72 applied scale factors to the basis-function signals, with scale factors designed such that the scaled basis-function signals all had approximately the same amplitude. This was done because the amplitude scales of the basis-function signals would otherwise differ by several orders of magnitude. Using basis function signals with widely different amplitudes produces an ill-conditioned design matrix, and results in a solution for the parameter coefficients which may be dominated by rounding error and other numerical noises. Using basis functions scaled to approximately equal amplitudes improves the conditioning of the design matrix, and improves the quality of the solution.

In particular, each displacement signal term in a basis function was scaled by an angular frequency factor, a constant representing the average angular frequency of the reference signal within the particular time window used by the design matrix former 72. Applying the frequency-proportional scale factor to the displacement signal produced a scaled displacement signal approximately equal in amplitude to the velocity signal. Other scale factors were also used to produce basis function signals with approximately equal amplitudes.

The scale factor values were constant within each design matrix criterion window. The design matrix former 72 controlled the conditioning of the design matrix by adjusting the value of each scale factor for each new window.

The scale factors used by the design matrix former 72 were known. The parameter coefficients which were output by the solver 80 were re-scaled to a desired output scale based on the known values of the several scale factors used within the system, which comprised the scale factors applied to the basis function signals by the design matrix former 72, and the scale factors of the acceleration signals used as initial input to the driving-point analyzer system 90.

A fractional-cycle-interval spectrum analysis system 110 was used to analyze the anharmonic components of the driving-point acceleration signal. The fractional-cycle-interval spectrum analyzer used for this particular example was constructed and operated in accordance with the schematic diagram of FIG. 6.

Results

The experimental procedures described herein were used to determine a best-fit value of each of the parameter coefficients of the elastic models described in Table 3. Based on the parameter coefficients so determined, several elastic properties of the soil at the location of the test were determined, comprising but not limited to a first-order stiffness, a first-order viscosity, an apparent stiffness as a function of driving force magnitude, a shear modulus, a shear wave speed, and a depth profile of shear wave speed.

Data and results shown herein are results from one particular application of the driving force chirp to the soil under test, and are shown herein as an example of the systems and methods of the present invention in operation.

The anharmonic character of the driving-point response of the soil under test was also analyzed using the fractional-cycle-interval spectrum analyzer, and it was found that the actual driving-point response was an anharmonic driving-point response comprising anharmonic driving-point motion signals characteristic of the response of a nonlinear elastic material.

An example of the result of the fractional-cycle-interval spectral analysis of the baseplate acceleration signal is shown in FIG. 8B, and for comparison FIG. 8A shows a conventional power spectrum of the same signal. The baseplate acceleration signal was measured and produced by the actuator control system at 1 msec sample intervals. The spectral analyses for FIGS. 8A and B were both done on substantially the same time window representing the first 2 seconds of the actuator chirp, and the same cosine window taper function was applied to the time window before each of the spectral analyses. Within this time window, the frequency of the actuator driving-force reference signal increases linearly from 8 Hz to 26.5 Hz.

In FIG. 8B, the horizontal axis represents pseudo-frequency values (cycles per radian), scaled in units representing the harmonic multiples of the fundamental frequency of the reference signal (each unit on the horizontal axis shown represents one cycle per $2\pi$ radians). The fractional-cycle-interval spectral analysis used a phase sample rate of 32 samples per cycle of the reference signal, so the Nyquist limit for this example is at the $16^{th}$ harmonic of the fundamental frequency of the reference signal. Harmonic multiple 1 represents an average temporal frequency of about 17 Hz, and harmonic multiple 16 represents an average temporal frequency of about 272 Hz, based on a window-weighted average of the frequency range within the time window of the analysis.

Harmonic components higher than the 16$^{th}$ harmonic can be resolved when the phase sample rate is increased to more than 32 samples per cycle.

The horizontal axes of both FIG. 8A and FIG. 8B are scaled to represent substantially the same range of frequencies.

Several important conclusions can be drawn from the results shown in FIG. 8B. First, it is apparent that the baseplate acceleration signal is dominated by a set of discrete harmonic components at harmonics of the reference signal. Based on the analysis shown in FIG. 8B, the set of discrete harmonic components represents about 98.6 percent of the total power in this particular baseplate acceleration signal. Frequencies other than the harmonic components represent about 1.4 percent of the total power.

Second, because the driving-point motion of the soil in this test is dominated by the set of harmonic components, the driving-point response is correctly classified as an anharmonic response. Therefore, the response of the soil is well represented by a nonlinear mathematical model of an ideal nonlinear elastic response, which comprises a set of harmonic frequency components at harmonics of the driving force (P. Bratu, 2003, "Dynamic response of nonlinear systems under stationary harmonic excitation", Facta Universitatis Series Mechanics, Automatic Control and Robotics, vol. 3, no. 15, p. 1073-1076).

And thirdly, FIG. 8B shows that the fractional-cycle-interval spectrum analysis system 110 has been used to sharply resolve the harmonic frequency components of a driving-point response signal. For the data in this case, FIG. 8B shows that the amplitude of the even-numbered harmonics is generally lower than the amplitude of the odd-numbered harmonics, that the harmonic components follow an orderly decrease in amplitude with increasing harmonic number, and that these amplitude relationships have been quantified by the analysis. By comparison with FIG. 8A, the conventional spectral analysis could not resolve or quantify these relationships, and did not correctly reveal the dominance of the harmonic components in relation to other signal components. The fractional-cycle-interval spectrum analysis system 110 was also used to quantify the phase relationships of the harmonic components.

Results and advantages of the fractional-cycle-interval filter 10 are illustrated in FIGS. 9A-C. FIG. 9A shows a driving-point velocity signal produced by integration of the baseplate acceleration signal with no error-correction or filtering applied. FIG. 9C shows an error-corrected driving-point velocity signal produced by integration of the same input, but with the benefit of a fractional-cycle-interval filter 10 for error-correction. FIG. 9B shows the error signal estimated by the fractional-cycle-interval filter 10.

It is apparent from FIG. 9A that the integration process introduced large artifacts which are not representative of the actual driving-point velocity. For example, the signal in FIG. 9A indicates that from about 4 to 4.5 seconds into the chirp, the actuator was drifting up, away from the ground and into the air, with an average velocity of about 20 cm/sec. This is obviously an artifact of the integration process. The actual driving-point velocity is known to be centered around a zero value. The integration artifacts comprise a combination of numerical integration error and measurement errors (noise) in the baseplate acceleration signal which are not representative of the actual motion of the baseplate.

The fractional-cycle-interval filter 10, together with an error attenuator 20, was used to estimate the combined measurement and integration error components of the velocity signal shown in FIG. 9A. The fractional-cycle-interval filter 10 and the error attenuator 20 were configured and operated as listed in Table 2 and described herein, using the same baseplate acceleration signal and the same integration parameters that were used to produce the signal in FIG. 9A. The error attenuator 20 removed the estimated error signal shown in FIG. 9B, and FIG. 9C shows the resulting output signal: the error-corrected driving-point velocity signal.

It is apparent from FIG. 9C that the error artifacts in FIG. 9A were substantially attenuated by the error attenuator 20 together with the fractional-cycle-interval filter 10. The driving-point velocity signal shown in FIG. 9C is more accurately representative of an actual driving-point velocity, and is useful for determining elastic properties. The fractional-cycle-interval filter estimated an error signal (FIG. 9B) which is a broad-band, apparently random signal. This error signal would not be as well represented by the standard practice of using a linear or low-order polynomial fit to the non-corrected signal in FIG. 9A.

The driving-point signal conditioner 60a processed the two measured input signals—the baseplate acceleration signal and the reaction-mass acceleration signal—and produced four output signals which are shown graphically in FIGS. 10A-D. The four output signals represent final error-corrected driving-point response signals, as follows:

| Figure | Signal | Signal Path |
| --- | --- | --- |
| FIG. 10A | final error-corrected driving-point acceleration signal | 51 |
| FIG. 10B | final error-corrected driving-point velocity signal | 47 |
| FIG. 10C | final error-corrected driving-point displacement signal | 43 |
| FIG. 10D | error-corrected driving force signal | 62 |

Referring to the graphs in FIGS. 10A-D, the vertical axes are scaled in units of measure of m/sec, cm/sec, mm, and kilo Newtons, respectively, and the horizontal axes are all shown with the same scale in units of seconds. The acceleration signal in FIG. 10A was integrated to generate the velocity signal in FIG. 10B, which was integrated to produce the displacement signal in FIG. 10C, by the action of the anharmonic motion signal integrator 30, also comprising error-correction using the fractional-cycle-interval filters 10 and differential error-correction using the first differentiator 33 and second differentiator 34. The driving-force signal in FIG. 10D was generated by the driving-point signal conditioner 60a by means of the weighted sum of the acceleration signal of FIG. 10A and the error-corrected reaction-mass acceleration signal as described herein.

The model basis-function generator 71 received the four error-corrected driving-point response signals shown in FIGS. 10A-D, and combined them to generate basis-function signals in accordance with the differential equation models described in Table 3. Note in FIGS. 10A-D that the amplitude of the four driving-point signals differ by orders of magnitude: the acceleration signal amplitude is approximately 100 m/sec$^2$ near the end of the chirp, at the same time the displacement signal amplitude is less than 5×10$^{-4}$ m, which is an amplitude scale ratio of more than five orders of magnitude. This illustrates why the basis-function scale factors used by the design matrix former 72 are important for improving the conditioning of the design matrix and controlling the stability and utility of the numerical result.

In a first operating mode, the design matrix former 72 generated a design matrix for a single time window comprising a 200 millisecond interval from 1.5 to 1.7 seconds after the initiation of the driving-force chirp, and using a selection criterion that comprised the full time window (i.e. there were no time gaps within the window). A design matrix was generated for each of the differential equation models. The time window 1.5-1.7 sec corresponds to a reference signal frequency range of 21.875-23.725 Hz, with an average frequency of 22.8 Hz. Therefore, this time window represents a narrow frequency band of 1.85 Hz range.

The solver 80 generated a set of best-fit parameter coefficients for each of the design matrices. The best-fit parameter coefficient solution results are listed in Table 4 for each of the differential equation models, with values scaled in the units of measure indicated in the table. The parameter coefficient results shown in Table 4 for each model represent an output of the of the driving-point analyzer system for the soil under test in the present example.

TABLE 4

SOLUTION RESULTS: Best-fit parameter coefficients
Results for a single time window: 1.5-1.7 sec, 21.875-23.725 Hz

| coefficient | Model A | Model B | Model C | Units of measure |
|---|---|---|---|---|
| $k_1$ | 169.3 | 212.0 | 207.6 | MegaNewton/m |
| $k_2$ | | | 1.11E+05 | MegaNewton/m$^2$ |
| $k_3$ | | −1.36E+08 | −1.04E+08 | MegaNewton/m$^3$ |
| $k_4$ | | | −2.06E+11 | MegaNewton/m$^4$ |
| $k_5$ | | 9.52E+13 | 9.17E+13 | MegaNewton/m$^5$ |
| $b_1$ | 0.8609 | 1.426 | 1.499 | MegaNewton sec/m |
| $b_2$ | | | −5.450 | MegaNewton sec$^2$/m$^2$ |
| $b_3$ | | −96.3 | −79.48 | MegaNewton sec$^3$/m$^3$ |
| $b_4$ | | | 337.8 | MegaNewton sec$^4$/m$^4$ |
| $b_5$ | | 3.53E+03 | 2.31E+03 | MegaNewton-sec$^5$/m$^5$ |
| $c_1$ | | | −879.493 | MegaNewton-sec/m$^2$ |

The stiffness coefficients $k_i$ and viscosity coefficients $b_i$ listed in Table 4 are representative of elastic properties of the soil under test. The displacement-dependent damping coefficient $c_1$ is representative of elastic properties of the soil, mechanical properties of the actuator, or a combination thereof. The stiffness and viscosity values shown in Table 4 are expressed in terms of units of force (Newtons), and can be expressed in terms of units of pressure (Pascals) by dividing by the defined surface area size of the actuator baseplate.

Results in Table 4 show that the linear Model A resulted in a solution for the first-order stiffness $k_1$ and first-order viscosity $b_1$ which are a substantial underestimate compared to the solutions which resulted from the non-linear models Model B and Model C.

FIGS. 11A-C show the driving force signal compared to the best fit solution result for each of the Models A-C, respectively. The entire time window (1500-1700 msec) used for the solution is shown. In FIGS. 11A-C, two curves are graphed in each figure: a solid curve and a dashed curve. The solid curve represents the driving force signal input, which was the same signal for all three models. The driving force signal input represents the right-hand side function Y(t) used as input to the solver 80. The dashed curve represents the best fit solution result for each respective model. The dashed curves were formed by back-substituting the coefficient solutions listed in Table 4 into the differential equation model used for each respective solution: each basis function signal was multiplied by its respective best-fit parameter coefficient solution, and summed according to the differential equation model, to form a synthetic force signal representative of a best-fit to the driving-force signal. In other words, the solid curve represents the driving force signal input, and each dashed curve represents a best-fit force synthesized from the parameter coefficients determined by the solution corresponding to each respective model.

Comparing the dashed curve to the solid curve in each of FIGS. 11A-C shows the differences between the driving force signal input and the solution result. FIG. 11A shows that Model A resulted in a fairly reasonable fit to the driving force signal input, but differences are apparent. FIG. 11B shows that Model B resulted in a slightly improved fit, but differences are only slightly smaller compared to Model A. FIG. 11C shows that Model C resulted in a substantially good fit to the driving force signal input, and a substantial improvement compared to either Model A or B. The improvement in the results for Model C are mostly attributable to the displacement-dependent damping term $c_1 v x$ in the differential equation model.

Even though the dashed curves in FIGS. 11A and 11B appear to have relatively small differences, the first-order coefficients of stiffness and viscosity listed in Table 4 for Model A are substantially different from Model B. The coefficients for Model A differ substantially from Model B primarily because of the nonlinear response of the material under test.

To help characterize the differences between the results for the linear and nonlinear models, other elastic properties were derived from the best-fit parameter coefficients. The force necessary to produce a given elastic displacement can be computed from the coefficients of stiffness according to each differential equation model, considering an elastic force component only, to form a relationship of force to displacement, as follows:

$$\text{Model A: } F(x) = k_1 x \quad (99)$$

$$\text{Model B: } F(x) = k_1 x + k_3 x^3 + k_5 x^5 \quad (100)$$

where

F(x) represents the elastic force component as a function of displacement;

$k_1$, $k_3$, $k_5$ represent the coefficients of stiffness corresponding to each of the models;

x represents the driving-point displacement.

Figure 12:
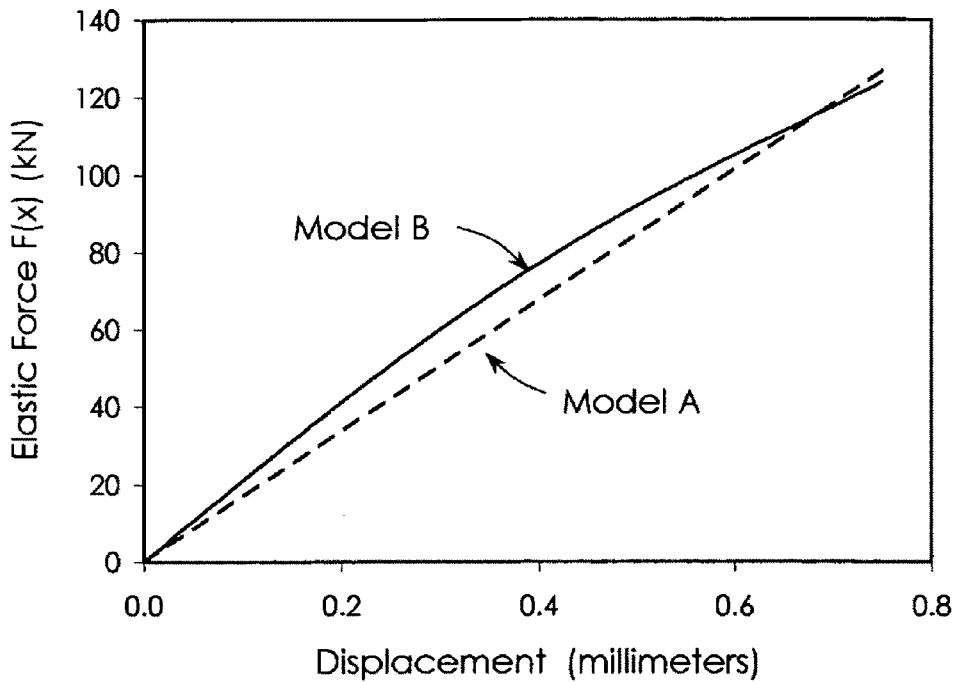
FIG. 12 is a plot of force-displacement curves synthesized from the solutions based on Models A and B, showing the nonlinearity of the solution using Model B.

FIG. 12 shows the elastic force component as a function of displacement for Models A and B, derived using equations (99) and (100) with the best-fit coefficients of stiffness listed in Table 4. The vertical axis represents the elastic force component, in kiloNewtons, and the horizontal axis represents displacement in millimeters. The solid curve shows the resulting elastic force component for Model B, and it is clearly nonlinear, representing the nonlinear elastic properties of the soil under test. The dashed curve shows the resulting elastic force component for Model A, which is constrained to be linear by the differential equation model used for Model A. The curves for both Model A and B cover the full amplitude of the driving-force displacement in this particular example, which was about 0.75 mm within the analysis time window (1.5-1.7 sec). FIG. 12 shows that the best-fit coefficients of stiffness for Model A and Model B both fit the peak amplitude force at approximately the same point, but have resulted in substantial differences at lower amplitude force levels.

Figure 13:
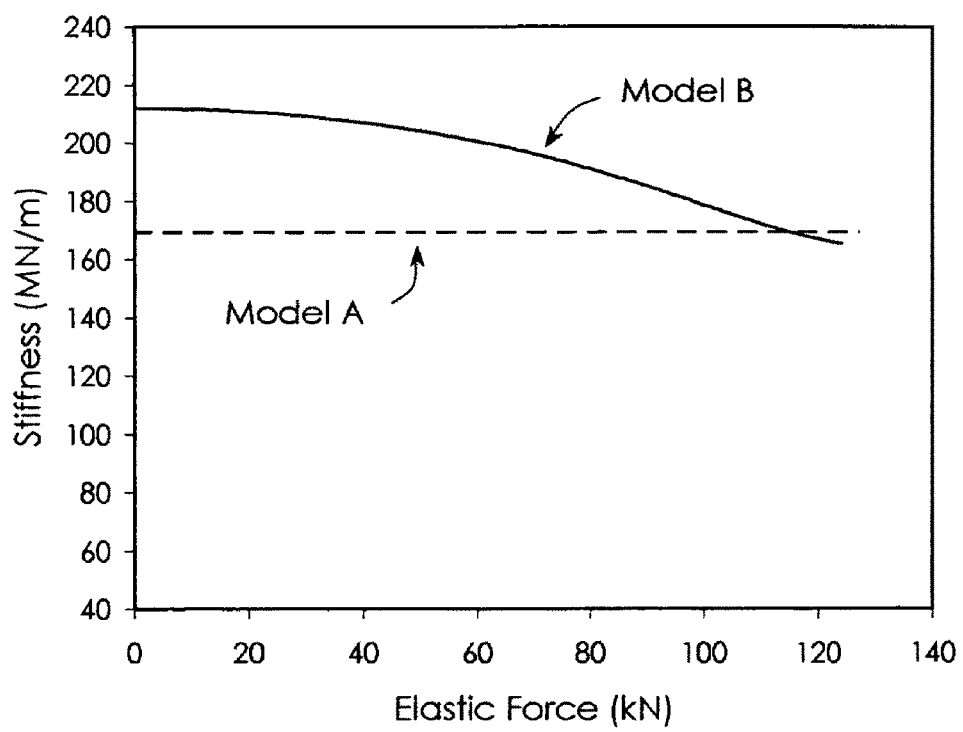
FIG. 13 is a plot of stiffness vs. elastic force curves synthesized from the solutions based on Models A and B, showing the benefit of the nonlinear Model B for determining stiffness at low force levels.

The differences between the linear and nonlinear results are shown even more clearly by converting the coefficients to an apparent stiffness function, shown in FIG. 13. The apparent stiffness K is the elastic force divided by the corresponding displacement: K=F(x)/x. The apparent stiffness as a function of force amplitude was determined from the parameter coefficient results for Models A and B, as shown graphically by the curves in FIG. 13.

FIG. 13 shows the apparent stiffness K as a function of the corresponding elastic force component F(x). The vertical axis represents the apparent stiffness in mega Newtons per meter, and the horizontal axis represents the corresponding elastic force component in kilonewtons. The solid curve represents the results for Model B, and the dashed line represents the results for Model A, each derived from the corresponding coefficients of stiffness listed in Table 4. The zero-intercept where each curve meets the vertical axis corresponds to the value of the first-order stiffness coefficient $k_1$. In particular, the apparent stiffness K at the zero-intercept represents stiffness at a near-zero displacement amplitude, within the small-amplitude approximation. Both Model A and B resulted in a similar stiffness value determined for a full amplitude displacement, but the nonlinear Model B resulted in a determination of a much higher stiffness value for a near-zero amplitude displacement.

The apparent stiffness result for Model B (solid curve in FIG. 13) shows a well-known behavior for many types of nonlinear elastic material: that for displacements which exceed the small-amplitude approximation, stiffness decreases as the applied force increases. It is known that soil and other earth materials can exhibit this type of nonlinear elastic behavior, and this behavior has limited most existing methods to using only small forces within the small amplitude approximation. FIG. 13 shows that the nonlinear parameter coefficients determined for Model B fit the known nonlinear elastic behavior of soil. In particular, the apparent stiffness result for Model B shows that the full amplitude range of the driving-point displacement signal exceeds the small-amplitude approximation for the soil under test in this particular example.

The differences in the coefficients resulting from the linear Model A and the nonlinear Model B are now apparent from FIG. 13. The first-order stiffness coefficient $k_1$ for Model A represents stiffness at full amplitude displacement. The first-order stiffness coefficient $k_1$ for Model B represents stiffness at near-zero amplitude displacement, within the small-amplitude approximation. At full amplitude, the apparent stiffness for both Models A and B are approximately the same, which is why the full amplitude waveforms shown in FIGS. 11A and B appear similar but with notable differences. The differences between results for Models A and B at near-zero amplitude displacement which are clearly apparent in FIG. 13 are less apparent in the full waveform representations in FIGS. 11A and B.

The Model B results in the present example show that the systems and methods of the present invention, configured for a nonlinear elastic differential equation model, were used to determine a coefficient of stiffness representative of a small-amplitude approximation, even though a very large driving force was applied to a nonlinear material which produced displacements exceeding the small amplitude approximation.

The apparent stiffness as a function of elastic force, and the elastic force as a function of displacement, shown graphically by the curves in FIGS. 12-13, represent elastic properties of the soil under test. These elastic properties were derived directly from the parameter coefficients listed in Table 4. Therefore these elastic properties are determined by the best-fit parameter coefficients produced by the driving-point analyzer system 90.

In the same fashion, the coefficient of viscosity resulting from use of the linear Model A differs from the corresponding coefficients for the nonlinear Models B and C. By the same logic and analysis described for the coefficients of stiffness, the first-order viscosity coefficient $b_1$ for Model A represents viscosity at full amplitude velocity. The first-order viscosity coefficient $b_1$ for Models B and C represent viscosity at near-zero amplitude velocity, within the small-amplitude approximation. Apparent viscosity as a function of force, and the viscous force component as a function of velocity, can be derived directly from the parameter coefficients listed in Table 4.

In the second operating mode, the design matrix former 72 generated a design matrix for a sequence of overlapping time windows, and for each window the solver 80 produced a set of best-fit parameter coefficients, to produce a series of parameter coefficient values representing the value of each parameter coefficient as a function of time. The series of parameter coefficient values are also representative of the coefficient values as a function of frequency, based on the known frequency of the driving force reference signal corresponding to the time at the center of each time window in the sequence. Results for the series of parameter coefficients so produced are described herein for the example of Model C only.

FIGS. 14A and B show graphically the series of results obtained for the first-order coefficients corresponding to Model C. The horizontal axes in Figs. A-C represent the time elapsed after the initiation of the driving force chirp, where the time assigned to each value is the time at the center of the particular analysis time window used for the corresponding value in the series. FIG. 14A shows the series of best-fit solution values obtained for the first-order stiffness coefficient $k_1$. The vertical axis of FIG. 14A represents the stiffness in mega Newtons per meter. FIG. 14B shows the series of best-fit solution values obtained for the first-order viscosity coefficient $b_1$. The vertical axis of FIG. 14B represents the viscosity in mega Newton-seconds per meter.

It is apparent from FIGS. 14A and B that the coefficients of stiffness and viscosity vary in a complicated way as a function of time during the sweep. This variation with time also represents a variation as a function of frequency, the frequency being the frequency of the driving-force reference signal. The stiffness coefficient $k_1$ (FIG. 14A) is generally increasing with time, but with substantial, irregular, variations.

The viscosity coefficient $b_1$ (FIG. 14B) has a broad maximum peak from about 1 to 3 seconds, and lower values at other times. The viscosity coefficient $b_1$ is a measure of energy dissipation, so larger values of the viscosity coefficient $b_1$ represent greater energy dissipation, and the broad maximum peak represents a maximum in radiation of elastic-wave energy into the earth. In particular, the broad maximum peak in the viscosity coefficient $b_1$ describes the frequency band of maximum Rayleigh wave energy radiated by the driving force. The broad maximum peak can be used to estimate the power spectral content of the radiated Rayleigh wave energy.

It is clear from FIGS. 14A and B that in the present example, there is not an obvious, single constant value of the stiffness coefficient or the viscosity coefficient that would be representative of the elastic response of the soil under test. FIGS. 14A and B make clear that methods which determine stiffness or viscosity by simply taking an average value over a wide range of frequencies would have in this case produced a result which would not be meaningfully representative of the complicated elastic response of the soil under test.

The variations in the parameter coefficients as a function of frequency reflect in a complicated way the elastic properties of the elastic material under test. The variations and relationships of one or more of the parameter coefficients as a function of frequency can be used to determine values of one or more elastic properties.

Lysmer showed in his elastic half-space solution for uniform periodic loading by a rigid circular footing that the variation in stiffness and viscosity as a function of frequency can be represented by a dimensionless function called a displacement function (Lysmer and Richart, 1966, "Dynamic response of footings to vertical loading", Journal of the Soil Mechanics and Foundations Division, Proc. ASCE, vol. 92, no. SM 1, p. 65-91).

Based on the solution by Lysmer (1966), the ratio of stiffness to viscosity is proportional to shear wave speed:

$$\frac{K}{C} = \left(\frac{a_0 F_1}{-F_2}\right) \times \left(\frac{V_S}{r_0}\right) \quad (101)$$

where

K represents Lysmer's designation for the dynamic stiffness coefficient;

C represents Lysmer's designation for the dynamic viscosity coefficient;

$V_S$ represents the shear-wave speed;

$r_0$ represents the radius of the circular footing;

$a_0$ represents a dimensionless frequency ratio;

$F_1$, $F_2$ are the real and imaginary parts of Lysmer's displacement function, and both represent dimensionless, real numbers.

Lysmer's dynamic stiffness K is equivalent to the first-order stiffness coefficient which is designated herein by $k_1$, and Lysmer's dynamic viscosity C is equivalent to the first-order viscosity coefficient which is designated herein by $b_1$. Therefore, equation (101) can be rearranged to express the shear-wave speed $V_S$ as follows:

$$V_S = \left(\frac{-F_2}{a_0 F_1}\right) \times \left(\frac{r_0 k_1}{b_1}\right) \quad (102)$$

The dimensionless ratio $-F_2/(a_0 F_1)$ is a complicated function of frequency and the elastic properties of the elastic half-space. Lysmer gives the following definition of the dimensionless frequency $a_0$:

$$a_0 = \frac{r_0}{V_S} \omega \quad (103)$$

where $\omega$ represents the angular frequency of the driving force reference.

FIG. 14C shows a plot representing the values of the first-order stiffness/viscosity ratio $k_1/b_1$ as a function of time. The $k_1/b_1$ ratio shown FIG. 14C is based on the same values of $k_1$ and $b_1$ which are plotted in FIGS. 14A and B. The vertical axis in FIG. 14C represents the stiffness/viscosity ratio in units of reciprocal seconds. FIG. 14C shows that the value of the stiffness/viscosity ratio varies in a complicated way by more than a factor of 5 over the range of frequencies of the driving force chirp. In order to obtain useful information about the shear-wave velocity from the value of the ratio $k_1/b_1$, values need to be determined for the dimensionless ratio $-F_2/(a_0 F_1)$ in equation (102).

In the present example, at least one particular value of the dimensionless ratio $-F_2/(a_0 F_1)$ was determined from the sequence of values of $k_1$ and $b_1$. Combining equations (102) and (103) gives the following relation for the displacement function ratio $-F_2/F_1$:

$$\left(\frac{-F_2}{F_1}\right) = \frac{\omega b_1}{k_1} \quad (104)$$

where $k_1$ and $b_1$ represent the first-order coefficients of stiffness and viscosity. (It should be noted that Lysmer used the designation $k_1$ to represent a different quantity than the usage herein. In my equation (104) and throughout the description of the present invention herein I use the designation $k_1$ to represent the first-order stiffness coefficient in accordance with the differential equation models listed in Table 3 and elsewhere herein. My first-order stiffness coefficient $k_1$ is equivalent to Lysmer's dynamic stiffness K, and my first-order viscosity coefficient $b_1$ is equivalent to Lysmer's dynamic viscosity C.) Lysmer provided a particular solution of the values of $-F_2$ and $F_1$ as a function of the dimensionless frequency ratio $a_0$ for the particular case of an elastic half-space with a value of Poisson's ratio equal to one-third. For the particular case of Poisson's ratio equal to one-third, Lysmer shows that the value of $-F_2$ equals the value of $F_1$ at a value of $a_0$ approximately equal to one. Other investigators have also provided particular solutions for $-F_2$ and $F_1$ for values of $a_0$ close to 1.0 at other values of Poisson's ratio from 0 to 0.5, and their results are similar to Lysmers, but with small differences. Lysmer shows other investigator's solutions using other values of Poisson's ratio which result in values of $a_0$ in the range of approximately 0.9 to 1.0 at the point where $\omega b_1/k_1 = 1.0$. Therefore $a_0$ is approximately equal to 0.95 at the point where the ratio $-F_2/F_1$ is equal to one:

$$a_0 = 0.95 \pm 0.05 \quad (105)$$

where $$\frac{-F_2}{F_1} = 1$$

I combined equations (103), (104) and (105) to provide a method for determining a value of $a_0$ and a value of the shear-wave speed $V_S$ that is substantially insensitive to Poisson's ratio:

$$\left.\begin{array}{l} a_0 = 0.95 \\ V_S = \dfrac{r_0 \omega}{0.95} \end{array}\right\} \quad (106)$$

where $$\frac{\omega b_1}{k_1} = 1$$

By assuming a value of $a_0 = 0.95$, the determination of a value of shear-wave speed is expected to have less than about five percent uncertainty due to uncertainty in Poisson's ratio. It is an advantage that the method embodied in the expression of equation (106) is substantially insensitive to Poisson's ratio, wherein substantially insensitive means variation of less than ten percent.

A more general solution for shear-wave velocity at other values of $a_0$ can be expressed as follows:

$$V_S = \frac{r_0 \omega}{a_0} \quad (107)$$

where $$\frac{\omega b_1}{k_1} = 1$$

where the particular value of $a_0$ comprises a function of Poisson's ratio.

Figure 15:
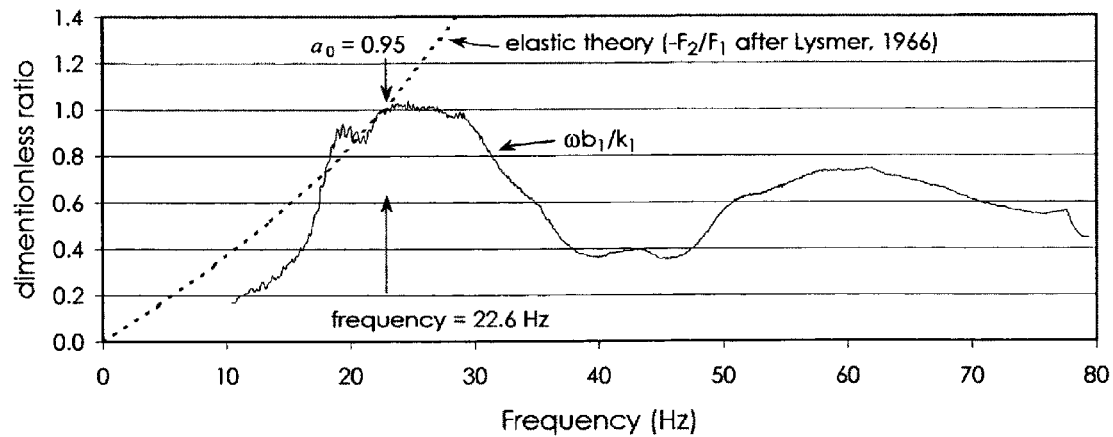
FIG. 15 is a plot comparing experimental results of Example 1 to elastic half-space theory, showing where shear-wave speed can be determined with full advantage of elastic theory.

For the present example, I determined values of the ratio $\omega b_1/k_1$ as a function of frequency, using the solution results for the coefficients $k_1$ and $b_1$ which were shown individually in FIGS. 14A and B for Model C. The solid curve in FIG. 15 represents the values of the ratio $\omega b_1/k_1$ so determined. The vertical axis in FIG. 15 represents the dimensionless value of the ratio, and the horizontal axis represents the frequency of the driving force reference signal in hertz.

The solid curve in FIG. 15 shows that from 10 Hz to 20 Hz the value of the ratio $\omega b_1/k_1$ increases and reaches a value of 1.0 at about 22.6 Hz. From equation (106) and the value of $r_0$ listed in Table 1, the shear-wave speed at this frequency point was determined to be about 135 m/sec, based on a value of $a_0$=0.95. The value of the shear-wave speed determined for this particular case is in the approximate range 135+/−7 m/sec, depending on Poisson's ratio.

No simplifications of the elastic half-space theory are required to use the point where the ratio $\omega b_1/k_1$=1.0 as a means to determine the shear-wave speed, and the method is substantially insensitive to Poisson's ratio.

To compare the theoretical elastic half-space response to the actual driving-point response of the soil under test, the dashed curve in FIG. 15 represents the ratio $-F_2/F_1$ based on the ideal elastic half-space solution presented by Lysmer. The dashed curve is the ratio of Lysmer's results for $-F_2$ and $F_1$ as a function of $a_0$, which I re-scaled as a function of frequency based on the particular value of $a_0$=0.95 at 22.6 Hz. Because Lysmer's results are for a homogeneous half-space, the dashed curve in FIG. 15 represents an elastic half-space model for a material with a uniform shear-wave speed of about 135 m/sec. At frequencies lower than 22.6 Hz, the experimental data represented by the solid curve differ from the dashed curve because the actual shear-wave speed of the material under test is not uniform, but varies with depth below the driving-point location. For frequency at and below 22.6 Hz, the experimental results in the present example appear to be in accordance with Lysmer's model of the driving-point response of an elastic half-space.

At frequencies higher than 22.6 Hz the experimental results for $\omega b_1/k_1$ appear to deviate from Lysmer's elastic half-space theory, for the particular results of the present example represented in FIG. 15. Based on equation (106) the wavelength of the shear wave is equal to $2\pi r_0$ where $(\omega b_1/k_1)$=1. This wavelength is close to the diameter size of the driving element contact surface area. At much higher frequencies, the shear-wave wavelength becomes much shorter than the size of the driving element. It appears that the results in the present example deviate from the elastic half-space theory for shear-wave wavelengths close to and shorter than the dimensions of the baseplate. Possible reasons for this are interference from standing-waves generated within shallow layers close to the baseplate, or to partially inelastic behavior of material very close to the baseplate.

A value of the shear modulus G was determined (shown in Table 5) from the first-order stiffness coefficient using the well known relationship for elastic response to a static (zero frequency) load:

$$K = \frac{4Gr_0}{1-\mu} \quad (108)$$

where $\mu$ represents Poisson's ratio and K represents the static stiffness at zero frequency. For the case of Model C used for the present example, K in equation (108) is approximately equivalent to the first-order stiffness $k_1$.

A value of the volumetric mass density $\rho$ was determined from the relationship of shear-wave speed and shear modulus G:

$$V_S = \sqrt{\frac{G}{\rho}} \quad (109)$$

The values of the density and shear modulus were determined based on an assumption of the value of Poisson's ratio, and therefore represent an approximate estimate.

The elastic properties determined from the driving point response are assumed to represent the properties of the material at a depth of about one-half the wavelength of the Rayleigh waves generated at the same time. The Rayleigh wavelength was assumed to be 0.95 times the wavelength of the shear waves. Therefore, the elastic properties are attributed to a depth as follows:

$$\text{depth} = \frac{0.95 V_S}{2f} \quad (110)$$

where f represents the frequency of the driving force reference signal.

Table 5 summarizes the elastic properties which were determined from the driving-point response at the selected frequency where $(\omega b_1/k_1)$=1. To determine the value of the shear modulus G, Poisson's ratio was assumed to be 0.33.

TABLE 5

ELASTIC PROPERTIES DETERMINED
FROM DRIVING-POINT RESPONSE
For the particular case where $(\omega b_1/k_1) = 1.0$

| Elastic Property | Symbol | Value | Description |
| --- | --- | --- | --- |
| first-order stiffness | $k_1$ | 215 MN/m | determined by the |
| first-order viscosity | $b_1$ | 1.52 MN-sec/m | driving-point analyzer system 90 for one of a sequence of overlapping time windows |
| Lysmer's dimentionless frequency ratio | $a_0$ | 0.95 | $a_0 = 0.95$ where $(\omega b_1/k_1) = 1.0$ |
| frequency where $a_0 = 0.95$ | f | 22.6 Hz | selected at the lowest frequency where $(\omega b_1/k_1) = 1.0$ |
| shear-wave speed | $V_S$ | 135 m/sec | $V_S = \frac{r_0 \omega}{a_0}$ |

TABLE 5-continued

ELASTIC PROPERTIES DETERMINED
FROM DRIVING-POINT RESPONSE
For the particular case where $(\omega b_1/k_1) = 1.0$

| Elastic Property | Symbol | Value | Description |
|---|---|---|---|
| shear modulus | G | 40 MPa | $G = \dfrac{k_1(1-\mu)}{4r_0}$ for $\mu = 0.33$ |
| density | $\rho$ | 2.2 g/cm³ | $\rho = \dfrac{V_S^2}{G}$ |
| depth below baseplate | | 2.8 m | $\text{depth} = \dfrac{0.95 V_S}{2f}$ |

It is an advantage of the present invention that values of the first-order stiffness and first-order viscosity can be determined as a function of time, which provides a means to produce a signal representative of $\omega b_1/k_1$ which can be analyzed to select a particular frequency where the ratio $-F_2/F_1$ is approximately 1.0, and to determine a value of one or more elastic properties at the selected particular frequency.

Elastic properties can also be determined at frequencies other than the frequency where $(\omega b_1/k_1)=1$. Based on several simplifying assumptions, Lysmer developed a simplified analog of the complicated frequency-dependent ratio $F_2/(a_0 F_1)$, the simplified analog comprising approximating $F_2/(a_0 F_1)$ as a constant independent of frequency, assigning a constant value of 0.85:

$$\left(\frac{-F_2}{a_0 F_1}\right) \approx 0.85. \tag{111}$$

Substituting equation (111) into equation (102) yields an approximation for shear-wave speed:

$$V_S \approx 0.85 \times \left(\frac{r_0 k_1}{b_1}\right). \tag{112}$$

I determined values of $V_S$ in accordance with equation (112) for the series of values of $b_1/k_1$ represented by the curve shown in FIG. 14C for the frequency of the driving force reference signal from 0 to 22.6 Hz. For each value of $V_S$ I also determined a corresponding value of depth by the method described in Table 5 and the description thereof. The $V_S$-depth pairs comprise a depth profile of the variation of shear-wave speed with depth. Based on the values of VS so determined, the same logic can be applied to produce a depth profile for any one or more of the other elastic properties shown in Table 5 except for $a_0$.

Figure 16:
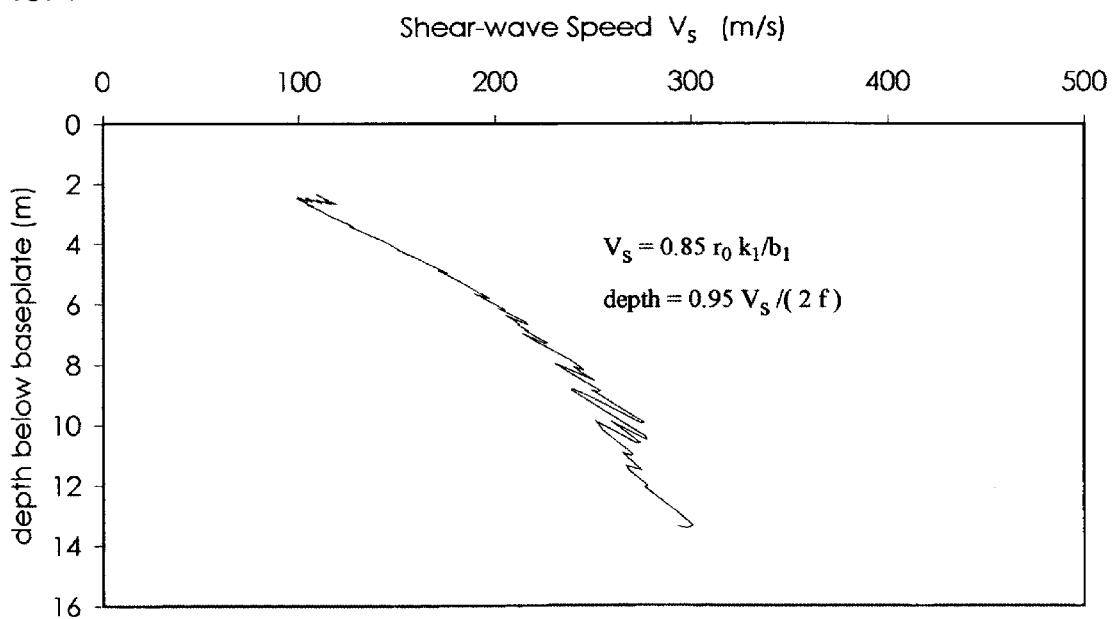
FIG. 16 is a plot of a depth profile of shear-wave speed, determined from the data of FIG. 14C, illustrating advantages provided by the systems and methods of the present invention.

FIG. 16 shows graphically the depth profile representative of the variation of shear-wave speed with depth below the baseplate. A depth profile of near-surface elastic wave speed is useful for improving the seismic images produced in seismic surveying, by providing a means to measure and compensate for near-surface variation in elastic properties. A depth profile of near-surface shear-wave speed, as well as depth profiles of other elastic properties, are useful for evaluating the mechanical properties of the ground for engineering design and construction of foundations and roads, and for assessing earthquake hazard susceptibility of near-surface earth materials.

It is well known by those skilled in the art that the properties determined in the present example and listed in Table 5 can be used to derive other elastic properties comprising any of the following: P-wave velocity, Young's modulus, bulk modulus, and/or Lame constant lambda. It will also be apparent that a depth profile of any of these properties can be produced by the methods described in the present example.

The present example described the operation of one particular embodiment of the systems and methods of the present invention in actual practice, and demonstrated several of the uses and advantages. The fractional-cycle-interval spectrum analysis system 110 was used to show that the driving-point motion of a real, nonlinear elastic material was correctly characterized as an anharmonic signal. The advantages of the fractional-cycle-interval filter 10 were shown for removing integration error from the driving-point motion signals. The driving-point analyzer system 90 was used to process an anharmonic driving-point response exceeding the small amplitude approximation, and to determine elastic properties representative of a near-zero amplitude response. Three different differential equation models were used in the driving-point analyzer system 90, which provided a means to evaluate and characterize the nonlinear behavior of the soil under test, and a means to evaluate the fitness of alternative models of elastic behavior. Elastic properties were determined for a single, narrow-band, time window, which showed the advantages of the linear system solver 80 for determining elastic properties from a signal comprising an anharmonic response, and the advantages of using the full information represented by the harmonic components for determining nonlinear properties of a nonlinear elastic material. Elastic properties were determined for a sequence of overlapping time windows, to produce values of the elastic properties as a function of time, which showed the advantages of the design matrix former 72 and the linear system solver 80 for determining values of elastic properties as a time series. Methods based on elastic half-space theory were used to show that the best-fit parameter coefficients produced by the driving-point analyzer system are representative of elastic properties, and that the coefficients so produced are useful for determining elastic properties comprising any one or more of the following properties: first-order stiffness; first-order viscosity; second-, third-, fourth-, and fifth-order stiffness and viscosity; displacement-dependent damping; apparent stiffness as a function of driving force; shear-wave speed; shear modulus; density; and shear-wave speed variation with depth below the baseplate. In addition, a depth below the baseplate was determined for several of the forgoing elastic properties, the depth representing the location of the material to which the elastic property could be attributed.

It is understood by skilled practitioners that any of the various forces described herein can be expressed as pressure or stress by dividing the force by the surface area size of the corresponding contact surface area over which the force is applied. The elasticity and viscosity relationships have been described herein in terms of force solely for purposes of clarity and uniformity of the description, and can be expressed in terms of pressure or stress without changing the substance, logic, or scope of the present invention.

I claim:

1. A system for determining a value of one or more elastic properties of a material, the system using input signals comprising a first input signal representative of a driving force exerted on the material by an actuator at a driving-point; a second input signal representative of a driving-point velocity corresponding to the driving force; and a third input signal representative of a driving-point displacement corresponding to the driving force, the system comprising:
(a) a generator for generating a basis function signal for each basis function term of a differential equation model of the motion of the driving-point, wherein at least one basis function term comprises a function of the second input signal, and at least one basis function term comprises a function of the third input signal; and
(b) a processor which uses a fitting process for determining coefficients of a linear combination of the basis function signals which fits the first input signal, wherein at least one of the determined coefficients is representative of the value of one or more elastic properties of the material.

2. The system of claim 1, wherein the material is an in situ material or an isolated sample of material.

3. The system of claim 1, wherein the material is earth material, soil, subsoil, rock, weathered rock, sand, gravel, silt, clay, fill, geologic formations, foundation soil, or combinations thereof.

4. The system of claim 1, wherein the actuator is a reciprocating actuator, a servo-hydraulic actuator, an electro-dynamic actuator, a seismic vibrator, a rotating mass actuator, or an impulse actuator.

5. The system of claim 1, wherein the differential equation model comprises a force balance differential equation model of a spring-damper system or a mass-spring-damper system.

6. The system of claim 1, wherein the differential equation model comprises a displacement term and a velocity term, and the determined coefficient corresponding to the displacement term is thereby representative of the value of a stiffness property of the material, and the determined coefficient corresponding to the velocity term is thereby representative of the value of a viscosity property of the material.

7. The system of claim 1, wherein the differential equation model comprises a polynomial function of the driving-point displacement, and each determined coefficient corresponding to a displacement term is thereby representative of the value of a stiffness property of the material.

8. The system of claim 1, wherein the differential equation model comprises a polynomial function of the driving-point velocity, and each determined coefficient corresponding to a velocity term is thereby representative of the value of a viscosity property of the material.

9. The system of claim 1, wherein the differential equation model comprises a displacement-dependent damping term, and the determined coefficient corresponding to the displacement-dependent damping term comprises a coefficient of displacement-dependent damping.

10. The system of claim 1, wherein the generator is a programmable processor, microprocessor, digital signal processor, or computer.

11. The system of claim 1, wherein generating a basis function signal comprises generating a basis function value at each of a set of distinct times, and wherein the linear combination comprises the linear combination of the basis function signals at the set of distinct times.

12. The system of claim 11, wherein the set of distinct times is in time-sequential order, not in time-sequential order, at uniform intervals of time, at non-uniform intervals of time, comprising gaps in time, or a set of times in any combinations thereof.

13. The system of claim 1, further comprising a signal sampling means for selecting a sequence of time windows of the basis function signals, and wherein the fitting process comprises fitting each of the sequence of time windows, thereby determining a series of values of each coefficient, the series of values being representative of one or more elastic properties as a function of time.

14. The system of claim 1, wherein the basis function signals and the first input signal comprise an overdetermined system of linear equations, and the fitting process comprises solving the system of linear equations.

15. The system of claim 1, wherein the basis function signals comprise a design matrix representative of the basis function signals, and wherein the fitting process comprises matrix inversion of the design matrix.

16. The system of claim 15, wherein the fitting process comprises singular value decomposition of the design matrix, to thereby determine the coefficients of the linear combination.

17. The system of claim 1, wherein the input signals further comprise a fourth input signal representative of a driving-point acceleration corresponding to the driving force, and wherein at least one basis function term comprises a function of the fourth input signal.

18. The system of claim 1, wherein the elastic property is a stiffness, a viscosity, a shear modulus, or a shear-wave speed.

19. The system of claim 1, wherein at least one of the second or third input signals is produced by a process comprising integration of a baseplate acceleration signal of the actuator.

20. The system of claim 1, further comprising a filter for filtering at least one of the first, second, or third input signals before generating the basis function signals, the filter comprising:
(a) a phase detector for generating a phase-sample timing signal representative of a sequence of times corresponding to substantially equal intervals of phase of a phase reference signal, wherein the equal intervals of phase comprise an integer number N of phase intervals per cycle of the phase reference signal;
(b) a sampler for sampling an input signal at the sequence of times corresponding to the phase-sample timing signal, to generate a phase-sampled signal; and
(c) a filter for filtering the phase-sampled signal to generate a filtered signal, wherein the filter attenuates or preserves each of one or more selected signal components that comprise one or more harmonic multiples of the fundamental frequency of the phase reference signal, such that the filter response comprises a magnitude response either substantially representative of zero or substantially representative of unity at each of the selected harmonic multiples.

21. The system of claim 20 further comprising a re-sampler for resampling the filtered signal at uniform intervals of time, to produce a re-sampled time series output signal.

22. The system of claim 20, wherein the phase reference signal comprises a driving force reference signal or a parametric representation of a function representative of the phase reference signal.

23. A method for determining a value of one or more elastic properties of a material, the method comprising:
(a) exerting a driving force on the material by an actuator at a driving point;
(b) producing input signals comprising a first input signal representative of the driving force exerted on the material, a second input signal representative of a driving-point velocity corresponding to the driving force, and a third input signal representative of a driving-point displacement corresponding to the driving force
(c) generating a basis function signal for each basis function term of a differential equation model of the motion of the driving-point, wherein at least one basis function term comprises a function of the second input signal, and at least one basis function term comprises a function of the third input signal; and (d) determining coefficients of a linear combination of the basis function signals which fits the first input signal, wherein at least one of the determined coefficients is representative of the value of one or more elastic properties of the material.

24. The method of claim 23, wherein the material is earth material, soil, subsoil, rock, weathered rock, sand, gravel, silt, clay, fill, geologic formations, foundation soil, or combinations thereof.

25. The method of claim 23, wherein the actuator is a reciprocating actuator, a servo-hydraulic actuator, an electrodynamic actuator, a seismic vibrator, a rotating mass actuator, or an impulse actuator.

26. The method of claim 23, wherein the differential equation model comprises a polynomial function of the driving-point displacement, and each determined coefficient corresponding to a displacement term is thereby representative of the value of a stiffness property of the material.

27. The method of claim 23, wherein the differential equation model comprises a polynomial function of the driving-point velocity, and each determined coefficient corresponding to a velocity term is thereby representative of the value of a viscosity property of the material.

28. The method of claim 23, wherein the generating a basis function signal comprises generating a basis function value at each of a set of distinct times, and wherein the linear combination comprises the linear combination of the basis function signals at the set of distinct times.

29. The method of claim 28, wherein the set of distinct times is in time-sequential order, not in time-sequential order, at uniform intervals of time, at non-uniform intervals of time, comprising gaps in time, or a set of times in any combinations thereof.

30. The method of claim 23 further comprising selecting a sequence of time windows of the basis function signals, and wherein the determining coefficients comprises determining coefficients for each of the sequence of time windows, thereby determining a series of values of each coefficient, the series of values being representative of one or more elastic properties as a function of time.

31. The method of claim 23, wherein the basis function signals and the first input signal comprise an overdetermined system of linear equations, and determining coefficients comprises solving the system of linear equations.

32. The method of claim 23, wherein the basis function signals comprise a design matrix representative of the basis function signals, and wherein determining coefficients comprises matrix inversion of the design matrix.

33. The method of claim 32, wherein determining coefficients comprises singular value decomposition of the design matrix, to thereby determine the coefficients of the linear combination.

34. The method of claim 23, wherein the input signals further comprise a fourth input signal representative of a driving-point acceleration corresponding to the driving force, and wherein at least one basis function term comprises a function of the fourth input signal.

35. The method of claim 23, wherein the elastic property is a stiffness, a viscosity, a shear modulus, or a shear-wave speed.

36. A non-transitory computer-readable medium comprising computer instructions stored therein for determining a value of one or more elastic properties of a material, using input signals comprising a first input signal representative of a driving force exerted on the material by an actuator at a driving-point, a second input signal representative of a driving-point velocity corresponding to the driving force, and a third input signal representative of a driving-point displacement corresponding to the driving force, the computer instructions comprising instructions for causing a programmable processor to:

(a) generate a basis function signal for each basis function term of a differential equation model of the motion of the driving-point, wherein at least one basis function term comprises a function of the second input signal, and at least one basis function term comprises a function of the third input signal; and (b) determine coefficients of a linear combination of the basis function signals which fits the first input signal, wherein at least one of the determined coefficients is representative of the value of one or more elastic properties of the material.

37. The non-transitory computer-readable medium of claim 36, wherein the differential equation model comprises a polynomial function of the driving-point displacement, and each determined coefficient corresponding to a displacement term is thereby representative of the value of a stiffness property of the material.

38. The non-transitory computer-readable medium of claim 36, wherein the differential equation model comprises a polynomial function of the driving-point velocity, and each determined coefficient corresponding to a velocity term is thereby representative of the value of a viscosity property of the material.

39. The non-transitory computer-readable medium of claim 36, wherein generating a basis function signal comprises generating a basis function value at each of a set of distinct times, and wherein the linear combination comprises the linear combination of the basis function signals at the set of distinct times.

40. The non-transitory computer-readable medium of claim 39, wherein the set of distinct times is in time-sequential order, not in time-sequential order, at uniform intervals of time, at non-uniform intervals of time, comprising gaps in time, or a set of times in any combinations thereof.

41. The non-transitory computer-readable medium of claim 36, wherein the basis function signals and the first input signal comprise an overdetermined system of linear equations, and determining coefficients comprises solving the system of linear equations.

42. The non-transitory computer-readable medium of claim 36, wherein the basis function signals comprise a design matrix representative of the basis function signals, and wherein determining coefficients comprises matrix inversion of the design matrix.

43. The non-transitory computer-readable medium of claim 36, wherein the elastic property is a stiffness, a viscosity, a shear modulus, or a shear-wave speed.

44. A system for determining a value of one or more elastic properties of an in situ material at or near a surface of the earth, the system using input signals comprising a first input signal representative of a driving force exerted on the in situ material by an actuator at a driving-point; a second input signal representative of a driving-point velocity corresponding to the driving force; and a third input signal representative of a driving-point displacement corresponding to the driving force, the system comprising:

(a) a generator for generating a basis function signal for each basis function term of a differential equation model of the motion of the driving-point, wherein the differential equation model comprises a polynomial function of the driving-point displacement and a polynomial function of the driving-point velocity, and wherein generating a basis function signal comprises generating a basis function value at each of a set of distinct times; and (b) a processor which uses a fitting process for determining coefficients of a linear combination of the basis function signals which fits the first input signal, wherein the basis function signals and the first input signal comprise an overdetermined system of linear equations, and wherein the fitting process comprises solving the overdetermined system of linear equations to determine a value of each coefficient, and wherein each determined coefficient corresponding to a displacement term is then representative of the value of a stiffness property of the in situ material, and each determined coefficient corresponding to a velocity term is then representative of the value of a viscosity property of the in situ material.

* * * * *